US011065317B2

(12) United States Patent
Findeis et al.

(10) Patent No.: US 11,065,317 B2
(45) Date of Patent: Jul. 20, 2021

(54) HEAT SHOCK PROTEIN-BINDING PEPTIDE COMPOSITIONS AND METHODS OF USE THEREOF

(71) Applicant: Agenus Inc., Lexington, MA (US)

(72) Inventors: Mark Arthur Findeis, Belmont, MA (US); Benjamin Maxime Morin, Somerville, MA (US); Bishnu Joshi, Lexington, MA (US)

(73) Assignee: AGENUS INC., Lexington, MA (US)

( * ) Notice: Subject to any disclaimer, the term of this patent is extended or adjusted under 35 U.S.C. 154(b) by 0 days.

(21) Appl. No.: 16/394,812

(22) Filed: Apr. 25, 2019

(65) Prior Publication Data

US 2020/0000905 A1 Jan. 2, 2020

Related U.S. Application Data

(60) Provisional application No. 62/663,083, filed on Apr. 26, 2018, provisional application No. 62/692,009, filed on Jun. 29, 2018.

(51) Int. Cl.
| | |
|---|---|
| A61K 47/64 | (2017.01) |
| A61K 39/00 | (2006.01) |
| C07K 7/06 | (2006.01) |
| C07K 19/00 | (2006.01) |
| A61K 47/69 | (2017.01) |
| A61K 39/12 | (2006.01) |
| C07K 14/47 | (2006.01) |

(52) U.S. Cl.
CPC ...... *A61K 39/001114* (2018.08); *A61K 39/12* (2013.01); *A61K 47/646* (2017.08); *A61K 47/6901* (2017.08); *C07K 7/06* (2013.01); *C07K 14/47* (2013.01); *A61K 2039/5152* (2013.01); *A61K 2039/6043* (2013.01); *A61K 2039/622* (2013.01); *A61K 2039/627* (2013.01); *A61K 2039/64* (2013.01); *C07K 2319/70* (2013.01)

(58) Field of Classification Search
CPC .......... A61K 47/646; A61K 2039/6043; A61K 2039/62; A61K 2039/622; A61K 2039/627; A61K 2039/64; C07K 7/06; C07K 2319/70
See application file for complete search history.

(56) References Cited

U.S. PATENT DOCUMENTS

| | | |
|---|---|---|
| 4,690,915 A | 9/1987 | Rosenberg et al. |
| 4,761,470 A | 8/1988 | Emini et al. |
| 5,188,964 A | 2/1993 | Mcguire et al. |
| 5,232,833 A | 8/1993 | Sanders et al. |
| 5,288,639 A | 2/1994 | Burnie et al. |
| 5,348,945 A | 9/1994 | Berberian et al. |
| 5,652,115 A | 7/1997 | Marks et al. |
| 5,750,119 A | 5/1998 | Srivastava et al. |
| 5,830,464 A | 11/1998 | Srivastava et al. |
| 5,837,251 A | 11/1998 | Srivastava et al. |
| 5,935,576 A | 8/1999 | Srivastava et al. |
| 5,948,646 A | 9/1999 | Srivastava et al. |
| 5,961,979 A | 10/1999 | Srivastava et al. |
| 5,985,270 A | 11/1999 | Srivastava et al. |
| 5,997,873 A | 12/1999 | Srivastava et al. |
| 6,007,821 A | 12/1999 | Srivastava et al. |
| 6,017,540 A | 1/2000 | Srivastava et al. |
| 6,030,618 A | 2/2000 | Srivastava et al. |
| 6,037,135 A | 3/2000 | Kubo et al. |
| 6,231,859 B1 | 5/2001 | Kensil et al. |
| 6,383,494 B1 | 5/2002 | Srivastava et al. |
| 6,387,374 B1 | 5/2002 | Srivastava et al. |
| 6,406,700 B1 | 6/2002 | Srivastava et al. |
| 6,410,026 B1 | 6/2002 | Srivastava et al. |
| 6,410,027 B1 | 6/2002 | Srivastava et al. |
| 6,410,509 B1 | 6/2002 | Triebel et al. |
| 6,436,404 B1 | 8/2002 | Srivastava et al. |
| 6,451,316 B1 | 9/2002 | Srivastava et al. |
| 6,475,490 B1 | 11/2002 | Srivastava et al. |
| 6,572,860 B1 | 6/2003 | Zimmerman et al. |
| 6,645,495 B1 | 11/2003 | Kensil et al. |
| 6,663,868 B1 | 12/2003 | Rothman et al. |
| 6,984,389 B2 | 1/2006 | Li et al. |
| 7,105,162 B1 | 9/2006 | Schmidt et al. |
| 7,132,109 B1 | 11/2006 | Srivastava et al. |

(Continued)

FOREIGN PATENT DOCUMENTS

| | | |
|---|---|---|
| DE | 19602985 A1 | 7/1997 |
| EP | 0859631 B1 | 8/1998 |

(Continued)

OTHER PUBLICATIONS

Butler et al. Evolution of pathogenicity and sexual reproduction in eight Candida genomes. Nature. Jun. 4, 2009, vol. 459, pp. 657-662. (Year: 2009).*

Gillen et al. Molecular Cloning and Functional Expression of the K—Cl Cotransporter from Rabbit, Rat, and Human. The Journal of Biological Chemistry. Jul. 5, 1996, vol. 271, No. 27, pp. 16237-16244. (Year: 1996).*

(Continued)

*Primary Examiner* — Jeffrey E. Russel
(74) *Attorney, Agent, or Firm* — Dechert LLP; Andrew T. Wilkins

(57) ABSTRACT

Provided are polypeptides and compositions comprising novel HSP-binding peptides. Such polypeptides and compositions are particularly useful as immunotherapeutics (e.g., cancer vaccines). Also provided are methods of inducing a cellular immune response using such polypeptides and compositions, methods of treating a disease using such polypeptides and compositions, kits comprising such polypeptides and compositions, and methods of making such compositions.

43 Claims, 14 Drawing Sheets

Specification includes a Sequence Listing.

(56) References Cited

U.S. PATENT DOCUMENTS

| | | | |
|---|---|---|---|
| 7,186,515 B1 | 3/2007 | Srivastava et al. | |
| 7,309,491 B2 | 12/2007 | Slusarewicz et al. | |
| 7,420,037 B2 | 9/2008 | Slusarewicz et al. | |
| 7,601,359 B1 | 10/2009 | Srivastava et al. | |
| 7,666,581 B2 | 2/2010 | Srivastava et al. | |
| 7,811,828 B2 | 10/2010 | Lemmel et al. | |
| 7,998,486 B2 | 8/2011 | Mautino et al. | |
| 8,029,808 B2 | 10/2011 | Srivastava et al. | |
| 8,140,270 B2 | 3/2012 | Kingsmore et al. | |
| 8,349,558 B2 | 1/2013 | Fatho et al. | |
| 8,372,393 B2 | 2/2013 | Kündig et al. | |
| 8,541,002 B2 | 9/2013 | Truneh et al. | |
| 8,591,890 B2 | 11/2013 | Srivastava et al. | |
| 8,877,204 B2 | 11/2014 | Srivastava et al. | |
| 8,926,961 B2 * | 1/2015 | Nakagawa | C07K 14/005 424/93.5 |
| 9,115,402 B2 | 8/2015 | Hacohen et al. | |
| 9,186,418 B2 | 11/2015 | Cohen et al. | |
| 9,248,172 B2 | 2/2016 | Srivastava et al. | |
| 9,352,019 B2 | 5/2016 | Srivastava et al. | |
| 9,783,849 B2 | 10/2017 | Weinschenk et al. | |
| 9,791,443 B2 | 10/2017 | Weinschenk et al. | |
| 2001/0034042 A1 | 10/2001 | Srivastava et al. | |
| 2002/0044948 A1 | 4/2002 | Khleif et al. | |
| 2006/0079458 A1 | 4/2006 | Srivastava et al. | |
| 2006/0093612 A1 | 5/2006 | Srivastava et al. | |
| 2009/0208450 A1 | 8/2009 | Yang et al. | |
| 2009/0280511 A1 | 11/2009 | Yahara et al. | |
| 2011/0287057 A1 | 11/2011 | Podack et al. | |
| 2012/0059670 A1 | 3/2012 | Sanborn et al. | |
| 2012/0100173 A1 | 4/2012 | Leclair et al. | |
| 2012/0142894 A1 | 6/2012 | Kosmatopoulos et al. | |
| 2012/0208706 A1 | 8/2012 | Downing et al. | |
| 2013/0230591 A1 * | 9/2013 | Fellous | A61P 35/00 424/474 |
| 2014/0105854 A1 | 4/2014 | Truneh et al. | |
| 2014/0178438 A1 | 6/2014 | Sahin et al. | |
| 2015/0079119 A1 | 3/2015 | Johnston et al. | |
| 2015/0110821 A1 | 4/2015 | Saint-remy et al. | |
| 2015/0140041 A1 | 5/2015 | Vitiello et al. | |
| 2015/0178445 A1 | 6/2015 | Cibulskis et al. | |
| 2015/0205911 A1 | 7/2015 | Aswad et al. | |
| 2015/0232525 A1 | 8/2015 | Durrant et al. | |
| 2015/0252427 A1 | 9/2015 | Srivastava et al. | |
| 2015/0315247 A1 | 11/2015 | Binder et al. | |
| 2015/0320848 A1 | 11/2015 | Rammensee et al. | |
| 2016/0045594 A1 | 2/2016 | Geraghty et al. | |
| 2016/0132631 A1 | 5/2016 | Bremel et al. | |

FOREIGN PATENT DOCUMENTS

| | | | |
|---|---|---|---|
| EP | | 1117421 B2 | 7/2001 |
| EP | | 1126872 B1 | 8/2001 |
| EP | | 1787654 B1 | 5/2007 |
| EP | | 1879612 B1 | 1/2008 |
| EP | | 2111867 B1 | 10/2009 |
| EP | | 2129389 B1 | 12/2009 |
| EP | | 2374814 A2 | 12/2011 |
| EP | | 2752198 A1 | 7/2014 |
| WO | WO 1997/006685 A1 | | 2/1997 |
| WO | WO 1997/010000 A1 | | 3/1997 |
| WO | WO 1997/030721 A1 | | 8/1997 |
| WO | WO 1998/014207 A1 | | 4/1998 |
| WO | WO 1999/022761 A1 | | 5/1999 |
| WO | WO 1999/047641 A1 | | 9/1999 |
| WO | WO 2000/009159 A1 | | 2/2000 |
| WO | WO 2001/052791 A2 | | 7/2001 |
| WO | WO 2001/063278 A2 | | 8/2001 |
| WO | WO 2001/078655 A2 | | 10/2001 |
| WO | WO 2001/078772 A1 | | 10/2001 |
| WO | WO 2001/079259 A1 | | 10/2001 |
| WO | WO 2001/091787 A1 | | 12/2001 |
| WO | WO 2003/015712 A2 | | 2/2003 |
| WO | WO 2003/062262 A2 | | 7/2003 |
| WO | WO 2003/072595 A2 | | 9/2003 |
| WO | WO 2003/090686 A2 | | 11/2003 |
| WO | WO-2004007527 A2 * | | 1/2004 ........... C07K 5/0827 |
| WO | WO 2004/033657 A2 | | 4/2004 |
| WO | WO 2004/071457 A2 | | 8/2004 |
| WO | WO 2004/075636 A1 | | 9/2004 |
| WO | WO 2004/091493 A2 | | 10/2004 |
| WO | WO 2005/028496 A2 | | 3/2005 |
| WO | WO 2007/101227 A3 | | 9/2007 |
| WO | WO 2008/031126 A1 | | 3/2008 |
| WO | WO 2008/035350 A1 | | 3/2008 |
| WO | WO 2010/115118 A3 | | 10/2010 |
| WO | WO 2011/149909 A2 | | 12/2011 |
| WO | WO 2012/126118 A1 | | 9/2012 |
| WO | WO 2012/159643 A1 | | 11/2012 |
| WO | WO 2012/159754 A2 | | 11/2012 |
| WO | WO 2013/074058 A1 | | 5/2013 |
| WO | WO 2013/158611 A1 | | 10/2013 |
| WO | WO 2013/177593 A2 | | 11/2013 |
| WO | WO 2014/039675 A2 | | 3/2014 |
| WO | WO 2014/093855 A1 | | 3/2014 |
| WO | WO 2014/036562 A2 | | 6/2014 |
| WO | WO 2014/082729 A9 | | 6/2014 |
| WO | WO 2014/168874 A2 | | 10/2014 |
| WO | WO 2014/180490 A1 | | 11/2014 |
| WO | WO 2015/013461 A2 | | 1/2015 |
| WO | WO 2015/014375 A1 | | 2/2015 |
| WO | WO 2015/085233 A1 | | 6/2015 |
| WO | WO 2015/095811 A2 | | 6/2015 |
| WO | WO 2015/103037 A2 | | 7/2015 |
| WO | WO 2016/040110 A1 | | 3/2016 |
| WO | WO 2016/040900 A1 | | 3/2016 |
| WO | WO 2017/091333 A1 | | 6/2017 |

OTHER PUBLICATIONS

"Agenus Vaccine Shows Significant Reduction in Viral Burden after HerpV Generated Immune Activation," Agenus Press Release issued Jun. 26, 2014 (last accessed Mar. 28, 2018 at investor.agenusbio.com/2014-06-20-Agenus-Vaccine-Shows-Significant-Reduction-in-Viral-Burden-after-HerpV-Generated-Immune-Activation).

Castellino et al. (2000) "Receptor-mediated Uptake of Antigen/Heat Shock Protein Complexes Results in Major Histocompatibility Complex Class I Antigen Presentation via Two Distinct Processing Pathways," J Exp Med 91(11):1957-64.

"Cell Genesys Crushed on Latest GVAX Failure; Seeking Options" published online by BioWorld on Oct. 17, 2008 (last accessed Mar. 22, 2018 at www.bioworld.com/content/cell-genesys-crushed-latest-gvax-failure-seeking-options).

"GSK's candidate shingles vaccine demonstrates 90% efficacy against shingles in people 70 years of age and over," GSK news release from Oct. 27, 2015 (last accessed on Mar. 23, 2018 at www.gsk.com/en-gb/media/press-releases/gsk-s-candidate-shingles-vaccine-demonstrates-90-efficacy-against-shingles-in-people-70-years-of-age-and-over/).

[No Author Listed] (2005) "Abstracts from the IV International Conference on heat shock proteins in immune response. Farmington, Connecticut, USA. Oct. 10-13, 2004," Immunology 114(1):141-54.

"Agenus acquires PhosImmune with a novel class of cancer neoantigens," Agenus press release issued Dec. 23, 2015 (last accessed on Mar. 29, 2018 at investor.agenusbio.com/2015-12-23-Agenus-Acquires-PhosImmune-with-a-Novel-Class-of-Cancer-Neoantigens).

"Agenus announces Phase 2 checkpoint inhibitor combination trial with Prophage cancer vaccine for melanoma," Press Release issued Jan. 14, 2014 (last accessed Mar. 28, 2018 at investor.agenusbio.com/2014-01-14-Agenus-Announces-Phase-2-Checkpoint-inhibitor-Combination-Trial-with-Prophage-Cancer-Vaccine-for-Melanoma).

"Agenus brain cancer vaccine shows extended survival in Phase 2 Final Data Analysis," Agenus Press Release Issued Jul. 1, 2014 (last accessed Mar. 28, 2018 at investor.agenusbio.com/2014-07-01-Agenus-Brain-Cancer-Vaccine-Shows-Extended-Survival-in-Phase-2-Final-Data-Analysis).

(56) References Cited

OTHER PUBLICATIONS

"Disappointing Results for Melacine" online publication by PharmaLetter on Oct. 7, 1994 (last accessed Mar. 22, 2018 at www.thepharmaletter.com/article/dissapointing-results-for-melacine).
"GlaxoSmithKline shutters lung cancer vaccine study on latest MAGE-A3 setback", published online Apr. 2, 2014 by FierceBiotech (last accessed Mar. 22, 2018 at www.fiercebiotech.com/r-d/glaxosmithkline-shutters-lung-cancer-vaccine-study-on-latest-mage-a3-setback).
"GSK's malaria vaccine phase 3 study containing Agenus' QS-21 published in The Lancet," Agenus Press Release issued Apr. 24, 2015 (last accessed Mar. 28, 2018 at investor.agenusbio.com/2015-04-24-GSK-s-Malaria-Vaccine-Phase-3-Study-Containing-Agenus-QS-21-Published-in-The-Lancet).
"Positive outcome of phase 3 study of GSK shingles vaccine containing Agenus adjuvant," Agenus Press Release issued Dec. 18, 2014 (last accessed Mar. 28, 2018 at investor.agenusbio.com/2014-12-18-Positive-Outcome-of-Phase-3-Study-of-GSK-Shingles-Vaccine-Containing-Agenus-Adjuvant).
Aalamian, M. et al. (2006) "Autologous renal cell cancer vaccines using heat shock protein-peptide complexes," Urologic Oncology. 24(5):425-433.
Agenus Presentation [Untitled] given at Rodman & Renshaw Annual Global Investment Conference, New York City, NY, on Sep. 8-10, 2015.
Agenus Presentation, "A Comprehensive Immuno-oncology Ecosystem," given at Cowen and Co. 36th Annual Health Care Conference on Mar. 7, 2016.
Agenus Presentation, "Agenus R&D Day" given in New York City, NY on Nov. 19, 2015.
Agenus Presentation, "Agenus R&D Day," given on May 14, 2015.
Agenus Presentation, "Antibodies in Drug Discovery," given in Cambridge, UK on Feb. 10, 2016.
Agenus Presentation, "Corporate Presentation," given Feb. 2014.
Agenus Presentation, "Emerging Leader in Immuno-oncology", given on Jan. 6, 2016.
Agenus Presentation, "Individualized Cancer Immunotherapies," given on Jan. 20, 2016.
Agenus Presentation, "Integrated Approach to Immuno-Oncology" given in New York City, NY on Mar. 31, 2016.
Agenus Presentation, "Integrated Solutions in Immuno-Oncology," given to Jefferies on Apr. 7, 2016.
Agenus Presentation, "Spotlight on effective antigens for immune education," given at World Vaccine Congress on Apr. 8, 2015.
Agenus Roadshow Slide Deck dated May 15, 2015.
Agenus Slide Deck for Immunotherapy Conference Talk (NY) dated Mar. 31, 2016.
Agenus Slide Deck for RBS Immunotherapy Conference Talk (NY) dated Mar. 27, 2014.
Agnandji et al. (2011) "First Results of Phase 3 Trial of RTS,S/AS01 Malaria Vaccine in African Children," N Engl J Med 365(20):1863-75.
Altmeyer, A. et al. (1996) "Tumor-specific cell surface expression of the-KDEL containing, endoplasmic reticular heat shock protein gp96," Int J Cancer. 69(4):340-9.
Anderson, KM (2000) "Heat, heat shock, heat shock proteins and death: a central link in innate and adaptive immune responses," Immunol Lett. 74(1):35-9.
Anderson, S. et al. (1994) "The endoplasmic reticular heat shock protein gp96 is transcriptionally upregulated in interferon-treated cells," J. Exp. Med. 1980:1565-1569.
Arnold et al. (1997) "Influences of Transporter Associated with Antigen Processing (TAP) on the Repertoire of Peptides Associated with the Endoplasmic Reticulum-resident Stress Protein gp96," J Exp Med 186(3):461-6.
Auger et al. (1996) "HLA-DR4 and HLA-DR10 motifs that carry susceptibility to rheumatoid arthritis bind 70-kD heat shock proteins," Nat. Med. 2(3):306-10.

Barrios et al. (1992) "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming," Eur. J. Immunol. 22(6):1365-72.
Bartkowiak et al. (2015) "Unique potential of 4-1BB agonist antibody to promote durable regression of HPV+ tumors when combined with an E6/E7 peptide vaccine," Proc Natl Acad Sci U S A 112(38):E5290-9.
Basu et al. (1999) "Calreticulin, a peptide-binding chaperone of the endoplasmic reticulum, elicits tumor- and peptide-specific immunity," J. Exp. Med. 189(5):797-802.
Basu et al. (2000) "Necrotic but not apoptic cell death releases heat shock proteins, which deliver a partial maturation signal to dendritic cells and activate the NF-xB pathway" Int Immunol. 12:1539-1546.
Basu et al. (2001) "CD91 Is a Common Receptor for Heat Shock Proteins gp96, hsp90, hsp70, and Calreticulin" Immunity 14:303-313.
Basu, S. (2003) "Fever-like temperature induces maturation of dendritic cells through induction of hsp90," Int Immunol. 15(9):1053-61.
Basu, S. et al. (2000) "Heat shock proteins: the fountainhead of innate and adaptive immune responses," Cell Stress Chaperones. 5(5):443-51.
Bauer et al., "Harnessing chaperone-mediated autophagy for the selective degradation of mutant huntingtin protein", Nature Biotechnology, vol. 28, No. 3, Feb. 28, 2010 (Feb. 28, 2010), pp. 256-263.
Bekri et al. "Preclinical study of a mutations based-vaccine for multiple myeloma immunotherapy," abstract to poster for Multiple Myeloma Workshop, Boston, MA, published on May 5, 2016.
Bekri et al. "Preclinical study of a mutations based-vaccine for multiple myeloma immunotherapy," poster presented at Multiple Myeloma Workshop, Boston, MA on May 5, 2016.
Bensaude et al. (1983) "Spontaneous high expression of heat-shock proteins in mouse embryonal carcinoma cells and ectoderm from day 8 mouse embryo," EMBO J. 2:173-177.
Berd et al. (2004) "Immunopharmacologic Analysis of an Autologous, Hapten-Modified Human Melanoma Vaccine" J Clin Oncol 22:403-415.
Binder et al. (2001) "Heat Shock Protein-chaperoned Peptides but Not Free Peptides Introduced into the Cytosol Are Presented Efficiently by Major Histocompatibility Complex I Molecules," J Biol Chem 276(20):17163-71.
Binder et al. (2005) "Peptides chaperoned by heat-shock proteins are a necessary and sufficient source of antigen in the cross-priming of CD8+ T cells," Nat Immunol 6(6):593-9.
Binder et al. (2014) "Functions of Heat Shock Proteins in Pathways of the Innate and Adaptive Immune System," J Immunol 193:5765-5771.
Binder, RJ (2000) "Saturation, competition, and specificity in interaction of heat shock proteins (hsp) gp96, hsp90, and hsp70 with CD11 b+ cells," J Immunol. 165(5):2582-7.
Binder, RJ (2004) "Essential role of CD91 in re-presentation of gp96-chaperoned peptides," Proc Natl Acad Sci U.S.A. 101(16):6128-33.
Binder, RJ et al. (2000) "CD91: a receptor for heat shock protein gp96," Nat Immunol. 1(2):151-5.
Binder, RJ et al. (2000) "Cutting edge: heat shock protein gp96 induces maturation and migration of CD11c+ cells in vivo," J Immunol. 165(11):6029-35.
Binder, RJ et al. (2001) "Adjuvanticity of alpha 2-macroglobulin, an independent ligand for the heat shock protein receptor CD91," J Immunol. 166(8):4968-72.
Binder, RJ et al. (2002) "Naturally formed or artificially reconstituted non-covalent alpha2-macroglobulin-peptide complexes elicit CD91-dependent cellular immunity," Cancer Immunology Research. 2(1):1-9.
Binder, RJ et al. (2007) "Specific immunogenicity of heat shock protein gp96 derives from chaperoned antigenic peptides and not from contaminating proteins," J Immunol. 179(11):7254-61.
Blachere et al. (1993) "Heat shock protein vaccines against cancer," J Immunotherapy 14:352-356.

(56) References Cited

OTHER PUBLICATIONS

Blachere et al. (1993) "Immunization with GP96 heat shock proteins isolated from tumors or influenza virus infected cells elicits MHC-restricted, antigen-specific cytotoxic T lymphocytes against the corresponding cells/antigens," J Cell Biochem. 17D:124 Abstract NZ 502.
Blachere et al. (1997) "Heat Shock Protein-Peptide Complexes, Reconstituted in Vitro, Elicit Peptide-specific Cytotoxic T Lymphocyte Response and Tumor Immunity," J Exp Med. 186(8):1315-22.
Blachere, NE et al. (1995) "Heat shock protein-based cancer vaccines and related thoughts on immunogenicity of human tumors," Semin Cancer Biol. 6(6):349-55.
Blachere, NE et al. (1997) "Heat shock protein-peptide complexes, reconstituted in vitro, elicit peptide-specific cytotoxic T lymphocyte response and tumor immunity," J Exp Med. 186(8):1315-22.
Boegel et al. (2014) "A catalog of HLA type, HLA expression. and neoepitope candidates in human cancer cell lines" Oncoimmunology 3(8):e954893, p. 2, left-hand column, paragraph 2; and p. 10, left-hand column, paragraph 2.
Boon (1992) "Toward a genetic analysis of tumor rejection antigens," Adv. in Cancer Res. 58:177-210.
Buckwalter et al. (2008) "It is the antigen(s), stupid and other lessons from over a decade of vaccitherapy of human cancer," Semin Immunol 20(5):296-300.
Buczynski et al. (2001) "Characterization of a Lidless Form of the Molecular Chaperone DnaK," J Biol Chem 276:27231-27236.
Bukau et al. (1998) "The Hsp70 and Hsp60 Chaperone Machines" Cell 92:351-366.
Burkholder et al. (1996) "Mutations in the C-terminal fragment of DnaK affecting peptide binding," Proc Natl Acad Sci U S A. 93(20):10632-7.
Callahan, MK (2006) "Heat shock up-regulates Imp2 and Imp7 and enhances presentation of immunoproteasome-dependent epitopes," Immunol. 177(12):8393-9.
Callahan, MK et al. (2008) "Heat-shock protein 90 associates with N-terminal extended peptides and is required for direct and indirect antigen presentation," Proc Natl Acad Sci U.S.A. 105(5):1662-7.
Carreno et al. (2015) "A dendritic cell vaccine increases the breadth and diversity of melanoma neoantigen-specific T cells," Science 348(6236):803-8.
Castelli, C. (2004) "Heat shock proteins: biological functions and clinical application as personalized vaccines for human cancer," Cancer Immunol Immunother. 53(3):227-33.
Castle et al. (2012) "Exploiting the Mutanome for Tumor Vaccination," Cancer Res. 72(5):1081-91.
Castle et al. (2014) "Immunomic, genomic and transcriptomic characterization of CT26 colorectal carcinoma," BMC Genomics 15:190.
Castle et al. (2014) "Mutated tumor alleles are expressed according to their DNA frequency," Sci Rep 4:4743.
Chandawarkar, RY (2004) "Immune modulation with high-dose heat-shock protein gp96: therapy of murine autoimmune diabetes and encephalomyelitis," Int Immunol. 16(4):615-24.
Ciupitu et al (1998) "Immunization with a Lymphocytic Choriomeningitis Virus Peptide Mixed with Heat Shock Protein 70 Results in Protective Antiviral Immunity and Specific Cytotoxic T Lymphocytes," J Exp Med 187:685-691.
Clarke et al. (1988) "Purification of complexes of nuclear oncogene p53 with rat and *Escherichia coli* heat shock proteins: in vitro dissociation of hsc70 and dnaK from murine p53 by ATP," Mol. Cell Biol. 8(3):12061215.
Cobbold et al. (2013) "MHC Class I—Associated Phosphopeptides Are the Targets of Memory-like Immunity in Leukemia," Sci Transl Med 5:203ra125.
Cohen (1993) "Cancer Vaccines Get a Shot in the Arm," Science 262:841-843.
Craig (1993) "Chaperones: helpers along the pathways to protein folding," Science 260(5116):1902-3.

Dahlstrom et al. (2003) "Human Papillomavirus Type 16 Infection and Squamous Cell Carcinoma of the Head and Neck in Never-Smokers: A Matched Pair Analysis1," Clin Can. Res 9:2620-2626.
Davidoff et al. (1992) "Immune response to p53 is dependent upon p53/HSP70 complexes in breast cancers," Proc. Natl. Acad. Sci. USA 89(8):3439-3442.
Dendouga et al. (2012) "Cell-mediated immune responses to a varicella-zoster virus glycoprotein E vaccine using both a TLR agonist and QS21 in mice," Vaccine 30:3126-3135 (Abstract Only).
Didierlaurent et al. (2014) "Enhancement of Adaptive Immunity by the Human Vaccine Adjuvant AS01 Depends on Activated Dendritic Cells," J Immunol 193:1920-30.
Diken et al. (2015) "Current Developments in Actively Personalized Cancer Vaccination with a Focus on RNA as the Drug Format," Prog. Tumor Res (Basel) 42:44-54.
Duan et al. (2014) "Genomic and bioinformatic profiling of mutational neoepitopes reveals new rules to predict anticancer immunogenicity" J Exp Med. 211(11):2231-48.
Duraiswamy et al. (2013) "Dual Blockade of PD-1 and CTLA-4 Combined with Tumor Vaccine Effectively Restores T-Cell Rejection Function in Tumors," Cancer Res 73:3591-3603.
Ebert et al. (2012) "A Cancer Vaccine Induces Expansion of NY-ESO-1-Specific Regulatory T Cells in Patients with Advanced Melanoma," PLoS One 7(10):e48424.
Elliot et al. (1990) "Naturally processed peptides," Nature 348:195-197.
Falk et al. (1990) "Cellular peptide composition governed by major histocompatibility complex class I Molecules," Nature 348:248-251.
Falk et al. (1991) "Allele-specific motifs revealed by sequencing of self-peptides eluted from mhc molecules," Nature 351:290-296.
Feldweg et al. (1993) "Evidence for biochemical heterogeneity of gp96 heat shock protein/tumor rejecion antigen," J Cell Biochem., Suppl. 17D:108.
Feldweg, AM et al. (1995) "Molecular heterogeneity of tumor rejection antigen/heat shock protein GP96," Int J Cancer. 63(2):310-4.
Filipazzi et al. (2008) "Adjuvant multipeptide vaccination in high-risk early melanoma patients" Journal of Clinical Oncology, 2008 ASCO Annual Meeting Proceedings (Post-Meeting Edition). vol. 26, No. 15S (May 20 Supplement).
Flechtner et al. (2006) "High-Affinity Interactions between Peptides and Heat Shock Protein 70 Augment CDS+ T Lymphocyte Immune Responses," J Immunol 177:1017-1027.
Flynn et al. (1989) "Peptide binding and release by proteins implicated as catalysts of protein assembly," Science 245(4916):385-90.
Flynn et al. (1991) "Peptide-binding specificity of the molecular chaperone BiP," Nature 353:726-730.
Francois et al. (2009) "The CD4+ T-Cell Response of Melanoma Patients to a MAGE-A3 Peptide Vaccine Involves Potential Regulatory T Cells," Cancer Res 69(10):4335-45.
Franklin (1993) "Making vaccines fit the cancer," New Scientist 140:17.
Fritsch et al. (2014) "HLA-Binding Properties of Tumor Neoepitopes in Humans," Cancer Immunol Res 2:522-529.
Garcia-Murillas et al. (2015) "Mutation tracking in circulating tumor DNA predicts relapse in early breast cancer," Sci Transl Med 7:302ra133.
Garcon et al. (2011) "Recent clinical experience with vaccines using MPL- and QS-21-containing Adjuvant Systems," Expert Rev. Vaccines 10:471-486.
Geng et al. (2006) "HSP70 vaccine in combination with gene therapy with plasmid DNA encoding sPD-1 overcomes immune resistance and suppresses the progression of pulmonary metastatic melanoma.," Int J Cancer 118:2657-2664 (Abstract Only).
Gething et al. (1992) "Protein folding in the cell," Nature 355(6355):33-45.
Gragerov et al. (1994) "Different peptide binding specificities of hsp70 family members," J Mol Biol. 241(2):133-5.
Gragerov et al. (1994) "Specificity of DnaK-peptide binding," J Mol Biol 235(3):848-54.

(56) References Cited

OTHER PUBLICATIONS

Grizenkova, J. et al. (2012) "Overexpression of the Hspa13 (Stch) gene reduces prion disease incubation time in mice," Proc Natl Acad Sci U.S.A. 109(34):13722-7.

Gubin et al. (2014) "Checkpoint blockade cancer immunotherapy targets tumour-specific mutant antigens," Nature 515:577-581.

Gullo et al. (2004) "Heat shock proteins: to present or not, that is the question," Immunol. Lett. 94(1-2):1-10.

Haberthur et al. (2011) "CD4 T Cell Immunity Is Critical for the Control of Simian Varicella Virus Infection in a Nonhuman Primate Model of VZV Infection," PLOS Pathogens, 7(11):e1002367, pp. 1-16.

Halevy et al. (1990) "Different tumor-derived p53 mutants exhibit distinct biological activities," Science 250(4977):113-116.

Henderson et al (2010) " Caught with their PAMPs down? The extracellular signaling actions of molecular chaperones are not due to microbial contaminants," Cell Stress and Chaperones 15:123-141.

Hinds et al. (1987) "Immunological evidence for the association of p53 with a heat shock protein, hsc70, in p53-plus-ras-transformed cell lines," Mol. Cell. Biol. 7(8):2863-2869.

Hinds et al. (1990) "Mutant p53 DNA clones from human colon carcinomas cooperate with ran in transforming primary rat cells: a comparison of the "hot spot" mutant phenotypes," Cell Growth Differ. 1(12):571-580.

Hoos et al. (2003) "Vaccination with Heat Shock Protein-Peptide Complexes: From Basic Science to Clinical Applications." Expert Rev. Vaccines 2:369-379.

International Search Report and Written Opinion received for PCT Patent Application No. PCT/US19/29112, dated Nov. 20, 2019, 18 pages.

International Search Report with Written Opinion corresponding to International Patent Application No. PCT/US2016/032465, dated Sep. 13, 2016, 17 pages.

Ishii et al. (1999) "Isolation of MHC Class I-Restricted Tumor Antigen Peptide and Its Precursors Associated with Heat Shock Proteins hsp70, hsp90, and gp96," J Immunol 162:1303-1309.

Jakob et al. (1993) "Small heat shock proteins are molecular chaperones," J. Biol. Chem. 268(3):1517-1520.

Janetzki, S. (1998) "Generation of tumor-specific cytotoxic T lymphocytes and memory T cells by immunization with tumor-derived heat shock protein gp96," J Immunother. 21(4):269-76.

Janetzki, S. (2000) "Immunization of cancer patients with autologous cancer-derived heat shock protein gp96 preparations: a pilot study," Int J Cancer. 88(2):232-8.

Jardetsky et al. (1991) "Identification of self peptides bound to purified HLA-B27," Nature 353:326-329.

Jindal et al. (1992) "Vaccinia virus infection induces a stress response that leads to association of Hsp70 with viral proteins," J. Virol. 66(9):5357-62.

Jing. et al. (2012) "Cross-presentation and genome-wide screening reveal candidate T cells antigens for a herpes simplex virus type 1 vaccine," J Clin Invest. 1-20.

Jocham et al. (2004) "Adjuvant autologous renal tumour cell vaccine and risk of tumour progression in patients with renal-cell carcinoma after radical nephrectomy: phase III, randomised controlled trial," Lancet 363:594-599.

Johnston. et al. (2011) "HSV-2: in pursuit of a vaccine," J Clin Investigation, 121(12):4600-4609.

Kensil, CR et al. (2004) "Current vaccine adjuvants: an overview of a diverse class," Front Biosci. 9:2972-88.

Kocsis et al. (2002) "Antibodies against the human heat shock proteni hsp70 in pateints with severe coronary artery disease," Immunol Invest 31:219-231.

Kovalchin et al. (2001) "Determinants of efficacy of immunotherapy with tumor-derived heat shock protein gp96," Cancer Immun 1:7.

Kovalchin, J. et al. (2001) "Determinants of efficacy of immunotherapy with tumor-derived heat shock protein gp96," Cancer Immunology Research. 1(1):7.

Kovalchin, JT et al. (2006) "In vivo delivery of heat shock protein 70 accelerates wound healing by up-regulating macrophage-mediated phagocytosis," Wound Repair Regen. 14(2):129-37.

Kovalchin, JT et al. (2006) "In vivo treatment of mice with heat shock protein, gp 96, improves survival of skin grafts with minor and major antigenic disparity," Transpl Immunol. 15(3):179-85.

Kreiter et al. (2015) "Mutant MHC class II epitopes drive therapeutic immune responses to cancer," Nature 520:692-696 with Erratum Kreiter et al. (2015) Nature 523:370.

Kumaraguru et al. (2002) "Immunization with Chaperone-Peptide Complex Induces Low-Avidity Cytotoxic T Lymphocytes Providing Transient Protection Against Herpes Simplex Virus Infection"; Journal of Virology, Jan. 2002, p. 136-141.

Kumaraguru et al. (2004) "Concomitant Helper Response Recues Otherwise Low Avidity CD8+ Memory CTLs to Become Efficient Effectors In Vivo," J Immunol 172:3719-3724.

Lakey et al. (1987) "Identification of a peptide binding protein that plays a role in antigen presentation," Proc. Natl. Acad. Sci. USA 84:1659-1663.

Lammert et al. (1997) "Protein disulfide isomerase is the dominant acceptor for peptides translocated into the endoplasmic reticulum," Eur J Immunol 27: 1685-1690.

Lennerz et al. (2005) "The response of autologous T cells to a human melanoma is dominated by mutated neoantigens," Proc Natl Acad Sci U S A 102(44):16013-8.

Levy (1991) "ATP is required for in vitro assembly of mhc class I antigens but not for transfer of peptides across the membrane," Cell 67:265-274.

Li et al. (1993) "Tumor rejection antigen gp96/grp94 is an ATPase: implications for protein folding and antigen presentation," EMBO J. 12(8):3143-51.

Li, C. et al. (2012) "Dendritic cells sequester antigenic epitopes for prolonged periods in the absence of antigen-encoding genetic information," Proc Natl Acad Sci U.S.A. 109(43):17543-8.

Li, Z. et al. (1994) "A critical contemplation on the role of heat shock proteins in transfer of antigenic peptides during antigen presentation," Behring Inst Mitt.(94):37-47.

Lin et al. (1993) "The 170-kDa glucose-regulated stress protein is an endoplasmic reticulum protein that binds immunoglobulin," Mol. Biol. Cell 4(11):1109-19.

Lindquist (1986) "The Heat-Shock Response," Ann Rev Biochem 55:1151-91.

Lindquist et al. (1988) "The heat-shock proteins," Annu. Rev. Genet. 22:631-77.

Luescher et al. (1991) "Specific binding of antigenic peptides to cell-associated mhc class I molecules," Nature 351:72-77.

Lukacs et al. (1993) "Tumor cells transfected with a bacterial heat-shock gene lose tumorigenicity and induce protection against tumors," J. Exp. Med. 178:343-348.

Lussow et al. (1991) "Mycobacterial heat-shock proteins as carrier molecules," Eur. J. Immunol. 21:2297-2302.

Lyngaa et al. (2014) "T-cell Responses to Oncogenic Merkel Cell Polyomavirus Proteins Distinguish Patients with Merkel Cell Carcinoma from Healthy Donors," Clin Cancer Res 20(7):1768-1778.

Macary et al. (2004) "HSP70 Peptide Binding Mutants Separate Antigen Delivery from Dendritic Cell Stimulation," Immunity 20(1):95-106.

Macejak et al. (1992) "Association of heat shock protein 70 with enterovirus capsid precursor P1 in infected human cells," J. Virol. 66(3):1520-7.

Madden et al. (1991) "The structure of hla-b27 reveals nonamer self-peptides bound in an extended conformation," Nature 353:321-325.

Maki (1991) "The Human Homologue of the Mouse Tumor Rejection Antigen GP96," Ph.D. thesis, Cornell University.

Maki et al. (1990) "Human homologue of murine tumor rejection antigen gp96: 5'-Regulatory and coding regions and relationship to stress-induced proteins," Proc. Natl. Acad. Sci. USA 87(15):5658-5663.

Maki et al. (1993) "Mapping of the Genes for Human Endoplasmic Reticular Heat Shock Protein gp96/grp94," Somatic Cell Mol. Genetics 19(1):73-81.

(56) References Cited

OTHER PUBLICATIONS

Maki, RG et al. (2007) "A phase I pilot study of autologous heat shock protein vaccine HSPPC-96 in patients with resected pancreatic adenocarcinoma," Dig Dis Sci. 52(8):1964-72.
Martin, J. et al. (1993) "The reaction cycle of GroEL and GroES in chaperonin-assisted protein folding," Nature. 366(6452):228-33.
Marty-Roix et al. "Identification of QS-21 as an Inflammasome-activating Molecular Component of Saponin Adjuvants," (2016) J Biol Chem 291(3):1123-36.
Mateo et al. (1999) "An HLA-A2 Polyepitope Vaccine for Melanoma Immunotherapy," J Immunol 163:4058-4063.
Mazzaferro, V. (2003) "Vaccination with autologous tumor-derived heat-shock protein gp96 after liver resection for metastatic colorectal cancer," Clin Cancer Res. 9(9):3235-45.
McCall et al. (1989) "Biotherapy: A New Dimension in Cancer Treatment," Biotechnology 7:231-240.
McGeoch et al. (1987) "DNA sequence and genetic content of the HindIII I region in the short unique component of the herpes simplex virus type 2 genome: identification of the gene encoding glycoprotein G, and evolutionary comparisons," J Gen Virol 68:19-38.
Melief et al. "Effective therapeutic anticancer vaccines based on precision guiding of cytolytic T lymphocytes," (2002) Immunol Rev 188:177-82.
Ménoret A. (1999) "Association of peptides with heat shock protein gp96 occurs in vivo and not after cell lysis," Biochem Biophys Res Commun. 262(3):813-8.
Ménoret, A. et al. (2000) "Natural autoantibodies against heat-shock proteins hsp70 and gp96: implications for immunotherapy using heat-shock proteins," Immunology. 101(3):364-70.
Mo et al. (2011) "A Heat Shock Protein Based Polyvalent Vaccine Targeting HSV-2: CD4+ and CD8+ Cellular Immunity and Protective Efficacy" Vaccine 29; 8350-8541.
Mo, A. et al. (2011) "A heat shock protein based polyvalent vaccine targeting HSV-2: CD4(+) and CD8(+) cellular immunity and protective efficacy," Vaccine. 29(47):8530-41.
Mohammed et al. (2008) "Phosphorylation-dependent interaction between antigenic peptides and MHC class I: a molecular basis for presentation of transformed self," Nat Immunol 9(11): 1236-1243.
Moroi et al. (2000) "Induction of cellular immunity by immunization with novel hybrid peptides complexed to heat shock protein 70," Proc. Natl. Acad. Sci. U. S. A. 97(7):3485-90.
Nelson et al. (1992) "The translation machinery and 70 kd heat shock protein cooperate in protein synthesis," Cell 71:97-105.
Nieland et al. (1996) "Isolation of an immunodominant viral peptide that is endogenously bound to the stress protein GP96/GRP94," Proc. Natl. Acad. Sci. USA 93:6135-6139.
Noguchi et al. (2008) "Immunologic and clinical effects of personalized selection of peptide vaccines in HLA-A2 positive patients with advanced cancer," Journal of Clinical Oncology, 2008 Asco Annual Meeting Proceedings (Post-Meeting Edition). vol. 26, No. 15S (May 20 Supplement), 2008: 3031.
Obara et al. (2010) "Phase I/II study of novel HLA-A24 restricted DEPDC1 and MPHOSPH1 peptide vaccine for bladder cancer," Journal of Clinical Oncology, 2010 ASCO Annual Meeting Abstracts, vol. 28, No. 15_suppl (May 20 Supplement).
Oki, Y. (2007) "Experience with heat shock protein-peptide complex 96 vaccine therapy in patients with indolent non-Hodgkin lymphoma," Cancer. 109(1):77-83.
Pack et al. (2008) "An intranasal heat shock protein based vaccination strategy confers protection against mucosal challenge with herpes simplex virus," Human Vaccines 4:360-364.
Panjwani, NN (2002) "Heat shock proteins gp96 and hsp70 activate the release of nitric oxide by APCs," J Immunol. 168(6):2997-3003.
Parmiani, G. et al. (2004) "Heat Shock Proteins and Their Use as Anticancer Vaccines," Clinical Cancer Research. 10(24):8142-8146.
Peng et al. (1997) "Purification of immunogenic heat shock protein 70-peptide complexes by ADP-affinity chromatography," J. Immunol. Methods 204(1):13-21.
Peng, P. (1997) "Purification of immunogenic heat shock protein 70-peptide complexes by ADP-affinity chromatography," J Immunol Methods. 204(1):13-21.
Phase I clinical trial NCT00683670 for Dendritic Cells (White Blood Cells) Vaccination for Advanced Melanoma by U. Penn. (published May 2008 and completed Jun. 2016) (last accessed on Mar. 22, 2018 at clinicaltrials.gov/ct2/show/NCT00683670?term=NCT00683670&rank=1).
Phase I clinical trial NCT01970358 for Personalized NeoAntigen Cancer Vaccine in Melanoma by Dana-Farber (last accessed on Mar. 22, 2018 at clinicaltrials.gov/ct2/show/NCT01970358?term=NCT01970358&rank=1).
Phase I clinical trial NCT02035956 for IVAC Mutanome by Biontech RNA Pharma (last accessed on Mar. 22, 2018 at clinicaltrials.gov/ct2/show/NCT02035956?term=NCT02035956&rank=1).
Phase I clinical trial NCT02149225 for GAPVAC Phase I Trial in Newly Diagnosed Glioblastoma Patients by Immatics Biotech. (first posted 2014) (last accessed on Mar. 22, 2018 at clinicaltrials.gov/ct2/show/NCT02149225?term=NCT02149225&rank=1).
Phase I clinical trial NCT02316457 for A-Immunotherapy of IVAC_W_bre1_uID and IVAC_M_uID (TNBC-MERIT) by Biontech AG (first posted Dec. 15, 2014) (last accessed on Mar. 22, 2018 at clinicaltrials.gov/ct2/show/NCT02316457?term=NCT02316457&rank=1).
Phase II clinical trial NCT02129075 for CDX-1401 and Poly-ICLC Vaccine Therapy With or Without CDX-301 in Treating Patients With Stage IIB-IV Melanoma by National Cancer Institute (published May 2, 2014) (last accessed on Mar. 22, 2018 at clinicaltrials.gov/ct2/show/NCT02129075?term=NCI+Phase+II+clinical+trial+for+stage+IIB-IV+melanoma+using+CDX-1401).
Pinhashi-Kimhi (1986) "Specific interaction between the p53 cellular tumour antigen and major heat shock proteins," Nature 320(6058):182-184.
Pockley et al. (1998) "Detection of heat shock protein 70 (HSP70) and anti-HSP70 . antibodies in the serum of normal individuals," Immunol Invest 27(6):367-77.
Pol et al. (2015) "Trial Watch: Peptide-based anticancer vaccines," Oncolmmunology 4:e974411.
Postow et al. (2015) "Immune Checkpoint Blockade in Cancer Therapy," J Clin Oncol 33(17):1974-82.
Przepiorka, D. (1998) "Heat shock protein-peptide complexes as immunotherapy for human cancer," Mol Med Today. 4(11):478-84.
Rapidis et al. (2009) "Immunotherapy of Head and Neck Cancer: Current and Future Considerations," J Oncol Article ID 346345.
Rea et al. (2001) "Serum heat shock protein and anti-heat shock protein antibody levels in aging," Exp Gerontol 36:341-352.
Rivoltini, L. (2003) "Human tumor-derived heat shock protein 96 mediates in vitro activation and in vivo expansion of melanoma- and colon carcinoma-specific T cells," J Immunol. 171(7):3467-74.
Robert et al. (2001) "Phylogenetic conservation of the molecular and immunological properties of the chaperones gp96 and hsp70," Eur J Immunol 31:186-195 (Abstract Only).
Robert, J. et al. (2001) "Immunological properties of heat shock proteins are phylogenetically conserved," Adv Exp Med Biol. 484:237-49.
Rotzschke et al. (1990) "Isolation and analysis of naturally processed viral peptides as recognized by Cytotoxic T cells", Nature 348:252-254.
Rudensky et al. (1991) "Sequence analysis of peptides bound to MHC class II molecules," Nature 353:622-627.
Salimu et al. (2015) "Cross-Presentation of the Oncofetal Tumor Antigen 5T4 from Irradiated Prostate Cancer Cells—A Key Role for Heat-Shock Protein 70 and Receptor CD91," Cancer Immunol Res 3:678-688.
Salk et al. (1993) "A strategy for prophylactic vaccination against HIV," Science 260:1270-1272.
Sato et al. (2001) "Immunotherapy using heat-shock protein preparations of leukemia cells after syngeneic bone marrow transplantation in mice," Blood 98:1852-1857.
Sawai et al. (1989) "Association of a cellular heat shock protein with simian virus 40 large T antigen in transformed cells," J. Virol. 63(9):3961-73.

(56) References Cited

OTHER PUBLICATIONS

Schadendorf et al. (2015) "Pooled Analysis of Long-Term Survival Data From Phase II and Phase III Trials of Ipilimumab in Unresectable or Metastatic Melanoma," J Clin Oncol 33:1889-1894.
Schlosser et al. (2007) "A novel cytosolic class I antigen-processing pathway for endoplasmic-reticulum-targeted proteins," EMBO Rep 8:945-951.
Schreiber et al. (2012) "T Cell Costimulation by TNFR Superfamily Vaccination (TNFRSF)4 and TNFRSF25 in the Context of Vaccination," J Immunol 189:3311-3318.
Schumacher et al. (1991) "Peptide selection by mhc class I molecules," Nature 350:703-706.
Schuster et al. (2011) "Vaccination With Patient-Specific Tumor-Derived Antigen in First Remission Improves Disease-Free Survival in Follicular Lymphoma," J Clin Oncol 29:2787-2794.
Sengupta, D. et al. (2004) "Heat shock protein-mediated cross-presentation of exogenous HIV antigen on HLA class I and class II," J Immunol. 173(3):1987-93.
Singh-Jasuja et al. (2007) "Correlation of T-cell response, clinical activity and regulatory T-cell levels in renal cell carcinoma patients treated with IMA901, a novel multi-peptide vaccine," J Clin Oncol 2007 ASCO Annual Meeting Proceedings (Post-Meeting Edition) (Abstract).
Snyder et al. (2014) "Genetic basis for clinical response to CTLA-4 blockade in melanoma," N Engl J Med 371(23):2189-2199.
Somersan et al. (2001) "Primary Tumor Tissue Lysates Are Enriched in Heat Shock Proteins and Induce the Maturation of Human Dendritic Cells1," J Immunol 4844-4852.
Sondermann, H. et al. (2000) "Characterization of a receptor for heat shock protein 70 on macrophages and monocytes," Biol Chem. 381(12):1165-74.
Srivastava (1991) "Protein tumor antigens," Curr. Opin. Immunol. 3:654-658.
Srivastava (1993) "Peptide-binding heat shock proteins in the endoplasmic reticulum: role in immune response to cancer and in antigen presentation," Adv. Cancer Res. 62:153-77.
Srivastava (1994) "Heat shock proteins in immune response to cancer: the fourth paradigm," Experientia. 50(11-12):1054-60.
Srivastava (2002) "Roles of heat-shock proteins in innate and adaptive immunity," Nat Rev Immunol. 2:185-194.
Srivastava et al. (1986) "Tumor rejection antigens of chemically induced sarcomas of inbred mice," Proc. Natl. Acad. Sci. U. S. A. 83(10):3407-11.
Srivastava et al. (1986) "Tumor-specific immunogenicity of stress-induced proteins: Convergence of two evolutionary pathways of antigen presentation?," Seminars in Immunol. 3:57-64.
Srivastava et al. (1987) "5'-Structural analysis of genes encoding polymorphic antigens of chemically induced tumors," Proc. Natl. Acad. Sci. USA 84:3807-3811.
Srivastava et al. (1988) "Chromosomal assignment of the gene encoding the mouse tumor rejection antigen gp96," Immunogenetics 28(3):205-7.
Srivastava et al. (1988) "Individually distinct transplantation antigens of chemically induced mouse tumors," Immunol. Today 9(3):78-83.
Srivastava et al. (1989) "Gp96 Molecules: Recognition Elements in Tumor Immunity," Human Tumor Antigens and Specific Tumor Therapy, pp. 63-71.
Srivastava et al. (1989) "Identification of a Human Homologue of the Murine Tumor Rejection Antigen GP96," Cancer Res. 49:1341-1343.
Srivastava et al. (1990) "Immunization with Soluble Gp96 Antigens Elicits Tumor-Specific Cellular Immunity," Cellular Immunity and the Immunotherapy of Cancer, pp. 307-314.
Srivastava et al. (1991) "Stress-induced proteins in immune response to cancer," Curr. Top. Microbiol. Immunol. 167:109-23.
Srivastava et al. (1993) "Evidence for peptide-chaperoning by the endoplasmic reticular heat shock protein GP96: implications for vaccination against cancer and infectious diseases," J. Cell. Biochem. Suppl. 17D:94, Abstract NZ014.
Srivastava et al. (1994) "Heat shock protein-peptide complexes in cancer immunotherapy," Curr. Opin. Immunol. 6(5):728-32.
Srivastava et al. (1994) "Heat shock proteins transfer peptides during antigen processing and CTL priming," Immunogenetics 39:93-98.
Srivastava et al. (2009) "Treating human cancers with heat shock protein-peptide complexes: the road ahead," Expert Opin Biol Ther 9: 179-186.
Srivastava, PK (1997) "Purification of heat shock protein-peptide complexes for use in vaccination against cancers and intracellular pathogens," Methods. 12(2):165-71.
Srivastava, PK (2000) "Heat shock protein-based novel immunotherapies," Drug News Perspect. 13(9):517-22.
Srivastava, PK (2000) "Immunotherapy of human cancer: lessons from mice," Nature Immunology. 1:363-366.
Srivastava, PK (2001) "A central role for heat shock proteins in host deficiency," Adv Exp Med Biol. 495:121-6.
Srivastava, PK (2005) "Immunotherapy for human cancer using heat shock protein-peptide complexes," Curr Oncol Rep. 7(2):104-8.
Srivastava, PK (2008) "New jobs for ancient chaperones," Sci Am. 299(1):50-5.
Srivastava, PK (2012) "Identification of chaperones as essential components of the tumor rejection moieties of cancers," Cancer Immunology Research. 12(1):1-5.
Srivastava, PK et al. (1998) "Heat shock proteins come of age: primitive functions acquire new roles in an adaptive world," Immunity. 8(6):657-65.
Srivastava, PK et al. (2001) "Heat shock proteins: the 'Swiss Army Knife' vaccines against cancers and infectious agents," Vaccine. 19(17-19):2590-7.
Stevens et al. (2003) "The solution structure of the bacterial HSP70 chaperone protein domain DnaK(393-507) in complex with the peptide NRLLLTG," Protein Sci. 12:2588-2596.
Stratton (2011) "Exploring the Genomes of Cancer Cells: Progress and Promise," Science 331:1553-1558.
Supplementary European Search Report for EP 04809742.2 dated Sep. 17, 2007 (5 pgs.).
Surquin et al. (2010) "Rapid, enhanced, and persistent protection of patients with renal insufficiency by AS02V-adjuvanted hepatitis B vaccine," Kidney Int 77:247-255.
Susumu et al. (2008) "Cross-presentation of NY-ESO-1 cytotoxic T lymphocyte epitope fused to human heat shock cognate protein by dendritic cells".
Suto et al. (1995) "A mechanism for the specific immunogenicity of heat shock protein-chaperoned peptides," Science 269(5230):1585-1588.
Tamura et al. (1997) "Immunotherapy of Tumors with Autologous Tumor-Derived Heat Shock Protein Preparations," Science 278:117-120.
Terasaki et al. (2008) J Clin Oncol, 2008 ASCO Annual Meeting Proceedings (Post-Meeting Edition) vol. 26, No. 15S (May 20 Supplement) (Abstract).
Testori et al. (2008) "Phase III Comparison of Vitespen, an Autologous Tumor-Derived Heat Shock Protein gp96 Peptide Complex Vaccine, With Physician's Choice of Treatment for Stage IV Melanoma: The C-100-21 Study Group," J Clin Oncol 26:955-962.
Testori, A. et al. (2008) "Phase III comparison of vitespen, an autologous tumor-derived heat shock protein gp96 peptide complex vaccine, with physician's choice of treatment for stage IV melanoma: the C-100-21 Study Group,"J Clin Oncol. 26(6):955-62.
Thomas et al. (1982) "Molecular and cellular effects of heat shock and related treatments of mammalian tissue-culture cells," Cold Spring Habor Symp. Quant. Biol. 46:985-996.
Tischer et al. (2011) "Heat shock protein 70/peptide complexes: potent mediators for the generation of antiviral T cells particularly with regard to low precursor frequencies," J Transl. Med. 9:175.
Udono (1993) "Heat shock proteins HSP70, HSP90 and GP96 elicit tumor specific immunity to the tumors from which they are isolated," J. Cell. Biochem. Suppl. 17D:113, Abstract NZ225.
Udono et al. (1993) "Heat shock protein 70-associated peptides elicit specific cancer immunity," J. Exp. Med. 178(4):1391-6.

(56) References Cited

OTHER PUBLICATIONS

Udono et al. (1994) "Comparison of tumor-specific immunogenicities of stress-induced proteins gp96, hsp90, and hsp70," J. Immunol. 152(11):5398-403.

Udono et al. (1994) "Cellular requirements for tumor-specific immunity elicited by heat shock proteins: Tumor rejection antigen gp96 primes CD8+ T cells in vivo," Proc Natl Acad Sci USA 91:3077-3081.

Ullrich et al. (1986) "A mouse tumor-specific transplantation antigen is a heat shock-related protein," Proc. Natl. Acad. Sci. U. S. A. 83(10):3121-5.

Van Allen et al. (2015) "Genomic correlates of response to CTLA4 blockade in metastatic melanoma," Science 350:207-211.

Van Den Enyde et al. (1991) "The gene coding for a major tumor rejection antigen of tumor P815 is identical to the normal gene of synergistic DBA/2 mice," J. Exp. Med. 173:1373-1384.

Van Rooij et al. (2013) "Tumor Exome Analysis Reveals Neoantigen-Specific T-Cell Reactivity in an Ipilimumab-Responsive Melanoma," J Clin Oncol 31:e439-e442.

Vanbuskirk et al. (1989) "A peptide binding protein having a role in antigen presentation is a member of the hsp70 heat shock family," J. Exp. Med. 170:1799-1809.

Varnavski et al. (2005) "Effective Induction of CD8 T-Cell Memory Response by Noncovalent Complex of Ileat Shock Protein 70 and Herpes Simplex Virus (11SV) Antigenic Peptide—Implication for HSV-2 Peptide Vaccine Development," Immunology 114:14 1-154 (Abstract No. R16).

Vatner, RE et al. (2010) "The tailless complex polypeptide-1 ring complex of the heat shock protein 60 family facilitates cross-priming of CD8 responses specific for chaperoned peptides," J Immunol. 185(11):6765-73.

Vermorken et al. (1999) "Active specific immunotherapy for stage II and stage III human colon cancer: a randomised trial" Lancet 353:345-350.

Wald et al. (2011) "Safety and immunogenicity of long HSV-2 peptides complexed with rhHsc70 in HSV-2 seropositive persons" Vaccine 29:8520-8529.

Wald, A. et al. (2011) "Safety and immunogenicity of long HSV-2 peptides complexed with rhHsc70 in HSV-2 seropositive persons," Vaccine. 29(47):8520-9.

Wang et al. (2001) "Characterization of heat shock protein 110 and glucose-regulated protein 170 as cancer vaccines and the effect of fever-range hyperthermia on vaccine activity," J. Immunol. 166(1):490-7.

Wang, R. et al. (2006) "Exogenous heat shock protein 70 binds macrophage lipid raft microdomain and stimulates phagocytosis, processing, and MHC-II presentation of antigens," Blood. 107(4):1636-42.

Wang, R. et al. (2006) "HSP70 enhances macrophage phagocytosis by interaction with lipid raft-associated TLR-7 and upregulating p38 MAPK and PI3K pathways," J Surg Res. 136(1):58-69.

Warren et al. (2010) "A census of predicted mutational epitopes suitable for immunologic cancer control" Hum Immunol. Mar. 2010;71(3):245-54, left-hand column, last paragraph.

Welch (1993) "How cells respond to stress," Sci. Am. 268(5):56-64.

Welch et al. (1982) "Purification of the major mammalian heat shock proteins," J. Biol. Chem. 257:14949-14959.

Welch et al. (1985) "Rapid purification of mammalian 70,000-dalton stress proteins: affinity of the proteins for nucleotides," Mol. Cell. Biol. 5:1229-1237.

White et al. (1988) "Differential Distribution of the Adenovirus E1A Proteins and Colocalization of E1A with the 70-Kilodalton Cellular Heat Shock Protein in Infected Cells," J. Virol. 62(11):4153-4166.

Wilson et al. (2012) "Iscomatrix vaccines mediate CD8+ T-cell cross-priming by a MyD88-dependent signaling pathway" Immunol Cell Biol 90:540-552.

Wood et al. (2008) "An adjuvant autologous therapeutic vaccine (HSPPC-96; vitespen) versus observation alone for patients at high risk of recurrence after nephrectomy for renal cell carcinoma: a multicentre, open-label, randomised phase III trial" Lancet 372(9633):145-54.

Yadav et al. (2014) "Predicting immunogenic tumour mutations by combining mass spectrometry and exome sequencing" (2014) Nature 515:572-576.

Yan et al. (2011) "Regulatory T-cell depletion synergizes with gp96-mediated cellular responses and antitumor activity." Cancer Immunol Immunother 60:1763-1774.

Yang, Y. et al. (2006) "Heat Shock Protein gp96 Is a Master Chaperone for Toll-like Receptors and Is Important in the Innate Function of Macrophages," Immunity. 26(2)215-216.

Yedavelli et al. (1999) "Preventive and therapeutic effect of tumor derived heat shock protein, gp96, in an experimental prostate cancer model." Int J Mol Med 4:243-248 (Abstract Only).

Young (1990) "Stress proteins and immunology," Annu. Rev. Immunol. 8:401-20.

Zarling et al. (2014) "MHC-Restricted Phosphopeptides from Insulin Receptor Substrate-2 and CDC25b Offer Broad-Based Immunotherapeutic Agents for Cancer" Cancer Res 74:6784-6795.

Zhang et al. (1998) "Interactions of peptides with DnaK and C-terminal DnaK fragments studied using fluorescent and radioactive peptides," Arch Biochem Biophys 356(2):177-86.

Zhang et al. (2014) "Crystal Structure of the Stress-Inducible Human Heat Shock Protein 70 Substrate-Binding Domain in Complex with Peptide Substrate" (2014) PLoS ONE 9:e103518.

Zhu et al. (1996) "Structural analysis of substrate binding by the molecular chaperone DnaK," Science 272(5268):1606-14.

Peterson et al. (2009) "Post-translationally modified T cell epitopes: immune recognition and immunotherapy," J Mol Med. 87:1045-1051.

Kershaw et al. (2014) "Clinical application of genetically modified T cells in cancer therapy," Clin Transl Immunology. 3(5): e16.

Van De Roemer et al. (2012) "P1737: IVAC: individualized vaccines for cancer," Immunology. 137(suppl. 1):715. Abstract.

Croft et al. (2011) "Peptidomimetics: modifying peptides in the pursuit of better vaccines," Review of Vaccines. 10:211-226.

Agenus Presentation, "Designing Effective Patient-Specific Neoantigen Cancer Vaccines" given by Cori Gorman Oct. 2018.

Agenus Presentation, "Heat Shock Protein Chaperoned Synthetic Long Peptide Cancer Vaccines" given by Mark Findeis May 9, 2018.

Agenus Presentation, "Agenus Synthetic Vaccines" given Mohamed Uduman Oct. 30, 2018.

Bekri et al. "Neoantigen-Specific CD4 T cells" AACR Dec. 2018.

Agenus Presentation, "Agenus Synthetic Vaccines" given Mohamed Uduman NeoAg Summit 2018.

Agenus Presentation, "Presentation of MHC Bound Phosphopeptides" given by Paisley Myers NeoAg Summit 2018.

Bekri et al. "Mechanisms of CD4+ T Cell Tumor Immunity" Keystone Symposia, Jan. 20-24, 2019, Vancouver Canada.

Agenus Presentation, "Agenus' Synthetic Neoantigen Vaccine Platforms" given by Daniel Levey Aug. 30, 2018.

Agenus Presentation, "Immunopeptidomics: Neoantigen Discovery" given by Paisley Myers Sep. 2018.

Agenus Presentation, "Omics, Big Data, Neoantigens" given by John Castle Dec. 3, 2018.

Myers, et al. "Identification of Phosphorylated Neoantigens" Abstract ASCO 2019.

Wesolowski, et al. "A Phase 1 Study of Safety and Tolerability of AutoSynVax" Abstract 2018.

Bekri, et al. "Mechanisms of CD4 T Cell Tumor Immunity" Abstract 2018.

Agenus Presentation, "Heat Shock Protein Chaperoned" given by Mark Findeis Nov. 28, 2018.

Agenus Presentation, "Heat Shock Protein Chaperoned" given by Mark Findeis Nov. 16, 2018.

Agenus Presentation, "Integrated Immunotherapy" given Mar. 29, 2018.

"Agenus and Gilead to Collaborate in a $150 M Upfront Transaction" Agenus News vol. 1, Issue 12, Dec. 21, 2018.

Agenus Presentation, "Investor Presentation" given Nov. 14, 2018.

(56) References Cited

OTHER PUBLICATIONS

Agenus Presentation, "Investor Presentation" given by Jennifer S. Buell, (2018).
Wesolowski, et al. "A phase 1 Study of Safety and Tolerability of AGEN2003 Vaccine" Poster.
Agenus Presentation, "Integrated Immunotherapy" given Apr. 7, 2017.
Agenus Presentation, "The Remarkable Efficiency of Chaperone-based Synthetic Cancer Vaccines" given Jun. 21, 2018.
"Agenus NexGen Neoantigen Vaccines" Agenus News vol. 1, Issue 2.
Agenus Presentation, "Enabling Best-in-Class I-O Combinations" given Nov. 2017.
Agenus Presentation, "Enabling Best-in-Class I-O Combinations" given Oct. 2017.
Agenus Presentation, "PhosphoSynVax AML Vaccine Opportunity" given Oct. 2018.
Drouin, et al. "AGEN1884, an IgG1 anti-CTLA-4 Antibody" poster presented at AACR, Washington DC Apr. 1-5, 2017.
Agenus Presentation, "Integrated Immunotherapy: Enabling Best-in-Class I-O Combinations" given Jun. 2017.
Agenus Presentation, "PhosphoSynVax Targeting Shared Phospho-Neo-Antigens" given Apr. 2017.
Agenus Presentation, "Corporate Presentation" given Sep. 2017.
Agenus Presentation, "Integrated Solutions in Immuno-Oncology" given May 2016.
Agenus Presentation, "Integrated Immunotherapy" given Nov. 2016.
Agenus Presentation, "Enabling Best-in-Class I-O Combinations" given Mar. 2018.
Uduman, et al. "Agenus' Next Generation Cancer Vaccine Platforms," poster presented at AACR, Washington DC Apr. 1-5, 2017.
Agenus Presentation, "Integrated Immunotherapy: Enabling Best-in-Class I-O Combinations" given Jan. 2018.
Agenus Presentation, "Integrated Immunotherapy: Enabling Best-in-Class I-O Combinations" given Feb. 2017.
Agenus Presentation, "Integrated Immunotherapy" given May 5, 2017.
Agenus Presentation, "Integrated Immunotherapy" given Jan. 2017.
Agenus Presentation, "Integrated Immunotherapy" given Sep. 29, 2016.
"Year in Review 2018" Agenus News vol. 1, Issue 11, Dec. 3, 2018.
"Agenus Enabling Partners," Agenus News vol. 1, Issue 6, Sep. 24, 2018.
International Preliminary Report on Patentability for PCT International Application No. PCT/US2019/029112m dated Sep. 10, 2020, 13 pages.

* cited by examiner

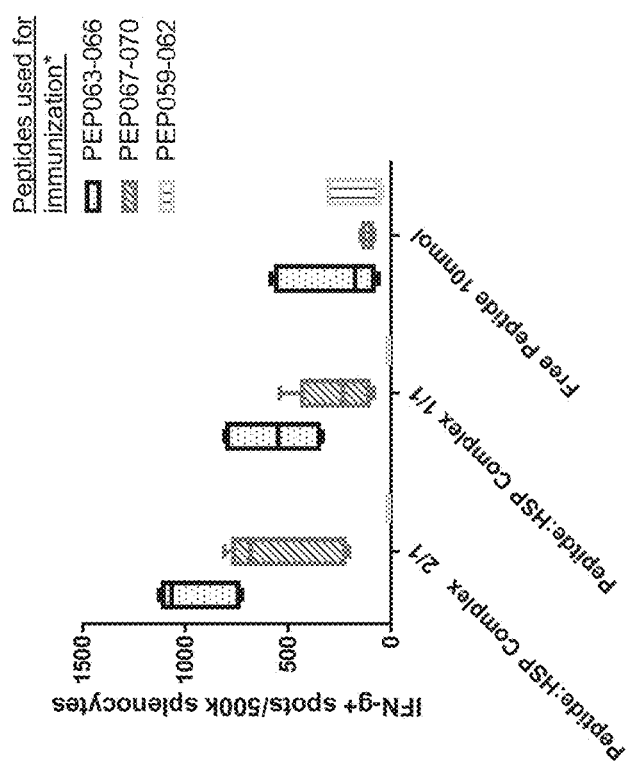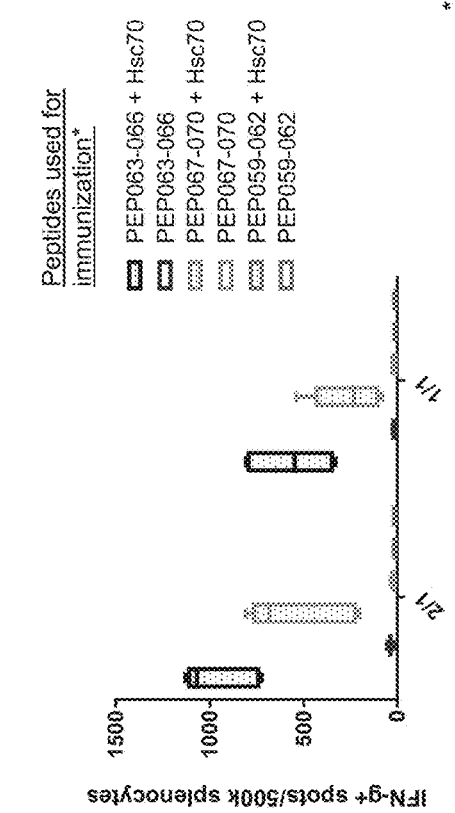
FIG. 5A
FIG. 5B

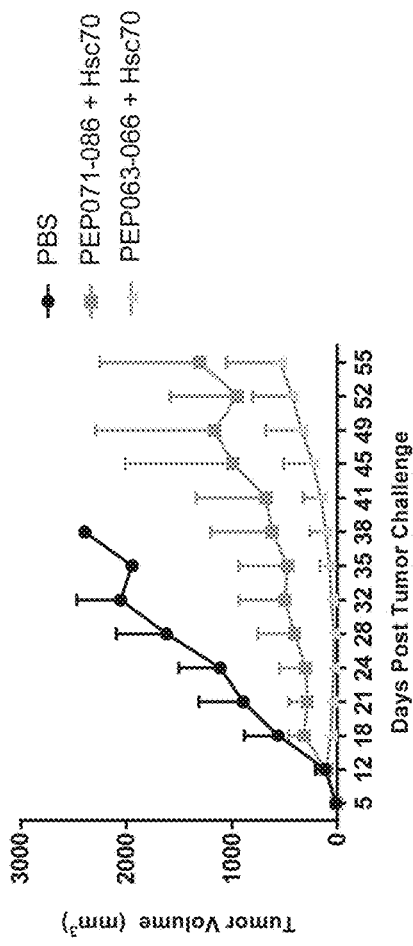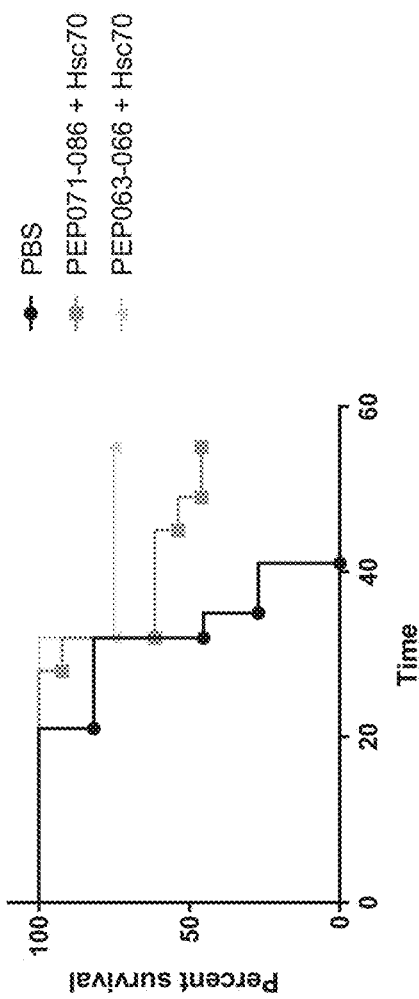
FIG. 8A
FIG. 8B

FIG. 9A
A. Tumor Growth Kinetics in Individual Mice
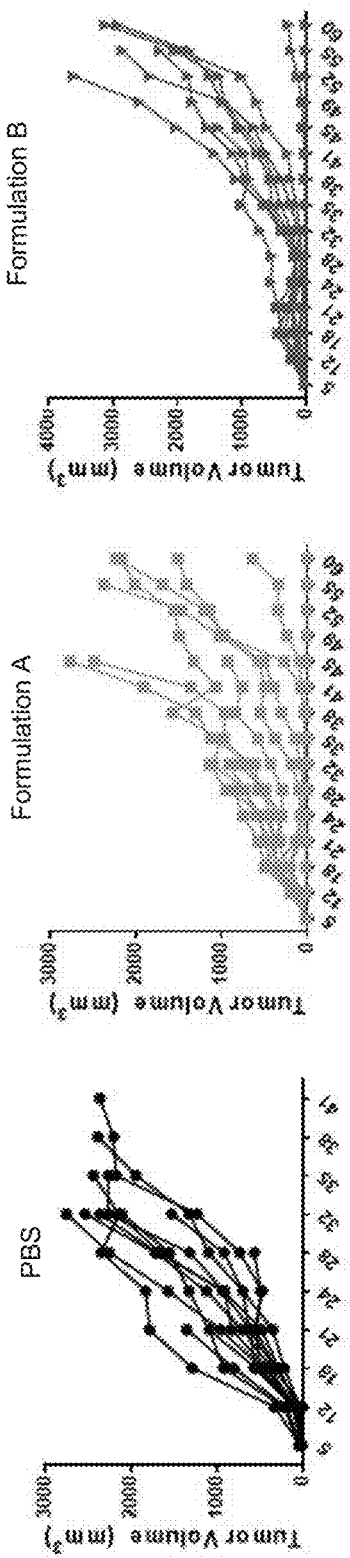
FIG. 9B
B. Group Mean Tumor Growth Kinetics
FIG. 9C
C. Overall Survival
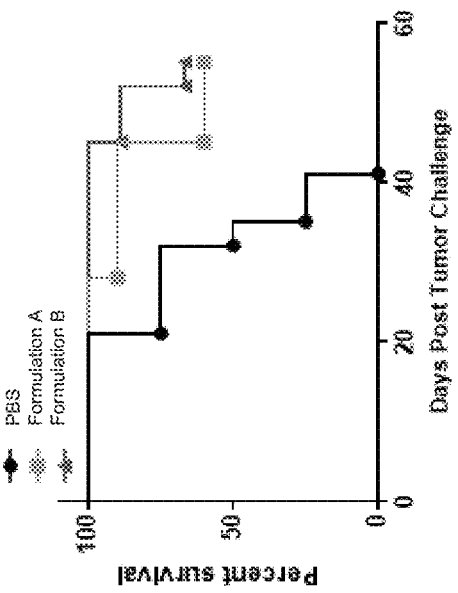
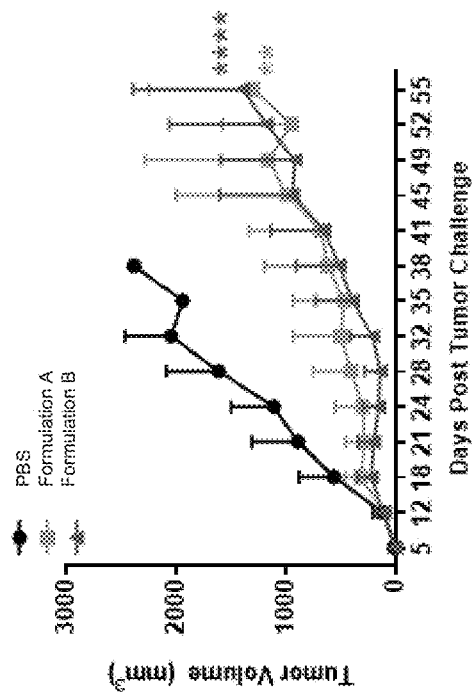

SEQUENCE LISTING

```
<160> NUMBER OF SEQ ID NOS: 234

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Trp or Phe
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (6)..(6)
<223> OTHER INFORMATION: Trp, Phe, or Gly

<400> SEQUENCE: 1

Xaa Leu Xaa Leu Thr Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Trp or Phe
<220> FEATURE:
<221> NAME/KEY: MOD_RES
<222> LOCATION: (4)..(4)
<223> OTHER INFORMATION: Arg or Lys
<220> FEATURE:
<221> NAME/KEY: MOD_RES
<222> LOCATION: (7)..(7)
<223> OTHER INFORMATION: Trp, Phe, or Gly

<400> SEQUENCE: 2

Asn Xaa Leu Xaa Leu Thr Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (6)..(6)
<223> OTHER INFORMATION: Trp or Gly

<400> SEQUENCE: 3

Trp Leu Xaa Leu Thr Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Arg or Lys
<220> FEATURE:
<221> NAME/KEY: MOD_RES
<222> LOCATION: (7)..(7)
```

```
<223> OTHER INFORMATION: Trp or Gly

<400> SEQUENCE: 4

Asn Trp Leu Xaa Leu Thr Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Leu Arg Leu Thr Trp
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Trp Leu Arg Leu Thr Trp
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Leu Lys Leu Thr Trp
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Trp Leu Lys Leu Thr Trp
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Leu Arg Leu Thr Gly
1               5

<210> SEQ ID NO 10
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Trp Leu Arg Leu Thr Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Leu Arg Leu Thr Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Phe Leu Arg Leu Thr Phe
1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Phe Arg Lys
1

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Trp or Phe
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (10)..(10)
<223> OTHER INFORMATION: Trp, Phe, or Gly

<400> SEQUENCE: 14

Phe Phe Arg Lys Xaa Leu Xaa Leu Thr Xaa
1               5                   10
```

```
<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Trp or Phe
<220> FEATURE:
<221> NAME/KEY: MOD_RES
<222> LOCATION: (8)..(8)
<223> OTHER INFORMATION: Arg or Lys
<220> FEATURE:
<221> NAME/KEY: MOD_RES
<222> LOCATION: (11)..(11)
<223> OTHER INFORMATION: Trp, Phe, or Gly

<400> SEQUENCE: 15

Phe Phe Arg Lys Asn Xaa Leu Xaa Leu Thr Xaa
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (10)..(10)
<223> OTHER INFORMATION: Trp or Gly

<400> SEQUENCE: 16

Phe Phe Arg Lys Trp Leu Xaa Leu Thr Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Arg or Lys
<220> FEATURE:
<221> NAME/KEY: MOD_RES
<222> LOCATION: (11)..(11)
<223> OTHER INFORMATION: Trp or Gly

<400> SEQUENCE: 17

Phe Phe Arg Lys Asn Trp Leu Xaa Leu Thr Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 18

Phe Phe Arg Lys Asn Trp Leu Arg Leu Thr Trp
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Phe Arg Lys Asn Trp Leu Lys Leu Thr Trp
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Phe Arg Lys Asn Trp Leu Arg Leu Thr Gly
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Phe Arg Lys Asn Phe Leu Arg Leu Thr Phe
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Arg Asn Trp Leu Arg Leu Thr Trp
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Arg Asn Trp Leu Lys Leu Thr Trp
1               5

<210> SEQ ID NO 24
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Arg Asn Trp Leu Arg Leu Thr Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Arg Asn Phe Leu Arg Leu Thr Phe
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or Phe
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (6)..(6)
<223> OTHER INFORMATION: Trp, Phe, or Gly

<400> SEQUENCE: 26

Xaa Leu Xaa Leu Thr Xaa Phe Phe Arg Lys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Trp or Phe
<220> FEATURE:
<221> NAME/KEY: MOD_RES
<222> LOCATION: (4)..(4)
<223> OTHER INFORMATION: Arg or Lys
<220> FEATURE:
<221> NAME/KEY: MOD_RES
<222> LOCATION: (7)..(7)
<223> OTHER INFORMATION: Trp, Phe, or Gly

<400> SEQUENCE: 27

Asn Xaa Leu Xaa Leu Thr Xaa Phe Phe Arg Lys
1               5                   10

<210> SEQ ID NO 28
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (6)..(6)
<223> OTHER INFORMATION: Trp or Gly

<400> SEQUENCE: 28

Trp Leu Xaa Leu Thr Xaa Phe Phe Arg Lys
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Arg or Lys
<220> FEATURE:
<221> NAME/KEY: MOD_RES
<222> LOCATION: (7)..(7)
<223> OTHER INFORMATION: Trp or Gly

<400> SEQUENCE: 29

Asn Trp Leu Xaa Leu Thr Xaa Phe Phe Arg Lys
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Trp Leu Arg Leu Thr Trp Phe Phe Arg Lys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Trp Leu Lys Leu Thr Trp Phe Phe Arg Lys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Asn Trp Leu Arg Leu Thr Gly Phe Phe Arg Lys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Phe Leu Arg Leu Thr Phe Phe Phe Arg Lys
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Trp Leu Arg Leu Thr Trp Phe Arg
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asn Trp Leu Lys Leu Thr Trp Phe Arg
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asn Trp Leu Arg Leu Thr Gly Phe Arg
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn Phe Leu Arg Leu Thr Phe Phe Arg
1               5

<210> SEQ ID NO 38
<211> LENGTH: 30
<212> TYPE: PRT
```

<213> ORGANISM: Human papillomavirus

<400> SEQUENCE: 38

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile
            20                  25                  30

<210> SEQ ID NO 39
<211> LENGTH: 30
<212> TYPE: PRT
<213> ORGANISM: Human papillomavirus

<400> SEQUENCE: 39

Pro Arg Lys Leu Pro Gln Leu Cys Thr Glu Leu Gln Thr Thr Ile His
1               5                   10                  15

Asp Ile Ile Leu Glu Cys Val Tyr Cys Lys Gln Gln Leu Leu
            20                  25                  30

<210> SEQ ID NO 40
<211> LENGTH: 30
<212> TYPE: PRT
<213> ORGANISM: Human papillomavirus

<400> SEQUENCE: 40

His Asp Ile Ile Leu Glu Cys Val Tyr Cys Lys Gln Gln Leu Leu Arg
1               5                   10                  15

Arg Glu Val Tyr Asp Phe Ala Phe Arg Asp Leu Cys Ile Val
            20                  25                  30

<210> SEQ ID NO 41
<211> LENGTH: 31
<212> TYPE: PRT
<213> ORGANISM: Human papillomavirus

<400> SEQUENCE: 41

Arg Arg Glu Val Tyr Asp Phe Ala Phe Arg Asp Leu Cys Ile Val Tyr
1               5                   10                  15

Arg Asp Gly Asn Pro Tyr Ala Val Cys Asp Lys Cys Leu Lys Phe
            20                  25                  30

<210> SEQ ID NO 42
<211> LENGTH: 30
<212> TYPE: PRT
<213> ORGANISM: Human papillomavirus

<400> SEQUENCE: 42

Arg Asp Gly Asn Pro Tyr Ala Val Cys Asp Lys Cys Leu Lys Phe Tyr
1               5                   10                  15

Ser Lys Ile Ser Glu Tyr Arg His Tyr Cys Tyr Ser Leu Tyr
            20                  25                  30

<210> SEQ ID NO 43
<211> LENGTH: 30
<212> TYPE: PRT
<213> ORGANISM: Human papillomavirus

<400> SEQUENCE: 43

Tyr Ser Lys Ile Ser Glu Tyr Arg His Tyr Cys Tyr Ser Leu Tyr Gly
1               5                   10                  15

Thr Thr Leu Glu Gln Gln Tyr Asn Lys Pro Leu Cys Asp Leu
            20                  25                  30

```
<210> SEQ ID NO 44
<211> LENGTH: 28
<212> TYPE: PRT
<213> ORGANISM: Human papillomavirus

<400> SEQUENCE: 44

Gly Thr Thr Leu Glu Gln Gln Tyr Asn Lys Pro Leu Cys Asp Leu Leu
1               5                   10                  15

Ile Arg Cys Ile Asn Cys Gln Lys Pro Leu Cys Pro
            20                  25

<210> SEQ ID NO 45
<211> LENGTH: 29
<212> TYPE: PRT
<213> ORGANISM: Human papillomavirus

<400> SEQUENCE: 45

Asp Leu Leu Ile Arg Cys Ile Asn Cys Gln Lys Pro Leu Cys Pro Glu
1               5                   10                  15

Glu Lys Gln Arg His Leu Asp Lys Lys Gln Arg Phe His
            20                  25

<210> SEQ ID NO 46
<211> LENGTH: 23
<212> TYPE: PRT
<213> ORGANISM: Human papillomavirus

<400> SEQUENCE: 46

Pro Glu Glu Lys Gln Arg His Leu Asp Lys Lys Gln Arg Phe His Asn
1               5                   10                  15

Ile Arg Gly Arg Trp Thr Gly
            20

<210> SEQ ID NO 47
<211> LENGTH: 32
<212> TYPE: PRT
<213> ORGANISM: Human papillomavirus

<400> SEQUENCE: 47

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

<210> SEQ ID NO 48
<211> LENGTH: 29
<212> TYPE: PRT
<213> ORGANISM: Human papillomavirus

<400> SEQUENCE: 48

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn
            20                  25

<210> SEQ ID NO 49
<211> LENGTH: 27
<212> TYPE: PRT
<213> ORGANISM: Human papillomavirus

<400> SEQUENCE: 49
```

```
Leu Gln Pro Glu Thr Thr Asp Leu Tyr Cys Tyr Glu Gln Leu Asn Asp
1               5                   10                  15

Ser Ser Glu Glu Glu Asp Glu Ile Asp Gly Pro
            20                  25
```

<210> SEQ ID NO 50
<211> LENGTH: 29
<212> TYPE: PRT
<213> ORGANISM: Human papillomavirus

<400> SEQUENCE: 50

```
Gln Leu Asn Asp Ser Ser Glu Glu Asp Glu Ile Asp Gly Pro Ala
1               5                   10                  15

Gly Gln Ala Glu Pro Asp Arg Ala His Tyr Asn Ile Val
            20                  25
```

<210> SEQ ID NO 51
<211> LENGTH: 29
<212> TYPE: PRT
<213> ORGANISM: Human papillomavirus

<400> SEQUENCE: 51

```
Pro Ala Gly Gln Ala Glu Pro Asp Arg Ala His Tyr Asn Ile Val Thr
1               5                   10                  15

Phe Cys Cys Lys Cys Asp Ser Thr Leu Arg Leu Cys Val
            20                  25
```

<210> SEQ ID NO 52
<211> LENGTH: 29
<212> TYPE: PRT
<213> ORGANISM: Human papillomavirus

<400> SEQUENCE: 52

```
Val Thr Phe Cys Cys Lys Cys Asp Ser Thr Leu Arg Leu Cys Val Gln
1               5                   10                  15

Ser Thr His Val Asp Ile Arg Thr Leu Glu Asp Leu Leu
            20                  25
```

<210> SEQ ID NO 53
<211> LENGTH: 30
<212> TYPE: PRT
<213> ORGANISM: Human papillomavirus

<400> SEQUENCE: 53

```
Val Gln Ser Thr His Val Asp Ile Arg Thr Leu Glu Asp Leu Leu Met
1               5                   10                  15

Gly Thr Leu Gly Ile Val Cys Pro Ile Cys Ser Gln Lys Pro
            20                  25                  30
```

<210> SEQ ID NO 54
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile Phe Phe
            20                  25                  30
```

```
Arg Lys Asn Trp Leu Arg Leu Thr Trp
        35                  40
```

<210> SEQ ID NO 55
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Pro Arg Lys Leu Pro Gln Leu Cys Thr Glu Leu Gln Thr Thr Ile His
1               5                   10                  15

Asp Ile Ile Leu Glu Cys Val Tyr Cys Lys Gln Gln Leu Leu Phe Phe
            20                  25                  30

Arg Lys Asn Trp Leu Arg Leu Thr Trp
        35                  40
```

<210> SEQ ID NO 56
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
His Asp Ile Ile Leu Glu Cys Val Tyr Cys Lys Gln Gln Leu Leu Arg
1               5                   10                  15

Arg Glu Val Tyr Asp Phe Ala Phe Arg Asp Leu Cys Ile Val Phe Phe
            20                  25                  30

Arg Lys Asn Trp Leu Arg Leu Thr Trp
        35                  40
```

<210> SEQ ID NO 57
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Arg Arg Glu Val Tyr Asp Phe Ala Phe Arg Asp Leu Cys Ile Val Tyr
1               5                   10                  15

Arg Asp Gly Asn Pro Tyr Ala Val Cys Asp Lys Cys Leu Lys Phe Phe
            20                  25                  30

Phe Arg Lys Asn Trp Leu Arg Leu Thr Trp
        35                  40
```

<210> SEQ ID NO 58
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Arg Asp Gly Asn Pro Tyr Ala Val Cys Asp Lys Cys Leu Lys Phe Tyr
1               5                   10                  15

Ser Lys Ile Ser Glu Tyr Arg His Tyr Cys Tyr Ser Leu Tyr Phe Phe
            20                  25                  30
```

```
Arg Lys Asn Trp Leu Arg Leu Thr Trp
        35                  40

<210> SEQ ID NO 59
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Tyr Ser Lys Ile Ser Glu Tyr Arg His Tyr Cys Tyr Ser Leu Tyr Gly
1               5                   10                  15

Thr Thr Leu Glu Gln Gln Tyr Asn Lys Pro Leu Cys Asp Leu Phe Phe
            20                  25                  30

Arg Lys Asn Trp Leu Arg Leu Thr Trp
        35                  40

<210> SEQ ID NO 60
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Thr Thr Leu Glu Gln Gln Tyr Asn Lys Pro Leu Cys Asp Leu Leu
1               5                   10                  15

Ile Arg Cys Ile Asn Cys Gln Lys Pro Leu Cys Pro Phe Phe Arg Lys
            20                  25                  30

Asn Trp Leu Arg Leu Thr Trp
        35

<210> SEQ ID NO 61
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Leu Leu Ile Arg Cys Ile Asn Cys Gln Lys Pro Leu Cys Pro Glu
1               5                   10                  15

Glu Lys Gln Arg His Leu Asp Lys Lys Gln Arg Phe His Phe Phe Arg
            20                  25                  30

Lys Asn Trp Leu Arg Leu Thr Trp
        35                  40

<210> SEQ ID NO 62
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Pro Glu Glu Lys Gln Arg His Leu Asp Lys Lys Gln Arg Phe His Asn
1               5                   10                  15

Ile Arg Gly Arg Trp Thr Gly Phe Phe Arg Lys Asn Trp Leu Arg Leu
```

```
                    20                  25                  30

Thr Trp

<210> SEQ ID NO 63
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
                20                  25                  30

Phe Phe Arg Lys Asn Trp Leu Arg Leu Thr Trp
            35                  40

<210> SEQ ID NO 64
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Phe Phe Arg
                20                  25                  30

Lys Asn Trp Leu Arg Leu Thr Trp
            35                  40

<210> SEQ ID NO 65
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Leu Gln Pro Glu Thr Thr Asp Leu Tyr Cys Tyr Glu Gln Leu Asn Asp
1               5                   10                  15

Ser Ser Glu Glu Glu Asp Glu Ile Asp Gly Pro Phe Phe Arg Lys Asn
                20                  25                  30

Trp Leu Arg Leu Thr Trp
            35

<210> SEQ ID NO 66
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Asn Asp Ser Ser Glu Glu Glu Asp Glu Ile Asp Gly Pro Ala
1               5                   10                  15

Gly Gln Ala Glu Pro Asp Arg Ala His Tyr Asn Ile Val Phe Phe Arg
```

```
                    20                  25                  30

Lys Asn Trp Leu Arg Leu Thr Trp
        35                  40

<210> SEQ ID NO 67
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Pro Ala Gly Gln Ala Glu Pro Asp Arg Ala His Tyr Asn Ile Val Thr
1               5                   10                  15

Phe Cys Cys Lys Cys Asp Ser Thr Leu Arg Leu Cys Val Phe Phe Arg
                20                  25                  30

Lys Asn Trp Leu Arg Leu Thr Trp
        35                  40

<210> SEQ ID NO 68
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Val Thr Phe Cys Cys Lys Cys Asp Ser Thr Leu Arg Leu Cys Val Gln
1               5                   10                  15

Ser Thr His Val Asp Ile Arg Thr Leu Glu Asp Leu Leu Phe Phe Arg
                20                  25                  30

Lys Asn Trp Leu Arg Leu Thr Trp
        35                  40

<210> SEQ ID NO 69
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Val Gln Ser Thr His Val Asp Ile Arg Thr Leu Glu Asp Leu Leu Met
1               5                   10                  15

Gly Thr Leu Gly Ile Val Cys Pro Ile Cys Ser Gln Lys Pro Phe Phe
                20                  25                  30

Arg Lys Asn Trp Leu Arg Leu Thr Trp
        35                  40

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asn Leu Leu Arg Leu Thr Gly
1               5
```

```
<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Phe Phe Arg Lys Asn Leu Leu Arg Leu Thr Gly
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Phe Phe Arg Lys Asn Trp Leu Lys Leu Lys Trp
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Phe Phe Arg Lys Asn Trp Leu Lys Leu Lys Trp
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Phe Arg Lys Asn Trp Leu Lys Leu Arg Trp
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Phe Arg Lys Asn Trp Leu Lys Leu Trp Lys
1               5                   10

<210> SEQ ID NO 76
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 76

Leu Gly Val Val Arg Pro Arg Ala Leu His Arg Glu Leu Asp Leu Val
1               5                   10                  15

Asp Asp Ser Pro Thr Pro Gly Ser Pro Gly Ser
            20                  25

<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Leu Gly Val Val Arg Pro Arg Ala Leu His Arg Glu Leu Asp Leu Val
1               5                   10                  15

Asp Asp Ser Pro Thr Pro Gly Ser Pro Gly Ser Phe Phe Arg Lys Asn
            20                  25                  30

Trp Leu Arg Leu Thr Trp
        35

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ala His Tyr Asn Ile Val Thr Phe
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Val Tyr Asp Phe Ala Phe Arg Asp Leu
1               5

<210> SEQ ID NO 80
<211> LENGTH: 19
<212> TYPE: PRT
<213> ORGANISM: Human papillomavirus

<400> SEQUENCE: 80

Gln Ala Glu Pro Asp Arg Ala His Tyr Asn Ile Val Thr Phe Cys Cys
1               5                   10                  15

Lys Cys Asp

<210> SEQ ID NO 81
<211> LENGTH: 9
<212> TYPE: PRT
<213> ORGANISM: Human papillomavirus

<400> SEQUENCE: 81

Arg Ala His Tyr Asn Ile Val Thr Phe
1               5
```

```
<210> SEQ ID NO 82
<211> LENGTH: 15
<212> TYPE: PRT
<213> ORGANISM: Human papillomavirus

<400> SEQUENCE: 82

Gln Leu Leu Arg Arg Glu Val Tyr Asp Phe Ala Phe Arg Asp Leu
1               5                   10                  15

<210> SEQ ID NO 83
<211> LENGTH: 10
<212> TYPE: PRT
<213> ORGANISM: Human papillomavirus

<400> SEQUENCE: 83

Val Tyr Asp Phe Ala Phe Arg Asp Leu Cys
1               5                   10

<210> SEQ ID NO 84
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ala Glu Pro Asp Arg Ala His Tyr Asn Ile Val Thr Phe Cys Cys
1               5                   10                  15

Lys Cys Asp Phe Phe Arg Lys Asn Leu Leu Arg Leu Thr Gly
            20                  25                  30

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ala His Tyr Asn Ile Val Thr Phe Phe Phe Arg Lys Asn Leu Leu
1               5                   10                  15

Arg Leu Thr Gly
            20

<210> SEQ ID NO 86
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Leu Leu Arg Arg Glu Val Tyr Asp Phe Ala Phe Arg Asp Leu Phe
1               5                   10                  15

Phe Arg Lys Asn Leu Leu Arg Leu Thr Gly
            20                  25

<210> SEQ ID NO 87
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 87

Val Tyr Asp Phe Ala Phe Arg Asp Leu Cys Phe Phe Arg Lys Asn Leu
1               5                   10                  15

Leu Arg Leu Thr Gly
            20

<210> SEQ ID NO 88
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Ala Glu Pro Asp Arg Ala His Tyr Asn Ile Val Thr Phe Cys Cys
1               5                   10                  15

Lys Cys Asp Phe Phe Arg Lys Asn Trp Leu Arg Leu Thr Trp
            20                  25                  30

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ala His Tyr Asn Ile Val Thr Phe Phe Arg Lys Asn Trp Leu
1               5                   10                  15

Arg Leu Thr Trp
            20

<210> SEQ ID NO 90
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Leu Leu Arg Arg Glu Val Tyr Asp Phe Ala Phe Arg Asp Leu Phe
1               5                   10                  15

Phe Arg Lys Asn Trp Leu Arg Leu Thr Trp
            20                  25

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Tyr Asp Phe Ala Phe Arg Asp Leu Cys Phe Phe Arg Lys Asn Trp
1               5                   10                  15

Leu Arg Leu Thr Trp
            20
```

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Val Tyr Asp Phe Ala Phe Arg Asp Leu
1               5                   10

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Tyr Met Leu Asp Leu Gln Pro Glu Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Leu Asp Leu Gln Pro Glu Thr Thr
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Leu Met Gly Thr Leu Gly Ile Val Cys
1               5                   10

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Ile Ile Asn Phe Glu Lys Leu
1               5

<210> SEQ ID NO 97
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 97

Glu Val Ser Gly Leu Glu Gln Leu Glu Ser Ile Ile Asn Phe Glu Lys
1               5                   10                  15

Leu Thr Glu Trp Thr Ser Ser Asn Val Met Glu
            20                  25

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Leu Arg Leu Thr Phe
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asn Trp Leu Arg Leu Thr Phe
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Leu Lys Leu Thr Phe
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asn Trp Leu Lys Leu Thr Phe
1               5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Trp Leu Lys Leu Thr Gly
1               5
```

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Trp Leu Lys Leu Thr Gly
1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Phe Leu Arg Leu Thr Trp
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asn Phe Leu Arg Leu Thr Trp
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Phe Leu Arg Leu Thr Gly
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asn Phe Leu Arg Leu Thr Gly
1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 108

Phe Leu Lys Leu Thr Trp
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asn Phe Leu Lys Leu Thr Trp
1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Phe Leu Lys Leu Thr Phe
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asn Phe Leu Lys Leu Thr Phe
1               5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Phe Leu Lys Leu Thr Gly
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asn Phe Leu Lys Leu Thr Gly
1               5

<210> SEQ ID NO 114
<211> LENGTH: 27
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 114

Lys Phe Pro Leu Ile Leu Tyr Leu Gly Met Ala Ile Val Thr Val Leu
1               5                   10                  15

Tyr Ile Ser Leu Gly Ser Leu Gly Tyr Leu Gln
            20                  25

<210> SEQ ID NO 115
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Met Arg Gly Cys Gly Pro Cys Leu Arg Ile Ala Pro Ser Phe Ser
1               5                   10                  15

Ser Met Ser Asn Lys Tyr Pro Gln Ala Val Phe
            20                  25

<210> SEQ ID NO 116
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Met Lys Lys Glu Asn Leu Met Pro Arg Glu Glu Leu Ala Arg Leu
1               5                   10                  15

Phe Pro Asn Leu Pro Glu Leu Ile Glu Ile His
            20                  25

<210> SEQ ID NO 117
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Phe Ser Arg Thr Trp Ile Gly Ile Trp Ser Val Leu Cys Phe Ala Ser
1               5                   10                  15

Thr Leu Phe Thr Val Leu Thr Tyr Leu Val Asp
            20                  25

<210> SEQ ID NO 118
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Ser Leu Ala Ile Gly Thr Lys Ser Gly Tyr Lys Leu Phe Ser Leu
1               5                   10                  15

Ser Ser Val Glu Gln Leu Asp Gln Val His Gly
            20                  25
```

20                  25

<210> SEQ ID NO 119
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Leu Phe Pro Thr Asp Cys His Ser Val Pro Pro His Tyr Thr Glu Leu
1               5                   10                  15

Leu Thr Phe His Ser Lys Glu Gly Thr Asp His
            20                  25

<210> SEQ ID NO 120
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Pro Ser Arg Gly Ser Ser Ser Ser Gly Tyr Pro Val Gly Val Val
1               5                   10                  15

Phe Gln Pro Val Gly Ser Gly Gly Val Gln Pro
            20                  25

<210> SEQ ID NO 121
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Ser Pro Gly Ala Ala Ala Pro Ser Gly Trp Ala Leu Ala Pro Leu
1               5                   10                  15

Gly Asp Thr Met Lys Ile Tyr Met Glu Leu Gln
            20                  25

<210> SEQ ID NO 122
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Glu Leu Tyr Arg Lys Leu Leu Arg Ser Gln Ser Val Arg Phe Cys Phe
1               5                   10                  15

Gln Gly Leu Leu Glu Asn Ser Ala His Leu Ile
            20                  25

<210> SEQ ID NO 123
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 123

Ala Gln Val Ile Ile Leu Asn His Pro Gly Gln Ile Ser Thr Gly Tyr
1               5                   10                  15

Ala Pro Val Leu Asp Cys His Thr Ala His Ile
            20                  25

<210> SEQ ID NO 124
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Pro Val Gln Leu Trp Val Ser Ala Thr Pro Ala Gly Ser Pro Val
1               5                   10                  15

Arg Ala Met Ala Ile Tyr Lys Lys Ser Gln His
            20                  25

<210> SEQ ID NO 125
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asn Ala Phe Asn Pro Leu Asn Ala Ser Ala Ser Leu Pro Pro Ala Ala
1               5                   10                  15

Met Pro Ile Thr Thr Ala Asp Gly Arg Ser Asp
            20                  25

<210> SEQ ID NO 126
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Gly Ser Val Ala Gly Asn Lys Leu Leu Arg Ala Ala Trp Arg Arg
1               5                   10                  15

Ala Ser Leu Ala Ala Thr Ser Leu Ala Leu Gly
            20                  25

<210> SEQ ID NO 127
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Glu Thr Ser Leu Leu Glu Ala Gly Ala Ser Ala Ala Ser Thr Ala
1               5                   10                  15

Ala Ala Leu Glu Asn Leu Gln Val Glu Ala Ser
            20                  25

<210> SEQ ID NO 128
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asn Ser Val Leu Gln Thr Leu Leu Gln Met Arg Ala Ala Lys Ser Ser
1               5                   10                  15

Val Ala Pro Ser Arg Glu Glu Leu Leu Gly Thr
            20                  25

<210> SEQ ID NO 129
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Phe Thr His Pro Glu Ala Arg Glu Trp Phe Gln Gly Leu Leu Arg
1               5                   10                  15

Arg Leu Arg Leu Arg Tyr Asn Val Thr Ser Phe
            20                  25

<210> SEQ ID NO 130
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Lys Lys His Asp Val Arg Ser Ile Ile Gly Ser Pro Gly Leu Pro Phe
1               5                   10                  15

Pro Ala Leu His Pro Leu Asp Ile Met Ala Asp
            20                  25

<210> SEQ ID NO 131
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Gly Arg Pro Arg Pro Val Leu Arg Ser Val Asn Ser Leu Glu Pro
1               5                   10                  15

Ser Gln Val Ile Phe Cys Asn Arg Ser Pro Arg
            20                  25

<210> SEQ ID NO 132
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Thr Phe Phe Ala Ser Asp Asn Ala Val Asp Ile Thr Thr Leu Thr Asn
1               5                   10                  15
```

Ser Cys Leu Ser Asn Ser Asp His Ser Arg Asp
            20                  25

<210> SEQ ID NO 133
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Leu Leu Arg Ser Ser Tyr Val Ala Gln Val Pro Leu Leu Thr Leu
1               5                   10                  15

Cys Thr Arg Gly Pro Pro Glu Glu Asp Ala Pro
            20                  25

<210> SEQ ID NO 134
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Met Phe Ser Phe Asn Met Phe Asp His Pro Ile Pro Leu Val Phe Gln
1               5                   10                  15

Asn Arg Phe Ser Thr Gln Tyr Arg
            20

<210> SEQ ID NO 135
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Thr Ala Ala Gly Ser Ser Thr Ile Ser Gln Asp Thr Ile His Leu
1               5                   10                  15

Thr Ser Gly Pro Val Ser Ala Leu Ala Ser Gly
            20                  25

<210> SEQ ID NO 136
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Cys Ser Ser Ser Tyr Asn Ser Ala Val Met Glu Ser Ser Ser Val
1               5                   10                  15

Asn Val Ser Met Val His Ser Ser Ser Lys Glu
            20                  25

<210> SEQ ID NO 137
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 137

Val Leu Gln Glu Trp Lys Ala Cys Asp Lys Leu Tyr Asp Val Ala Thr
1               5                   10                  15

Met Arg Thr Thr Gln Leu Thr Tyr Ser Met Glu
            20                  25

<210> SEQ ID NO 138
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Asp Pro Phe Arg Val Arg Ala Ser Ala Ala Leu Leu Asn Lys Leu
1               5                   10                  15

Tyr Ala Met Gly Leu Val Pro Thr Arg Gly Ser
            20                  25

<210> SEQ ID NO 139
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Lys Phe Pro Leu Ile Leu Tyr Leu Gly Met Ala Ile Val Thr Val Leu
1               5                   10                  15

Tyr Ile Ser Leu Gly Ser Leu Gly Tyr Leu Gln Phe Phe Arg Lys Asn
            20                  25                  30

Trp Leu Arg Leu Thr Trp
        35

<210> SEQ ID NO 140
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Thr Met Arg Gly Cys Gly Pro Cys Leu Arg Ile Ala Pro Ser Phe Ser
1               5                   10                  15

Ser Met Ser Asn Lys Tyr Pro Gln Ala Val Phe Phe Phe Arg Lys Asn
            20                  25                  30

Trp Leu Arg Leu Thr Trp
        35

<210> SEQ ID NO 141
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Arg Met Lys Lys Glu Asn Leu Met Pro Arg Glu Glu Leu Ala Arg Leu
1               5                   10                  15
```

```
Phe Pro Asn Leu Pro Glu Leu Ile Glu Ile His Phe Arg Lys Asn
                20                  25                  30

Trp Leu Arg Leu Thr Trp
        35

<210> SEQ ID NO 142
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Phe Ser Arg Thr Trp Ile Gly Ile Trp Ser Val Leu Cys Phe Ala Ser
1               5                   10                  15

Thr Leu Phe Thr Val Leu Thr Tyr Leu Val Asp Phe Arg Lys Asn
                20                  25                  30

Trp Leu Arg Leu Thr Trp
        35

<210> SEQ ID NO 143
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Thr Ser Leu Ala Ile Gly Thr Lys Ser Gly Tyr Lys Leu Phe Ser Leu
1               5                   10                  15

Ser Ser Val Glu Gln Leu Asp Gln Val His Gly Phe Phe Arg Lys Asn
                20                  25                  30

Trp Leu Arg Leu Thr Trp
        35

<210> SEQ ID NO 144
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Leu Phe Pro Thr Asp Cys His Ser Val Pro Pro His Tyr Thr Glu Leu
1               5                   10                  15

Leu Thr Phe His Ser Lys Glu Gly Thr Asp His Phe Phe Arg Lys Asn
                20                  25                  30

Trp Leu Arg Leu Thr Trp
        35

<210> SEQ ID NO 145
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Pro Ser Arg Gly Ser Ser Ser Ser Ser Gly Tyr Pro Val Gly Val Val
```

```
                1               5                  10                 15
Phe Gln Pro Val Gly Ser Gly Gly Val Gln Pro Phe Phe Arg Lys Asn
                20                 25                 30

Trp Leu Arg Leu Thr Trp
            35

<210> SEQ ID NO 146
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Leu Ser Pro Gly Ala Ala Ala Pro Ser Gly Trp Ala Leu Ala Pro Leu
1               5                   10                  15

Gly Asp Thr Met Lys Ile Tyr Met Glu Leu Gln Phe Phe Arg Lys Asn
                20                  25                  30

Trp Leu Arg Leu Thr Trp
            35

<210> SEQ ID NO 147
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Leu Tyr Arg Lys Leu Leu Arg Ser Gln Ser Val Arg Phe Cys Phe
1               5                   10                  15

Gln Gly Leu Leu Glu Asn Ser Ala His Leu Ile Phe Phe Arg Lys Asn
                20                  25                  30

Trp Leu Arg Leu Thr Trp
            35

<210> SEQ ID NO 148
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ala Gln Val Ile Ile Leu Asn His Pro Gly Gln Ile Ser Thr Gly Tyr
1               5                   10                  15

Ala Pro Val Leu Asp Cys His Thr Ala His Ile Phe Phe Arg Lys Asn
                20                  25                  30

Trp Leu Arg Leu Thr Trp
            35

<210> SEQ ID NO 149
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149
```

```
Pro Val Gln Leu Trp Val Ser Ala Thr Pro Ala Gly Ser Pro Val
1               5                   10                  15

Arg Ala Met Ala Ile Tyr Lys Lys Ser Gln His Phe Phe Arg Lys Asn
            20                  25                  30

Trp Leu Arg Leu Thr Trp
        35

<210> SEQ ID NO 150
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asn Ala Phe Asn Pro Leu Asn Ala Ser Ala Ser Leu Pro Pro Ala Ala
1               5                   10                  15

Met Pro Ile Thr Thr Ala Asp Gly Arg Ser Asp Phe Phe Arg Lys Asn
            20                  25                  30

Trp Leu Arg Leu Thr Trp
        35

<210> SEQ ID NO 151
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Val Gly Ser Val Ala Gly Asn Lys Leu Leu Arg Ala Ala Trp Arg Arg
1               5                   10                  15

Ala Ser Leu Ala Ala Thr Ser Leu Ala Leu Gly Phe Phe Arg Lys Asn
            20                  25                  30

Trp Leu Arg Leu Thr Trp
        35

<210> SEQ ID NO 152
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ala Glu Thr Ser Leu Leu Glu Ala Gly Ala Ser Ala Ala Ser Thr Ala
1               5                   10                  15

Ala Ala Leu Glu Asn Leu Gln Val Glu Ala Ser Phe Phe Arg Lys Asn
            20                  25                  30

Trp Leu Arg Leu Thr Trp
        35

<210> SEQ ID NO 153
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153
```

Asn Ser Val Leu Gln Thr Leu Leu Gln Met Arg Ala Ala Lys Ser Ser
1               5                   10                  15

Val Ala Pro Ser Arg Glu Glu Leu Leu Gly Thr Phe Phe Arg Lys Asn
            20                  25                  30

Trp Leu Arg Leu Thr Trp
        35

<210> SEQ ID NO 154
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Phe Thr His Pro Glu Ala Arg Glu Trp Phe Gln Gly Leu Leu Arg
1               5                   10                  15

Arg Leu Arg Leu Arg Tyr Asn Val Thr Ser Phe Phe Phe Arg Lys Asn
            20                  25                  30

Trp Leu Arg Leu Thr Trp
        35

<210> SEQ ID NO 155
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Lys Lys His Asp Val Arg Ser Ile Ile Gly Ser Pro Gly Leu Pro Phe
1               5                   10                  15

Pro Ala Leu His Pro Leu Asp Ile Met Ala Asp Phe Phe Arg Lys Asn
            20                  25                  30

Trp Leu Arg Leu Thr Trp
        35

<210> SEQ ID NO 156
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Ala Gly Arg Pro Arg Pro Val Leu Arg Ser Val Asn Ser Leu Glu Pro
1               5                   10                  15

Ser Gln Val Ile Phe Cys Asn Arg Ser Pro Arg Phe Phe Arg Lys Asn
            20                  25                  30

Trp Leu Arg Leu Thr Trp
        35

<210> SEQ ID NO 157
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 157

Thr Phe Phe Ala Ser Asp Asn Ala Val Asp Ile Thr Thr Leu Thr Asn
1               5                   10                  15

Ser Cys Leu Ser Asn Ser Asp His Ser Arg Asp Phe Arg Lys Asn
                20                  25                  30

Trp Leu Arg Leu Thr Trp
            35

<210> SEQ ID NO 158
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Thr Leu Leu Arg Ser Ser Tyr Val Ala Gln Val Pro Leu Leu Thr Leu
1               5                   10                  15

Cys Thr Arg Gly Pro Pro Glu Glu Asp Ala Pro Phe Arg Lys Asn
                20                  25                  30

Trp Leu Arg Leu Thr Trp
            35

<210> SEQ ID NO 159
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Phe Ser Phe Asn Met Phe Asp His Pro Ile Pro Leu Val Phe Gln
1               5                   10                  15

Asn Arg Phe Ser Thr Gln Tyr Arg Phe Phe Arg Lys Asn Trp Leu Arg
                20                  25                  30

Leu Thr Trp
        35

<210> SEQ ID NO 160
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ala Thr Ala Ala Gly Ser Ser Thr Ile Ser Gln Asp Thr Ile His Leu
1               5                   10                  15

Thr Ser Gly Pro Val Ser Ala Leu Ala Ser Gly Phe Arg Lys Asn
                20                  25                  30

Trp Leu Arg Leu Thr Trp
            35

<210> SEQ ID NO 161
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 161

Ala Cys Ser Ser Ser Tyr Asn Ser Ala Val Met Glu Ser Ser Ser Val
1               5                   10                  15

Asn Val Ser Met Val His Ser Ser Lys Glu Phe Phe Arg Lys Asn
            20                  25                  30

Trp Leu Arg Leu Thr Trp
        35

<210> SEQ ID NO 162
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Val Leu Gln Glu Trp Lys Ala Cys Asp Lys Leu Tyr Asp Val Ala Thr
1               5                   10                  15

Met Arg Thr Thr Gln Leu Thr Tyr Ser Met Glu Phe Phe Arg Lys Asn
            20                  25                  30

Trp Leu Arg Leu Thr Trp
        35

<210> SEQ ID NO 163
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Arg Asp Pro Phe Arg Val Arg Ala Ser Ala Ala Leu Leu Asn Lys Leu
1               5                   10                  15

Tyr Ala Met Gly Leu Val Pro Thr Arg Gly Ser Phe Phe Arg Lys Asn
            20                  25                  30

Trp Leu Arg Leu Thr Trp
        35

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Phe Phe Arg Lys Asn Leu Leu Arg Leu Thr Trp
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Phe Phe Arg Lys Asn Arg Leu Leu Leu Thr Gly
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Phe Phe Arg Lys Asn Trp Leu Leu Leu Thr Trp
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Phe Phe Arg Lys Asn Leu Leu Arg Trp Thr Gly
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Phe Phe Arg Lys Asn Arg Leu Trp Leu Thr Gly
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Phe Phe Arg Lys Phe Trp Leu Arg Leu Thr Trp
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Phe Phe Arg Lys Asn Trp Leu Arg Leu Leu Trp
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Phe Phe Arg Lys Asn Trp Leu Arg Leu Phe Trp
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Phe Phe Arg Lys Asn Trp Leu Arg Leu Lys Trp
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Phe Phe Arg Lys Asn Trp Ile Arg Ile Thr Trp
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Phe Phe Arg Lys Gln Trp Leu Arg Leu Thr Trp
1               5                   10

<210> SEQ ID NO 175
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg
            20                  25

<210> SEQ ID NO 176
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ile Pro Val His Leu Glu Leu Ala Ser Met Thr Asn Met Glu Leu
1               5                   10                  15

```
Met Ser Ser Ile Val His Gln Gln Val Phe Pro Thr
            20                  25

<210> SEQ ID NO 177
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Glu Ala Gly Gln Ser Leu Val Ile Ser Ala Ser Ile Ile Val Phe Asn
1               5                   10                  15

Leu Leu Glu Leu Glu Gly Asp Tyr Arg
            20                  25

<210> SEQ ID NO 178
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg Phe Phe Arg Lys
            20                  25                  30

Asn Leu Leu Arg Leu Thr Gly
        35

<210> SEQ ID NO 179
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gly Ile Pro Val His Leu Glu Leu Ala Ser Met Thr Asn Met Glu Leu
1               5                   10                  15

Met Ser Ser Ile Val His Gln Gln Val Phe Pro Thr Phe Phe Arg Lys
            20                  25                  30

Asn Leu Leu Arg Leu Thr Gly
        35

<210> SEQ ID NO 180
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Ala Gly Gln Ser Leu Val Ile Ser Ala Ser Ile Ile Val Phe Asn
1               5                   10                  15

Leu Leu Glu Leu Glu Gly Asp Tyr Arg Phe Phe Arg Lys Asn Leu Leu
            20                  25                  30

Arg Leu Thr Gly
        35
```

<210> SEQ ID NO 181
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg Phe Phe Arg Lys
            20                  25                  30

Asn Trp Leu Arg Leu Thr Trp
        35

<210> SEQ ID NO 182
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Ile Pro Val His Leu Glu Leu Ala Ser Met Thr Asn Met Glu Leu
1               5                   10                  15

Met Ser Ser Ile Val His Gln Gln Val Phe Pro Thr Phe Phe Arg Lys
            20                  25                  30

Asn Trp Leu Arg Leu Thr Trp
        35

<210> SEQ ID NO 183
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Ala Gly Gln Ser Leu Val Ile Ser Ala Ser Ile Ile Val Phe Asn
1               5                   10                  15

Leu Leu Glu Leu Glu Gly Asp Tyr Arg Phe Phe Arg Lys Asn Trp Leu
            20                  25                  30

Arg Leu Thr Trp
        35

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Lys Phe Val Ala Ala Trp Thr Leu Lys Ala Ala Ala
1               5                   10

<210> SEQ ID NO 185
<211> LENGTH: 24
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 185

Ala Lys Phe Val Ala Ala Trp Thr Leu Lys Ala Ala Phe Phe Arg
1               5                   10                  15

Lys Asn Leu Leu Arg Leu Thr Gly
            20

<210> SEQ ID NO 186
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Lys Phe Val Ala Ala Trp Thr Leu Lys Ala Ala Phe Phe Arg
1               5                   10                  15

Lys Asn Trp Leu Arg Leu Thr Trp
            20

<210> SEQ ID NO 187
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Pro Leu Leu Pro Phe Tyr Pro Pro Asp Glu Ala Leu Glu Ile Gly Leu
1               5                   10                  15

Glu Leu Asn Ser Ser Ala Leu Pro Pro Thr Glu
            20                  25

<210> SEQ ID NO 188
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Pro Leu Leu Pro Phe Tyr Pro Pro Asp Glu Ala Leu Glu Ile Gly Leu
1               5                   10                  15

Glu Leu Asn Ser Ser Ala Leu Pro Pro Thr Glu Phe Phe Arg Lys Asn
            20                  25                  30

Leu Leu Arg Leu Thr Gly
        35

<210> SEQ ID NO 189
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Pro Leu Leu Pro Phe Tyr Pro Pro Asp Glu Ala Leu Glu Ile Gly Leu
```

```
                1               5                   10                  15
Glu Leu Asn Ser Ser Ala Leu Pro Pro Thr Glu Phe Phe Arg Lys Asn
                20                  25                  30

Trp Leu Arg Leu Thr Trp
            35

<210> SEQ ID NO 190
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Glu His Ile His Arg Ala Gly Gly Leu Phe Val Ala Asp Ala Ile Gln
1               5                   10                  15

Val Gly Phe Gly Arg Ile Gly Lys His Phe Trp
                20                  25

<210> SEQ ID NO 191
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu His Ile His Arg Ala Gly Gly Leu Phe Val Ala Asp Ala Ile Gln
1               5                   10                  15

Val Gly Phe Gly Arg Ile Gly Lys His Phe Trp Phe Phe Arg Lys Asn
                20                  25                  30

Leu Leu Arg Leu Thr Gly
            35

<210> SEQ ID NO 192
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu His Ile His Arg Ala Gly Gly Leu Phe Val Ala Asp Ala Ile Gln
1               5                   10                  15

Val Gly Phe Gly Arg Ile Gly Lys His Phe Trp Phe Phe Arg Lys Asn
                20                  25                  30

Trp Leu Arg Leu Thr Trp
            35

<210> SEQ ID NO 193
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asp Lys Pro Leu Arg Arg Asn Asn Ser Tyr Thr Ser Tyr Ile Met Ala
1               5                   10                  15
```

Ile Cys Gly Met Pro Leu Asp Ser Phe Arg Ala
            20                  25

<210> SEQ ID NO 194
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Lys Pro Leu Arg Arg Asn Asn Ser Tyr Thr Ser Tyr Ile Met Ala
1               5                   10                  15

Ile Cys Gly Met Pro Leu Asp Ser Phe Arg Ala Phe Phe Arg Lys Asn
            20                  25                  30

Leu Leu Arg Leu Thr Gly
        35

<210> SEQ ID NO 195
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Asp Lys Pro Leu Arg Arg Asn Asn Ser Tyr Thr Ser Tyr Ile Met Ala
1               5                   10                  15

Ile Cys Gly Met Pro Leu Asp Ser Phe Arg Ala Phe Phe Arg Lys Asn
            20                  25                  30

Trp Leu Arg Leu Thr Trp
        35

<210> SEQ ID NO 196
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Val Ile Gln Thr Ser Lys Tyr Tyr Met Arg Asp Val Ile Ala Ile
1               5                   10                  15

Glu Ser Ala Trp Leu Leu Glu Leu Ala Pro His
            20                  25

<210> SEQ ID NO 197
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Ile Gln Thr Ser Lys Tyr Tyr Met Arg Asp Val Ile Ala Ile
1               5                   10                  15

Glu Ser Ala Trp Leu Leu Glu Leu Ala Pro His Phe Phe Arg Lys Asn
            20                  25                  30

Leu Leu Arg Leu Thr Gly
        35

```
<210> SEQ ID NO 198
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Val Ile Gln Thr Ser Lys Tyr Tyr Met Arg Asp Val Ile Ala Ile
1               5                   10                  15

Glu Ser Ala Trp Leu Leu Glu Leu Ala Pro His Phe Phe Arg Lys Asn
            20                  25                  30

Trp Leu Arg Leu Thr Trp
        35

<210> SEQ ID NO 199
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Val Ile Leu Pro Gln Ala Pro Ser Gly Pro Ser Tyr Ala Thr Tyr Leu
1               5                   10                  15

Gln Pro Ala Gln Ala Gln Met Leu Thr Pro Pro
            20                  25

<210> SEQ ID NO 200
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Val Ile Leu Pro Gln Ala Pro Ser Gly Pro Ser Tyr Ala Thr Tyr Leu
1               5                   10                  15

Gln Pro Ala Gln Ala Gln Met Leu Thr Pro Pro Phe Phe Arg Lys Asn
            20                  25                  30

Leu Leu Arg Leu Thr Gly
        35

<210> SEQ ID NO 201
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Val Ile Leu Pro Gln Ala Pro Ser Gly Pro Ser Tyr Ala Thr Tyr Leu
1               5                   10                  15

Gln Pro Ala Gln Ala Gln Met Leu Thr Pro Pro Phe Phe Arg Lys Asn
            20                  25                  30

Trp Leu Arg Leu Thr Trp
        35
```

```
<210> SEQ ID NO 202

<400> SEQUENCE: 202

000

<210> SEQ ID NO 203

<400> SEQUENCE: 203

000

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asn Trp Leu Leu Leu Thr Trp
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Asn Leu Leu Arg Trp Thr Gly
1               5

<210> SEQ ID NO 206

<400> SEQUENCE: 206

000

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Phe Trp Leu Arg Leu Thr Trp
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asn Trp Leu Arg Leu Leu Trp
1               5

<210> SEQ ID NO 209
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Asn Trp Leu Arg Leu Phe Trp
1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asn Trp Leu Arg Leu Lys Trp
1               5

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Asn Trp Ile Arg Ile Thr Trp
1               5

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Trp Leu Arg Leu Thr Trp
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Asn Trp Leu Lys Leu Lys Trp
1               5

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Asn Trp Leu Lys Leu Arg Trp
```

```
1               5
```

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Asn Trp Leu Lys Leu Trp Lys
1               5
```

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Asn Leu Leu Arg Leu Thr Trp Phe Phe Arg Lys
1               5                   10
```

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Asn Arg Leu Leu Leu Thr Gly Phe Phe Arg Lys
1               5                   10
```

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Asn Trp Leu Leu Leu Thr Trp Phe Phe Arg Lys
1               5                   10
```

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Asn Leu Leu Arg Trp Thr Gly Phe Phe Arg Lys
1               5                   10
```

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Asn Arg Leu Trp Leu Thr Gly Phe Phe Arg Lys
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Phe Trp Leu Arg Leu Thr Trp Phe Phe Arg Lys
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Asn Trp Leu Arg Leu Leu Trp Phe Phe Arg Lys
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Asn Trp Leu Arg Leu Phe Trp Phe Phe Arg Lys
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asn Trp Leu Arg Leu Lys Trp Phe Phe Arg Lys
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asn Trp Ile Arg Ile Thr Trp Phe Phe Arg Lys
1               5                   10

<210> SEQ ID NO 226

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Trp Leu Arg Leu Thr Trp Phe Phe Arg Lys
1               5                   10

<210> SEQ ID NO 227
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asn Trp Leu Lys Leu Lys Trp Phe Phe Arg Lys
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Asn Trp Leu Lys Leu Arg Trp Phe Phe Arg Lys
1               5                   10

<210> SEQ ID NO 229
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Asn Trp Leu Lys Leu Trp Lys Phe Phe Arg Lys
1               5                   10

<210> SEQ ID NO 230
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Val Ser Gly Leu Glu Gln Leu Glu Ser Ile Ile Asn Phe Glu Lys
1               5                   10                  15

Leu Thr Glu Trp Thr Ser Ser Asn Val Met Glu Phe Phe Arg Lys Asn
            20                  25                  30

Leu Leu Arg Leu Thr Gly
        35

<210> SEQ ID NO 231
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 231

Glu Val Ser Gly Leu Glu Gln Leu Glu Ser Ile Ile Asn Phe Glu Lys
1               5                   10                  15

Leu Thr Glu Trp Thr Ser Ser Asn Val Met Glu Phe Phe Arg Lys Asn
            20                  25                  30

Trp Leu Arg Leu Thr Trp
        35

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (4)..(4)
<223> OTHER INFORMATION: Leu, Arg, or Lys
<220> FEATURE:
<221> NAME/KEY: MOD_RES
<222> LOCATION: (5)..(5)
<223> OTHER INFORMATION: Leu or Ile
<220> FEATURE:
<221> NAME/KEY: MOD_RES
<222> LOCATION: (6)..(6)
<223> OTHER INFORMATION: Thr, Leu, Phe, Lys, Arg, or Trp
<220> FEATURE:
<221> NAME/KEY: MOD_RES
<222> LOCATION: (7)..(7)
<223> OTHER INFORMATION: Trp or Lys

<400> SEQUENCE: 232

Asn Trp Xaa Xaa Xaa Xaa Xaa
1               5

<210> SEQ ID NO 233
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Leu or Ile
<220> FEATURE:
<221> NAME/KEY: MOD_RES
<222> LOCATION: (8)..(8)
<223> OTHER INFORMATION: Leu, Arg, or Lys
<220> FEATURE:
<221> NAME/KEY: MOD_RES
<222> LOCATION: (9)..(9)
<223> OTHER INFORMATION: Leu or Ile
<220> FEATURE:
<221> NAME/KEY: MOD_RES
<222> LOCATION: (10)..(10)
<223> OTHER INFORMATION: Thr, Leu, Phe, Lys, Arg, or Trp
<220> FEATURE:
<221> NAME/KEY: MOD_RES
<222> LOCATION: (11)..(11)
<223> OTHER INFORMATION: Trp or Lys

<400> SEQUENCE: 233
```

```
Phe Phe Arg Lys Asn Trp Xaa Xaa Xaa Xaa Xaa
1               5                   10
```

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (4)..(4)
<223> OTHER INFORMATION: Leu, Arg, or Lys
<220> FEATURE:
<221> NAME/KEY: MOD_RES
<222> LOCATION: (5)..(5)
<223> OTHER INFORMATION: Leu or Ile
<220> FEATURE:
<221> NAME/KEY: MOD_RES
<222> LOCATION: (6)..(6)
<223> OTHER INFORMATION: Thr, Leu, Phe, Lys, Arg, or Trp
<220> FEATURE:
<221> NAME/KEY: MOD_RES
<222> LOCATION: (7)..(7)
<223> OTHER INFORMATION: Trp or Lys

<400> SEQUENCE: 234

```
Asn Trp Xaa Xaa Xaa Xaa Xaa Phe Phe Arg Lys
1               5                   10
```

HEAT SHOCK PROTEIN-BINDING PEPTIDE COMPOSITIONS AND METHODS OF USE THEREOF

RELATED APPLICATIONS

This application claims priority to U.S. Provisional Patent Application Nos. 62/663,083, filed Apr. 26, 2018, and 62/692,009, filed Jun. 29, 2018, the entire disclosure of each of which is hereby incorporated herein by reference.

SEQUENCE LISTING

The instant application contains a Sequence Listing which has been filed electronically in ASCII format and is hereby incorporated by reference in its entirety. Said ASCII copy, created on Jul. 26, 2019, is named 611505_AGBW-121_SL.txt and is 79,155 bytes in size.

1. FIELD

The invention relates to heat shock protein (HSP)-binding peptide compositions, and uses of such compositions as immunotherapeutics (e.g., cancer vaccines).

2. BACKGROUND

Immunotherapies are becoming important tools in the treatment of cancer. One immunotherapy approach involves the use of therapeutic cancer vaccines comprising cancer-specific antigenic peptides that actively educate a patient's immune system to target and destroy cancer cells. However, the generation of such therapeutic cancer vaccines is limited by the immunogenicity of cancer-specific antigenic peptides.

Accordingly, there is a need in the art for improved methods of generating highly immunogenic cancer-specific antigenic peptides and for creating effective anti-cancer vaccines comprising these peptides.

3. SUMMARY OF INVENTION

The instant disclosure provides polypeptides and compositions comprising novel HSP-binding peptides. Such polypeptides and compositions are particularly useful as immunotherapeutics (e.g., cancer vaccines). Also provided are methods of inducing a cellular immune response using such polypeptides and compositions, methods of treating a disease using such polypeptides and compositions, kits comprising such polypeptides and compositions, and methods of making such compositions.

Accordingly, in one aspect, the disclosure provides an isolated polypeptide comprising a heat shock protein (HSP)-binding peptide comprising the amino acid sequence of $X_1LX_2LTX_3$ (SEQ ID NO: 1), wherein $X_1$ is W or F; $X_2$ is R or K; and $X_3$ is W, F, or G. In another aspect, the disclosure provides an isolated polypeptide comprising an HSP-binding peptide comprising the amino acid sequence of $NWX_1X_2X_3X_4X_5$ (SEQ ID NO: 232), wherein $X_1$ is L or I; $X_2$ is L, R, or K; $X_3$ is L or I; $X_4$ is T, L, F, K, R, or W; and $X_5$ is W or K.

In certain embodiments, the HSP-binding peptide comprises the amino acid sequence of: $NX_1LX_2LTX_3$ (SEQ ID NO: 2), wherein $X_1$ is W or F; $X_2$ is R or K; and $X_3$ is W, F, or G; $WLX_1LTX_2$ (SEQ ID NO: 3), wherein $X_1$ is R or K; and $X_2$ is W or G; or $NWLX_1LTX_2$ (SEQ ID NO: 4), wherein $X_1$ is R or K; and $X_2$ is W or G.

In certain embodiments, the HSP-binding peptide comprises an amino acid sequence selected from the group consisting of SEQ ID NOs: 5-12, 98-113, 204, 205, and 207-215. In certain embodiments, the amino acid sequence of the HSP-binding peptide consists of an amino acid sequence selected from the group consisting of SEQ ID NOs: 5-12, 98-113, 204, 205, and 207-215. In certain embodiments, the HSP-binding peptide comprises the amino acid sequence of SEQ ID NO: 6. In certain embodiments, the amino acid sequence of the HSP-binding peptide consists of the amino acid sequence of SEQ ID NO: 6. In certain embodiments, the HSP-binding peptide is no more than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues in length.

In certain embodiments, the polypeptide further comprises an antigenic peptide comprising one or more major histocompatibility complex (MHC)-binding epitopes. In certain embodiments, the MHC-binding epitope binds to an MHC I molecule with an $IC_{50}$ of 500 nM or less. In certain embodiments, the MHC-binding epitope binds to an MHC II molecule with an $IC_{50}$ of 1000 nM or less.

In certain embodiments, the MHC-binding epitope is from a cancer cell. In certain embodiments, the MHC-binding epitope comprises an amino acid mutation or a gene fusion mutation of the cancer cell. In certain embodiments, the amino acid mutation is a substitution, deletion, or insertion mutation. In certain embodiments, the amino acid mutation or gene fusion mutation is at or about the middle of the antigenic peptide. In certain embodiments, the amino acid mutation or gene fusion mutation is at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of the amino acid sequence of the antigenic peptide.

In certain embodiments, the MHC-binding epitope is from a pathogenic microbe. In certain embodiments, the pathogenic microbe is a virus. In certain embodiments, the virus is a human papillomavirus (HPV). In certain embodiments, the antigenic peptide comprises an amino acid sequence selected from the group consisting of SEQ ID NOs: 38-53.

In another aspect, the instant disclosure provides an isolated polypeptide comprising an HSP-binding peptide and an antigenic peptide comprising an amino acid sequence selected from the group consisting of SEQ ID NOs: 38-53. In certain embodiments, the amino acid sequence of the antigenic peptide consists of an amino acid sequence selected from the group consisting of SEQ ID NOs: 38-53. In certain embodiments, the HSP-binding peptide comprises an amino acid sequence selected from the group consisting of SEQ ID NOs: 1-12, 98-113, 204, 205, 207-215, and 232. In certain embodiments, the amino acid sequence of the HSP-binding peptide consists of an amino acid sequence selected from the group consisting of SEQ ID NOs: 1-12, 98-113, 204, 205, 207-215, and 232.

In certain embodiments, the MHC-binding epitope comprises a modified amino acid residue. In certain embodiments, the modified amino acid residue is a Tyr, Ser, Thr, Arg, Lys, or His that has been phosphorylated on a side chain hydroxyl or amine. In certain embodiments, the modified amino acid residue is a mimetic of a Tyr, Ser, Thr, Arg, Lys, or His amino acid that has been phosphorylated on a side chain hydroxyl or amine. In some embodiments, the mimetic is a non-hydrolyzable analogue of a phosphorylated residue. In certain embodiments, the modified amino acid residue is an Asn that has been glycosylated on a side chain amide, a Ser or Thr that has been glycosylated on a side chain hydroxyl, a Lys or Arg that has been methylated on a side chain amino, a Lys that has been acetylated on a side chain amino, an N-terminal residue that has been acetylated on the α-amino, or a C-terminal residue that has been amidated on the α-carboxyl. In certain embodiments, the modified amino acid residue is at or about the middle of the antigenic peptide. In certain embodiments, the modified amino acid residue is at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of the amino acid sequence of the antigenic peptide.

In certain embodiments, the HSP-binding peptide is linked to the antigenic peptide via a chemical linker. In certain embodiments, the HSP-binding peptide is linked to the antigenic peptide via a peptide linker. In certain embodiments, the peptide linker comprises the amino acid sequence of FFRK (SEQ ID NO: 13) or FR.

In certain embodiments, the HSP-binding peptide is at the C-terminus of the polypeptide. In certain embodiments, the polypeptide comprises the amino acid sequence of:
(a) FFRKX$_1$LX$_2$LTX$_3$ (SEQ ID NO: 14), wherein X$_1$ is W or F; X$_2$ is R or K; and X$_3$ is W, F, or G;
(b) FFRKNX$_1$LX$_2$LTX$_3$ (SEQ ID NO: 15), wherein X$_1$ is W or F; X$_2$ is R or K; and X$_3$ is W, F, or G;
(c) FFRKWLX$_1$LTX$_2$ (SEQ ID NO: 16), wherein X$_1$ is R or K; and X$_2$ is W or G; (d) FFRKNWLX$_1$LTX$_2$ (SEQ ID NO: 17), wherein X$_1$ is R or K; and X$_2$ is W or G; or
(e) FFRKNWX$_1$X$_2$X$_3$X$_4$X$_5$ (SEQ ID NO: 233), wherein, X$_1$ is L or I; X$_2$ is L, R, or K; X$_3$ is L or I; X$_4$ is T, L, F, K, R, or W; and X$_5$ is W or K, at the C-terminus of the polypeptide. In certain embodiments, the polypeptide comprises an amino acid sequence selected from the group consisting of SEQ ID NOs: 18-25, 71-75, 166, 167, 173, and 174, at the C-terminus of the polypeptide.

In certain embodiments, the HSP-binding peptide is at the N-terminus of the polypeptide. In certain embodiments, the polypeptide comprises the amino acid sequence of:
(a) X$_1$LX$_2$LTX$_3$FFRK (SEQ ID NO: 26), wherein X$_1$ is W or F; X$_2$ is R or K; and X$_3$ is W, F, or G;
(b) NX$_1$LX$_2$LTX$_3$FFRK (SEQ ID NO: 27), wherein X$_1$ is W or F; X$_2$ is R or K; and X$_3$ is W, F, or G;
(c) WLX$_1$LTX$_2$FFRK (SEQ ID NO: 28), wherein X$_1$ is R or K; and X$_2$ is W or G;
(d) NWLX$_1$LTX$_2$FFRK (SEQ ID NO: 29), wherein X$_1$ is R or K; and X$_2$ is W or G; or
(e) FFRKNWX$_1$X$_2$X$_3$X$_4$X$_5$ (SEQ ID NO: 233), wherein X$_1$ is L or I; X$_2$ is L, R, or K; X$_3$ is L or I; X$_4$ is T, L, F, K, R, or W; and X$_5$ is W or K, at the N-terminus of the polypeptide. In certain embodiments, the polypeptide comprises an amino acid sequence selected from the group consisting of SEQ ID NOs: 30-37, and 216-229, at the N-terminus of the polypeptide.

In certain embodiments, the polypeptide is 12 to 50 amino acids in length (e.g., 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length). In certain embodiments, the polypeptide is 20 to 40 amino acids in length.

In certain embodiments, the polypeptide comprises an amino acid sequence selected from the group consisting of SEQ ID NOs: 54-69. In certain embodiments, the amino acid sequence of the polypeptide consists of an amino acid sequence selected from the group consisting of SEQ ID NOs: 54-69.

In certain embodiments, the polypeptide is chemically synthesized.

In another aspect, the instant disclosure provides a composition comprising a complex of the polypeptide disclosed herein and a purified stress protein. In certain embodiments, the stress protein is selected from the group consisting of Hsc70, Hsp70, Hsp90, Hsp110, Grp170, Gp96, Calreticulin, and a mutant or fusion protein thereof. In certain embodiments, the stress protein is Hsc70. In certain embodiments, the stress protein is human Hsc70. In certain embodiments, the stress protein is a recombinant protein.

In another aspect, the instant disclosure provides a composition comprising a plurality of the polypeptides as disclosed herein, optionally further comprising a purified stress protein as disclosed herein. In certain embodiments, the composition comprises 2-20 different polypeptides as disclosed herein. In certain embodiments, each of the different polypeptides comprises the same HSP-binding peptide and a different antigenic peptide.

In certain embodiments, the antigenic peptide of each one of the polypeptides comprises an amino acid sequence selected from the group consisting of SEQ ID NOs: 38-53. In certain embodiments, the composition comprises at least 2, 3, 4, 5, 6, 7, 8, 9, 10, 11, 12, 13, 14, 15, or 16 different antigenic peptides. In certain embodiments, each one of the polypeptides comprises an amino acid sequence selected from the group consisting of SEQ ID NOs: 54-69. In certain embodiments, the amino acid sequence of each one of the polypeptides consists of an amino acid sequence selected from the group consisting of SEQ ID NOs: 54-69. In certain embodiments, the composition comprises at least 2, 3, 4, 5, 6, 7, 8, 9, 10, 11, 12, 13, 14, 15, or 16 different polypeptides. In certain embodiments, the total amount of the polypeptide(s) in the composition is about 0.1 to 20 nmol. In certain embodiments, the total amount of the polypeptide(s) in the composition is about 3, 4, 5, or 6 nmol. In certain embodiments, the amount of the stress protein in the composition is about 10 µg to 600 µg. In certain embodiments, the amount of the stress protein in the composition is about 250 µg to 290 µg.

In certain embodiments, the molar ratio of the polypeptide(s) to the stress protein is about 0.5:1 to 5:1. In certain embodiments, the molar ratio of the polypeptide(s) to the stress protein is about 1:1 to 2:1. In certain embodiments, the molar ratio of the polypeptide(s) to the stress protein is about 1:1, 1.25:1, or 1.5:1.

In certain embodiments, the total amount of the polypeptide(s) and stress protein in the composition is about 10 µg to 600 µg. In certain embodiments, the total amount of the polypeptide(s) and stress protein in the composition is about 300 µg.

In certain embodiments, the composition further comprises an adjuvant. In certain embodiments, the adjuvant comprises a saponin or an immunostimulatory nucleic acid. In certain embodiments, the adjuvant comprises QS-21. In certain embodiments, the amount of the QS-21 in the composition is about 10 µg, 25 µg, or 50 µg. In certain embodiments, the adjuvant comprises a Toll-like receptor (TLR) agonist. In certain embodiments, the TRL agonist is an agonist of TLR4. In certain embodiments, the TRL agonist is an agonist of TLR7 and/or TLR8. In certain embodiments, the TRL agonist is an agonist of TLR9. In certain embodiments, the TRL agonist is an agonist of TLR5.

In certain embodiments, the composition is a pharmaceutical composition comprising a pharmaceutically acceptable carrier or excipient. In certain embodiments, the composition is in a unit dosage form.

In another aspect, the instant disclosure provides a method of inducing a cellular immune response to an antigenic peptide in a subject, the method comprising administering to the subject an effective amount of a composition or a unit dosage form as disclosed herein. In certain embodiments, the subject has cancer. In certain embodiments, the subject has an infection of a pathogenic microbe.

In another aspect, the instant disclosure provides a method of treating a disease in a subject, the method comprising administering to the subject an effective amount of a composition or a unit dosage form as disclosed herein. In certain embodiments, the disease is cancer. In certain embodiments, the disease is an infection of a pathogenic microbe.

In certain embodiments, the MHC-binding epitope is present in the subject's cancer cells. In certain embodiments, the MHC-binding epitope is present in the pathogenic microbe.

In certain embodiments, the composition or unit dosage form is administered to the subject weekly for four weeks. In certain embodiments, at least two further doses of the composition or unit dosage form are administered biweekly to the subject after the four weekly doses. In certain embodiments, at least one booster dose of the composition or unit dosage form is administered three months after the final weekly or biweekly dose. In certain embodiments, the composition or unit dosage form is further administered every three months for at least 1 year.

In certain embodiments, the method further comprises administering to the subject lenalidomide, dexamethasone, interleukin-2, recombinant interferon alfa-2b, or PEG-interferon alfa-2b. In certain embodiments, the method further comprises administering to the subject an indoleamine dioxygenase-1 (IDO-1) inhibitor. In certain embodiments, the IDO-1 inhibitor is 4-amino-N-(3-chloro-4-fluorophenyl)-N'-hydroxy-1,2,5-oxadiazole-3-carboximidamide. In certain embodiments, the method further comprises administering to the subject an immune checkpoint antibody. In certain embodiments, the immune checkpoint antibody is selected from the group consisting of an agonistic anti-GITR antibody, an agonistic anti-OX40 antibody, an antagonistic anti-PD-1 antibody, an antagonistic anti-CTLA-4 antibody, an antagonistic anti-TIM-3 antibody, an antagonistic anti-LAG-3 antibody, an antagonistic anti-TIGIT antibody, an agonistic anti-CD96 antibody, an antagonistic anti-VISTA antibody, an antagonistic anti-CD73 antibody, an agonistic anti-CD137 antibody, an antagonist anti-CEACAM1 antibody, an agonist anti-ICOS antibody, and or an antigen-binding fragment thereof.

In another aspect, the instant disclosure provides a kit comprising a first container containing the polypeptide as disclosed herein, and a second container containing a purified stress protein capable of binding to the polypeptide.

In certain embodiments, the first container contains 2-20 different polypeptides as disclosed herein. In certain embodiments, each of the different polypeptides comprises the same HSP-binding peptide and a different antigenic peptide. In certain embodiments, the total amount of the polypeptide(s) in the first container is about 0.1 to 20 nmol. In certain embodiments, the total amount of the polypeptide(s) in the first container is about 3, 4, 5, or 6 nmol.

In certain embodiments, the first container contains a single polypeptide as disclosed here in. In certain embodiments, the first container contains at least 20 different polypeptides as disclosed herein. In certain embodiments, each of the different polypeptides comprises the same HSP-binding peptide and a different antigenic peptide. In certain embodiments, the total amount of the polypeptide(s) in the first container is about 0.1 to 20 nmol. In certain embodiments, the total amount of the polypeptide(s) in the first container is about 3, 4, 5, or 6 nmol.

In certain embodiments, the stress protein is selected from the group consisting of Hsc70, Hsp70, Hsp90, Hsp110, Grp170, Gp96, Calreticulin, and a mutant thereof. In certain embodiments, the stress protein is Hsc70. In certain embodiments, the stress protein is human Hsc70. In certain embodiments, the stress protein is a recombinant protein. In certain embodiments, the amount of the stress protein in the second container is about 10 µg to 600 µg. In certain embodiments, the amount of the stress protein in the second container is about 250 µg to 290 µg.

In certain embodiments, the molar ratio of the polypeptide to the stress protein is about 0.5:1 to 5:1. In certain embodiments, the molar ratio of the polypeptide to the stress protein is about 1:1 to 2:1. In certain embodiments, the molar ratio of the polypeptide to the stress protein is about 1:1, 1.25:1, or 1.5:1. In certain embodiments, the total amount of the polypeptide(s) in the first container and the stress protein in the second container is about 10 µg to 600 µg. In certain embodiments, the total amount of the polypeptide(s) in the first container and the stress protein in the second container is 300 µg.

In certain embodiments, the kit further comprises a third container containing an adjuvant. In certain embodiments, the adjuvant comprises a saponin or an immunostimulatory nucleic acid. In certain embodiments, the adjuvant comprises QS-21. In certain embodiments, the amount of the QS-21 in the third container is about 10 µg, 25 µg, or 50 µg. In certain embodiments, the adjuvant comprises a TLR agonist. In certain embodiments, the TRL agonist is an agonist of TLR4. In certain embodiments, the TRL agonist is an agonist of TLR7 and/or TLR8. In certain embodiments, the TRL agonist is an agonist of TLR9. In certain embodiments, the TRL agonist is an agonist of TLR5.

In another aspect, the instant disclosure provides a method of making a vaccine, the method comprising mixing one or more polypeptides as disclosed herein with a purified stress protein under suitable conditions such that the purified stress protein binds to at least one of the polypeptides. In certain embodiments, the stress protein is selected from the group consisting of Hsc70, Hsp70, Hsp90, Hsp110, Grp170, Gp96, Calreticulin, and a mutant thereof. In certain embodiments, the stress protein is Hsc70. In certain embodiments, the stress protein is human Hsc70. In certain embodiments, the stress protein is a recombinant protein. In certain embodiments, the molar ratio of the polypeptide to the stress protein is about 0.5:1 to 5:1. In certain embodiments, the molar ratio of the polypeptide to the stress protein is about 1:1 to 2:1. In certain embodiments, the molar ratio of the polypeptide to the stress protein is about 1:1, 1.25:1, or 1.5:1. In certain embodiments, the suitable conditions comprise a temperature of about 37° C.

4. BRIEF DESCRIPTION OF THE DRAWINGS

FIG. 1 is an exemplary size exclusion chromatography (SEC) chromatogram showing the UV absorbance of uncomplexed Hsc70 (top) and peptide complexed Hsc70 (bottom). "C", "D", "T", and "HMW" indicate the segments of the chromatogram corresponding to peptide-Hsc70 complexes, Hsc70 dimers, Hsc70 trimers, and high molecular weight oligomeric Hsc70 species, respectively. "Msh" refers to a monomer shoulder.

FIG. 2 is a chromatogram showing the UV absorbance of PEP006 mixed with Hsc70 at a range of molar ratios from 0.25:1 to 3:1, wherein the compositions in the mixture were separated by size exclusion chromatography.

FIG. 3A is a chromatogram showing the UV absorbance of a polypeptide comprising PEP006 mixed with Hsc70 at a range of molar ratios from 0.125:1 to 4:1, wherein the compositions in the mixture were separated by size exclusion chromatography. FIG. 3B is a graph showing percent complexation with Hsc70 for a PEP006-containing polypeptide, over a range of polypeptide:Hsc70 molar ratios from 0.125:1 to 4:1, as calculated from size exclusion chromatography traces similar to those in FIG. 3A. Three independent experiments are shown.

FIG. 4A is a graph showing percent complexation with Hsc70 for five different peptides, where each of the five different peptides was synthesized in three forms: one with a C-terminal PEP001 sequence, one with a C-terminal PEP006 sequence, and one without a C-terminal HSP-binding peptide ("Naked Peptide"). FIG. 4B is a graph showing percent complexation with Hsc70 for six different peptides, where each of the six different peptides was synthesized in two forms: one with a C-terminal PEP001 sequence and one with a C-terminal PEP006 sequence.

FIGS. 5A and 5B are graphs showing the relative number of IFNγ-producing splenocytes from mice immunized with vaccines comprising PEP001- or PEP006-containing HPV pooled peptides, or HPV pooled peptides not linked to an HSP-binding peptide (naked HPV peptides), as free peptides or mixed with Hsc70 protein at 2:1 or 1:1 ratio (n=3 mice per treatment group).

Figure 7A:
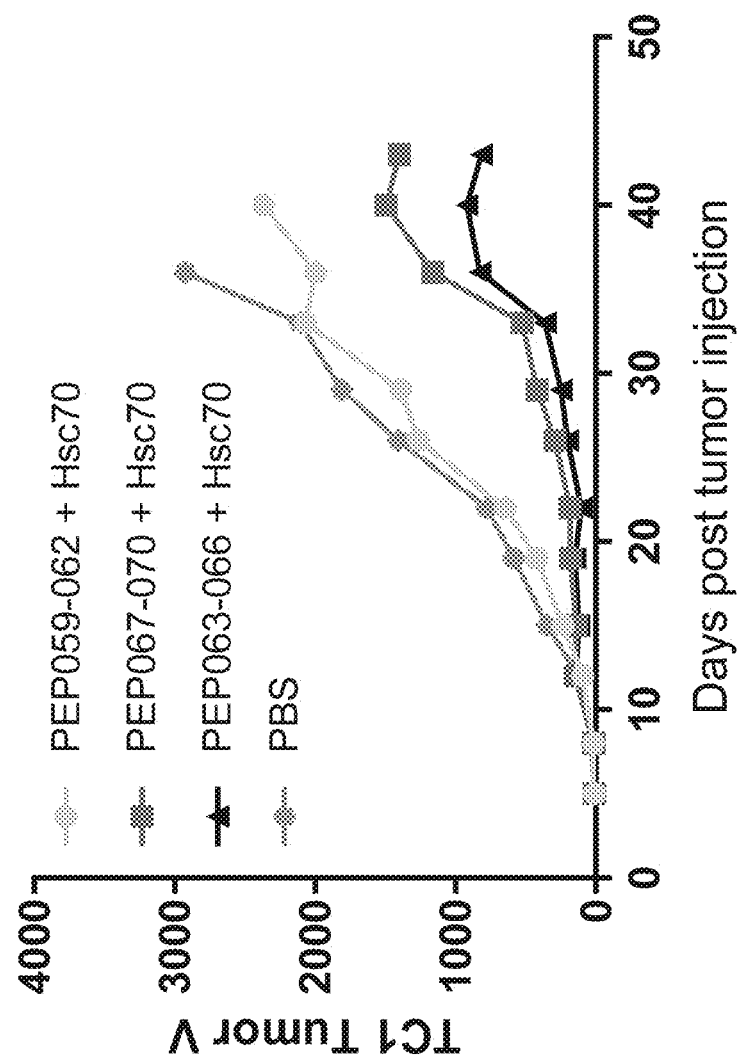
Figure 7C:
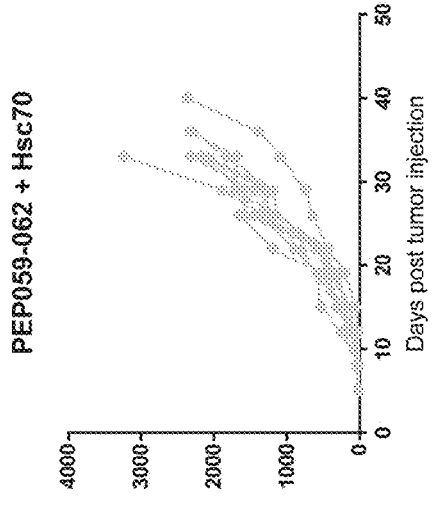

FIG. 7A is a graph showing the mean volumes of tumors in a syngeneic mouse tumor model, wherein the mice were immunized with vaccines comprising PEP001-containing HPV peptides ("PEP067-070"), PEP006-containing HPV peptides ("PEP063-066"), or naked HPV peptides ("PEP059-062"), in each case mixed with Hsc70 protein as described in Section 6.2.2 herein, or PBS as negative control (n=10 mice per treatment group). FIGS. 7B-7E show the tumor volume of each mouse in these four treatment groups. FIG. 7F shows a set of survival curves of the mice.

FIG. 8A is a graph showing the mean volumes of tumors in a syngeneic mouse tumor model, wherein the mice were immunized with vaccines comprising a new pool of PEP006-containing HPV peptides ("PEP071-086") or a previously tested pool of PEP006-containing HPV peptides ("PEP063-066"), in each case mixed with Hsc70 protein as described in Section 6.2.3 herein, or PBS as negative control (n=13 mice per treatment group; error bars: standard deviations). FIG. 8B shows a set of survival curves of the mice.

FIG. 9A is a series of graphs showing tumor growth kinetics in individual mice treated with two different formulations of HSC70-based vaccine loaded with 16 different HPV peptides comprising PEP006 as compared to PBS. FIG. 9B is a graph showing group mean tumor growth kinetics of mice in the same mice. FIG. 9C is a graph showing overall survival in the same experiment.

Figure 10B:
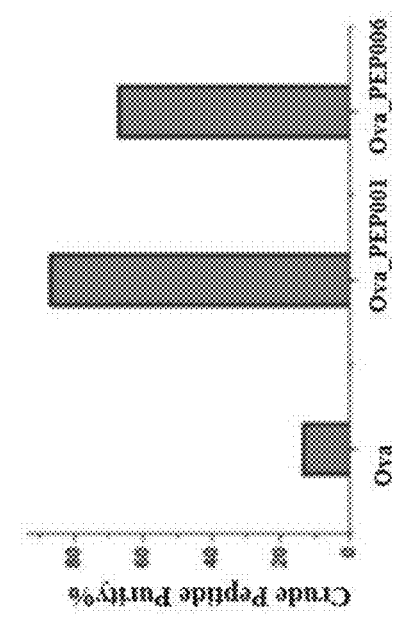
Figure 10A:
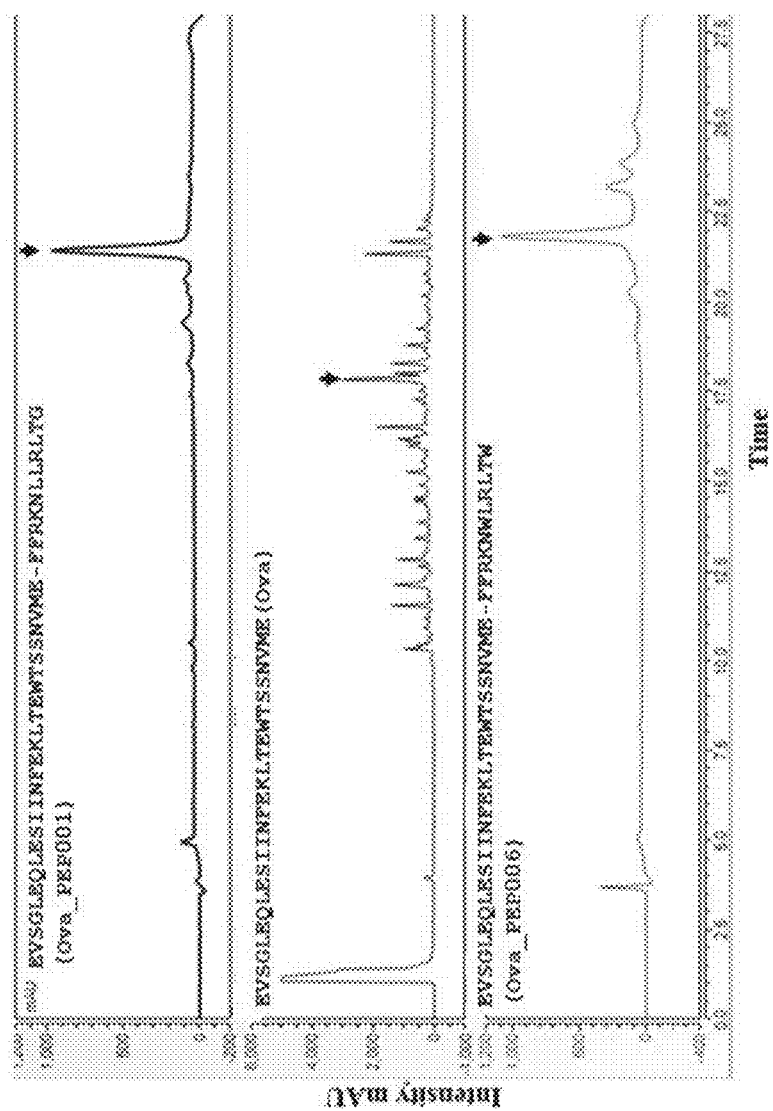

FIG. 10A is a series of chromatograms showing the reverse phase chromatography signals of the chemical synthesis products of an Ova peptide, naked (SEQ ID NO:97) or linked with PEP001 (SEQ ID NO:230) or PEP006 (SEQ ID NO:231). The arrows indicate the retention time of the pure peptides.

FIG. 10B is a graph showing quantification of the signals in FIG. 10A.

Figure 11:
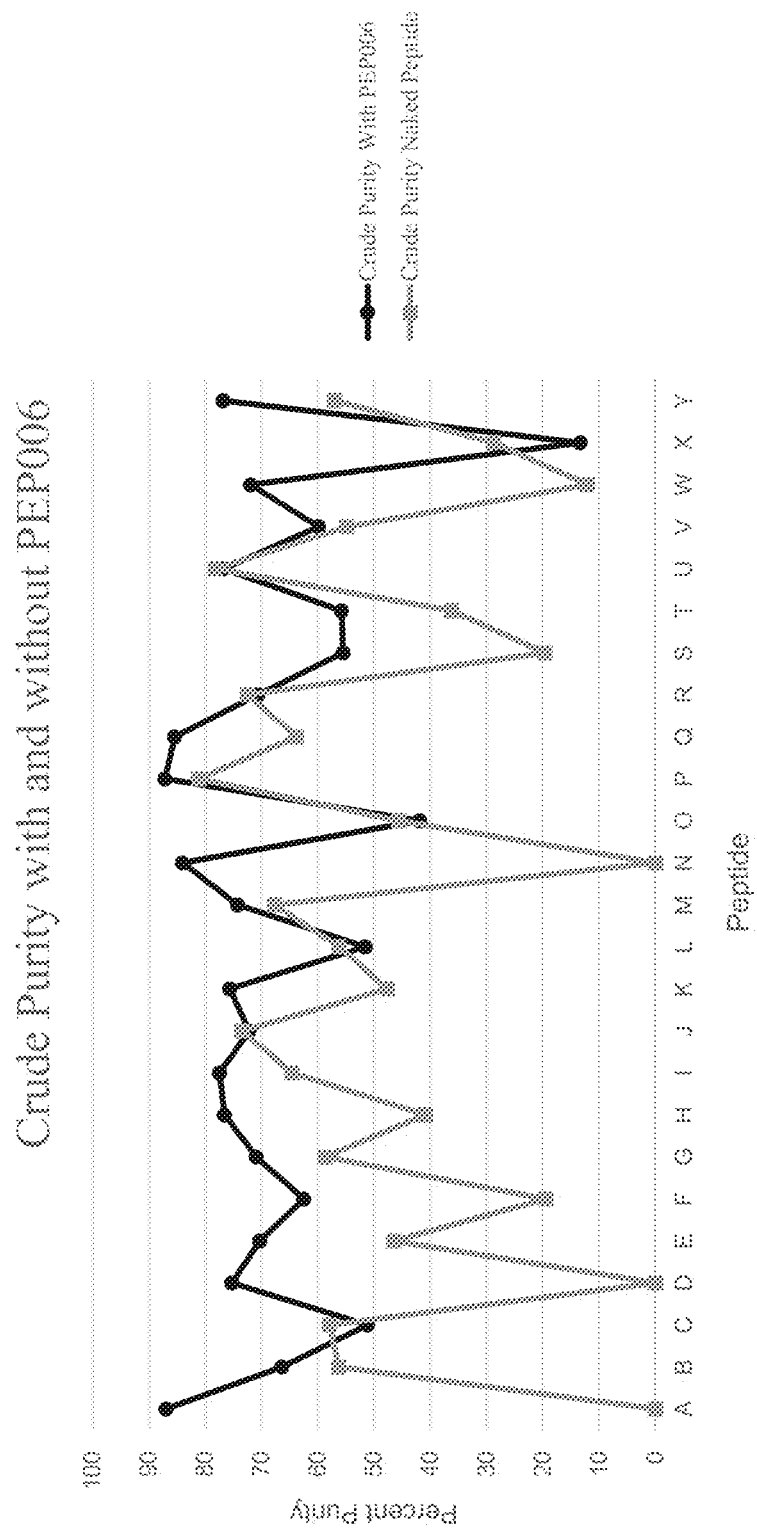

FIG. 11 is a graph showing crude purity of naked peptides (A-Y) versus the same peptides (A-Y) with a C-terminal PEP006 sequence.

5. DETAILED DESCRIPTION

The instant disclosure provides polypeptides and compositions comprising novel HSP-binding peptides. Such polypeptides and compositions are particularly useful as immunotherapeutics (e.g., cancer vaccines). Also provided are methods of inducing a cellular immune response using such polypeptides and compositions, methods of treating a disease using such polypeptides and compositions, kits comprising such polypeptides and compositions, and methods of making such compositions.

5.1 Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the recited value or range remain within the intended meaning of the recited value or range.

As used herein, the term "polypeptide" refers to a non-naturally occurring polymer comprising a peptide of six or more amino acid residues. A polypeptide can further comprise one or more non-amino-acid-residue structures. In certain embodiments, a polypeptide comprises a chemical linker. In certain embodiments, a polypeptide comprises a chemical linker linking two portions of the polypeptide. In certain embodiments, a polypeptide does not comprise the entire amino acid sequence of a protein (e.g., a naturally occurring protein) comprising the amino acid sequence of SEQ ID NO: 1. In certain embodiments, a polypeptide does not comprise an amino acid sequence comprising more than 6, 7, 8, 9, 10, 11, 12, 13, 14, 15, 20, 25, 30, 35, 40, 45, 50, 55, 60, 65, 70, 75, 80, 85, 90, 95, or 100 contiguous amino acids of a protein (e.g., a naturally occurring protein) that comprises the amino acid sequence of SEQ ID NO: 1.

As used herein, the term "isolated polypeptide" refers to a polypeptide that is separated from one or more molecules present after the expression (e.g., recombinant expression) or synthesis (e.g., chemical synthesis) of the polypeptide.

As used herein, the terms "major histocompatibility complex" and "MHC" are used interchangeably and refer to an MHC class I molecule and/or an MHC class II molecule.

As used herein, the terms "human leukocyte antigen" and "HLA" are used interchangeably and refer to major histocompatibility complex (MHC) in humans. An HLA molecule may be a class I MHC molecule (e.g., HLA-A, HLA-B, HLA-C) or a class II MHC molecule (e.g., HLA-DP, HLA-DQ, HLA-DR).

As used herein, the term "major histocompatibility complex (MHC)-binding epitope" refers to a peptide that binds to or is predicted to bind to an MHC molecule.

As used herein, the terms "heat shock protein-binding peptide" and "HSP-binding peptide" are used interchangeably and refer to a peptide that non-covalently binds to an HSP. In certain embodiments, an HSP-binding peptide does not comprise an amino acid sequence containing more than 6, 7, 8, 9, 10, 11, 12, 13, 14, 15, 20, 25, 30, 35, 40, 45, or 50 contiguous amino acids of a protein (e.g., a naturally occurring protein) that comprises the amino acid sequence of SEQ ID NO: 1.

As used herein, the term "peptide linker" refers to a peptide bond or a peptide sequence that links a C-terminal amino acid residue of a first peptide to an N-terminal amino acid residue of a second peptide.

As used herein, the term "chemical linker" refers to any chemical bond or moiety that is capable of linking two molecules, wherein the bond or moiety is not a peptide linker.

As used herein, the terms "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal.

5.2 Heat Shock Protein (HSP)-Binding Peptides

In one aspect, the instant disclosure provides a polypeptide comprising an HSP-binding peptide comprising any one of the amino acid sequences provided in Table 1.

TABLE 1

Amino acid sequences of HSP-binding peptides

| Description | Amino Acid Sequence | SEQ ID NO |
|---|---|---|
| Consensus sequence 1 | $X_1LX_2LTX_3$, wherein: $X_1$ is W or F; $X_2$ is R or K; and $X_3$ is W, F, or G | 1 |
| Consensus sequence 2 | $NX_1LX_2LTX_3$, wherein: $X_1$ is W or F; $X_2$ is R or K; and $X_3$ is W, F, or G | 2 |
| Consensus sequence 3 | $WLX_1LTX_2$, wherein: $X_1$ is R or K; and $X_2$ is W or G | 3 |
| Consensus sequence 4 | $NWLX_1LTX_2$, wherein: $X_1$ is R or K; and $X_2$ is W or G | 4 |

TABLE 1-continued

Amino acid sequences of HSP-binding peptides

| Description | Amino Acid Sequence | SEQ ID NO |
|---|---|---|
| Consensus sequence 5 | $NWX_1X_2X_3X_4X_5$, wherein: $X_1$ is L or I; $X_2$ is L, R, or K; $X_3$ is L or I; $X_4$ is T, L, F, K, R, or W; and $X_5$ is W or K | 232 |
| PEP016 | WLRLTW | 5 |
| PEP017 | NWLRLTW | 6 |
| PEP018 | WLKLTW | 7 |
| PEP019 | NWLKLTW | 8 |
| PEP020 | WLRLTG | 9 |
| PEP021 | NWLRLTG | 10 |
| PEP022 | FLRLTF | 11 |
| PEP023 | NFLRLTF | 12 |
| PEP024 | WLRLTF | 98 |
| PEP025 | NWLRLTF | 99 |
| PEP040 | WLKLTF | 100 |
| PEP041 | NWLKLTF | 101 |
| PEP042 | WLKLTG | 102 |
| PEP043 | NWLKLTG | 103 |
| PEP044 | FLRLTW | 104 |
| PEP045 | NFLRLTW | 105 |
| PEP046 | FLRLTG | 106 |
| PEP047 | NFLRLTG | 107 |
| PEP048 | FLKLTW | 108 |
| PEP049 | NFLKLTW | 109 |
| PEP050 | FLKLTF | 110 |
| PEP051 | NFLKLTF | 111 |
| PEP103 | FLKLTG | 112 |
| PEP104 | NFLKLTG | 113 |
| PEP185 | NWLLLTW | 204 |
| PEP186 | NLLRWTG | 205 |
| PEP188 | FWLRLTW | 207 |
| PEP189 | NWLRLLW | 208 |
| PEP190 | NWLRLFW | 209 |
| PEP191 | NWLRLKW | 210 |
| PEP192 | NWIRITW | 211 |
| PEP193 | QWLRLTW | 212 |
| PEP194 | NWLKLKW | 213 |

TABLE 1-continued

Amino acid sequences of HSP-binding peptides

| Description | Amino Acid Sequence | SEQ ID NO |
|---|---|---|
| PEP195 | NWLKLRW | 214 |
| PEP196 | NWLKLWK | 215 |

In one aspect, the instant disclosure provides a polypeptide comprising an HSP-binding peptide comprising the amino acid sequence of $X_1LX_2LTX_3$ (SEQ ID NO: 1), wherein $X_1$ is W or F; $X_2$ is R or K; and $X_3$ is W, F, or G. In another aspect, the instant disclosure provides a polypeptide comprising an HSP-binding peptide comprising the amino acid sequence of $NWX_1X_2X_3X_4X_5$ (SEQ ID NO: 232), wherein $X_1$ is L or I; $X_2$ is L, R, or K; $X_3$ is L or I; $X_4$ is T, L, F, K, R, or W; and $X_5$ is W or K. In certain embodiments, the HSP-binding peptide binds to an HSP (e.g., Hsc70, Hsp70, Hsp90, Hsp110, Grp170, Gp96, or Calreticulin) with a $K_d$ lower than $10^{-3}$ M, $10^{-4}$ M, $10^{-5}$ M, $10^{-6}$ M, $10^{-7}$ M, $10^{-8}$ M, or $10^{-9}$ M. In certain embodiments, the HSP-binding peptide binds to Hsc70 (e.g., human Hsc70) with a $K_d$ of $10^{-3}$ M, $10^{-4}$ M, $10^{-5}$ M, $10^{-6}$ M, $10^{-7}$ M, $10^{-8}$ M, $10^{-9}$ M, or lower.

In certain embodiments, the HSP-binding peptide comprises the amino acid sequence of $NX_1LX_2LTX_3$ (SEQ ID NO: 2), wherein $X_1$ is W or F; $X_2$ is R or K; and $X_3$ is W, F, or G. In certain embodiments, the HSP-binding peptide comprises the amino acid sequence of $WLX_1LTX_2$ (SEQ ID NO: 3), wherein $X_1$ is R or K; and $X_2$ is W or G. In certain embodiments, the HSP-binding peptide comprises the amino acid sequence of $NWLX_1LTX_2$ (SEQ ID NO: 4), wherein $X_1$ is R or K; and $X_2$ is W or G.

In certain embodiments, the HSP-binding peptide comprises an amino acid sequence selected from the group consisting of SEQ ID NOs: 5-12, 98-113, 204-205, and 207-215. In certain embodiments, the HSP-binding peptide comprises the amino acid sequence of SEQ ID NO: 5. In certain embodiments, the HSP-binding peptide comprises the amino acid sequence of SEQ ID NO: 6. In certain embodiments, the HSP-binding peptide comprises the amino acid sequence of SEQ ID NO: 7. In certain embodiments, the HSP-binding peptide comprises the amino acid sequence of SEQ ID NO: 8. In certain embodiments, the HSP-binding peptide comprises the amino acid sequence of SEQ ID NO: 9. In certain embodiments, the HSP-binding peptide comprises the amino acid sequence of SEQ ID NO: 10. In certain embodiments, the HSP-binding peptide comprises the amino acid sequence of SEQ ID NO: 11. In certain embodiments, the HSP-binding peptide comprises the amino acid sequence of SEQ ID NO: 12. In certain embodiments, the HSP-binding peptide comprises the amino acid sequence of SEQ ID NO: 98. In certain embodiments, the HSP-binding peptide comprises the amino acid sequence of SEQ ID NO: 99. In certain embodiments, the HSP-binding peptide comprises the amino acid sequence of SEQ ID NO: 100. In certain embodiments, the HSP-binding peptide comprises the amino acid sequence of SEQ ID NO: 101. In certain embodiments, the HSP-binding peptide comprises the amino acid sequence of SEQ ID NO: 102. In certain embodiments, the HSP-binding peptide comprises the amino acid sequence of SEQ ID NO: 103. In certain embodiments, the HSP-binding peptide comprises the amino acid sequence of SEQ ID NO: 104. In certain embodiments, the HSP-binding peptide comprises the amino acid sequence of SEQ ID NO: 105. In certain embodiments, the HSP-binding peptide comprises the amino acid sequence of SEQ ID NO: 106. In certain embodiments, the HSP-binding peptide comprises the amino acid sequence of SEQ ID NO: 107. In certain embodiments, the HSP-binding peptide comprises the amino acid sequence of SEQ ID NO: 108. In certain embodiments, the HSP-binding peptide comprises the amino acid sequence of SEQ ID NO: 109. In certain embodiments, the HSP-binding peptide comprises the amino acid sequence of SEQ ID NO: 110. In certain embodiments, the HSP-binding peptide comprises the amino acid sequence of SEQ ID NO: 111. In certain embodiments, the HSP-binding peptide comprises the amino acid sequence of SEQ ID NO: 112. In certain embodiments, the HSP-binding peptide comprises the amino acid sequence of SEQ ID NO: 113. In certain embodiments, the HSP-binding peptide comprises the amino acid sequence of SEQ ID NO: 204. In certain embodiments, the HSP-binding peptide comprises the amino acid sequence of SEQ ID NO: 205. In certain embodiments, the HSP-binding peptide comprises the amino acid sequence of SEQ ID NO: 207. In certain embodiments, the HSP-binding peptide comprises the amino acid sequence of SEQ ID NO: 208. In certain embodiments, the HSP-binding peptide comprises the amino acid sequence of SEQ ID NO: 209. In certain embodiments, the HSP-binding peptide comprises the amino acid sequence of SEQ ID NO: 210. In certain embodiments, the HSP-binding peptide comprises the amino acid sequence of SEQ ID NO: 211. In certain embodiments, the HSP-binding peptide comprises the amino acid sequence of SEQ ID NO: 212. In certain embodiments, the HSP-binding peptide comprises the amino acid sequence of SEQ ID NO: 213. In certain embodiments, the HSP-binding peptide comprises the amino acid sequence of SEQ ID NO: 214. In certain embodiments, the HSP-binding peptide comprises the amino acid sequence of SEQ ID NO: 215.

In certain embodiments, the amino acid sequence of the HSP-binding peptide consists of the amino acid sequence of SEQ ID NO: 1. In certain embodiments, the amino acid sequence of the HSP-binding peptide consists of the amino acid sequence of SEQ ID NO: 2. In certain embodiments, the amino acid sequence of the HSP-binding peptide consists of the amino acid sequence of SEQ ID NO: 3. In certain embodiments, the amino acid sequence of the HSP-binding peptide consists of the amino acid sequence of SEQ ID NO: 4. In certain embodiments, the amino acid sequence of the HSP-binding peptide consists of the amino acid sequence of SEQ ID NO: 232.

In certain embodiments, the amino acid sequence of the HSP-binding peptide consists of an amino acid sequence selected from the group consisting of SEQ ID NOs: 5-12, 98-113, 204, 205, and 207-215. In certain embodiments, the amino acid sequence of the HSP-binding peptide consists of the amino acid sequence of SEQ ID NO: 5. In certain embodiments, the amino acid sequence of the HSP-binding peptide consists of the amino acid sequence of SEQ ID NO: 6. In certain embodiments, the amino acid sequence of the HSP-binding peptide consists of the amino acid sequence of SEQ ID NO: 7. In certain embodiments, the amino acid sequence of the HSP-binding peptide consists of the amino acid sequence of SEQ ID NO: 8. In certain embodiments, the amino acid sequence of the HSP-binding peptide consists of the amino acid sequence of SEQ ID NO: 9. In certain embodiments, the amino acid sequence of the HSP-binding peptide consists of the amino acid sequence of SEQ ID NO: 10. In certain embodiments, the amino acid sequence of the HSP-binding peptide consists of the amino acid sequence of SEQ ID NO: 11. In certain embodiments, the amino acid sequence of the HSP-binding peptide consists of the amino acid sequence of SEQ ID NO: 12. In certain embodiments, the amino acid sequence of the HSP-binding peptide consists of the amino acid sequence of SEQ ID NO: 98. In certain embodiments, the amino acid sequence of the HSP-binding peptide consists of the amino acid sequence of SEQ ID NO: 99. In certain embodiments, the amino acid sequence of the HSP-binding peptide consists of the amino acid sequence of SEQ ID NO: 100. In certain embodiments, the amino acid sequence of the HSP-binding peptide consists of the amino acid sequence of SEQ ID NO: 101. In certain embodiments, the amino acid sequence of the HSP-binding peptide consists of the amino acid sequence of SEQ ID NO: 102. In certain embodiments, the amino acid sequence of the HSP-binding peptide consists of the amino acid sequence of SEQ ID NO: 103. In certain embodiments, the amino acid sequence of the HSP-binding peptide consists of the amino acid sequence of SEQ ID NO: 104. In certain embodiments, the amino acid sequence of the HSP-binding peptide consists of the amino acid sequence of SEQ ID NO: 105. In certain embodiments, the amino acid sequence of the HSP-binding peptide consists of the amino acid sequence of SEQ ID NO: 106. In certain embodiments, the amino acid sequence of the HSP-binding peptide consists of the amino acid sequence of SEQ ID NO: 107. In certain embodiments, the amino acid sequence of the HSP-binding peptide consists of the amino acid sequence of SEQ ID NO: 108. In certain embodiments, the amino acid sequence of the HSP-binding peptide consists of the amino acid sequence of SEQ ID NO: 109. In certain embodiments, the amino acid sequence of the HSP-binding peptide consists of the amino acid sequence of SEQ ID NO: 110. In certain embodiments, the amino acid sequence of the HSP-binding peptide consists of the amino acid sequence of SEQ ID NO: 111. In certain embodiments, the amino acid sequence of the HSP-binding peptide consists of the amino acid sequence of SEQ ID NO: 112. In certain embodiments, the amino acid sequence of the HSP-binding peptide consists of the amino acid sequence of SEQ ID NO: 113. In certain embodiments, the amino acid sequence of the HSP-binding peptide consists of the amino acid sequence of SEQ ID NO: 204. In certain embodiments, the amino acid sequence of the HSP-binding peptide consists of the amino acid sequence of SEQ ID NO: 205. In certain embodiments, the amino acid sequence of the HSP-binding peptide consists of the amino acid sequence of SEQ ID NO: 207. In certain embodiments, the amino acid sequence of the HSP-binding peptide consists of the amino acid sequence of SEQ ID NO: 208. In certain embodiments, the amino acid sequence of the HSP-binding peptide consists of the amino acid sequence of SEQ ID NO: 209. In certain embodiments, the amino acid sequence of the HSP-binding peptide consists of the amino acid sequence of SEQ ID NO: 210. In certain embodiments, the amino acid sequence of the HSP-binding peptide consists of the amino acid sequence of SEQ ID NO: 211. In certain embodiments, the amino acid sequence of the HSP-binding peptide consists of the amino acid sequence of SEQ ID NO: 212. In certain embodiments, the amino acid sequence of the HSP-binding peptide consists of the amino acid sequence of SEQ ID NO: 213. In certain embodiments, the amino acid sequence of the HSP-binding peptide consists of the amino acid sequence of SEQ ID NO: 214. In certain embodiments, the amino acid sequence of the HSP-binding peptide consists of the amino acid sequence of SEQ ID NO: 215.

In certain embodiments, the HSP-binding peptide is no more than 100 (e.g., no more than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, or 95) amino acid residues in length. In certain embodiments, the HSP-binding peptide is from 6 to 50 (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) amino acid residues in length.

In certain embodiments, the amino acid sequence of the polypeptide consists of the amino acid sequence of the HSP-binding peptide.

In certain embodiments, the HSP-binding peptide further comprises a linker. The linker can be any chemical linker or peptide linker known in the art.

In certain embodiments, the linker comprises a moiety for chemical crosslinking or ultraviolet (UV) crosslinking. Any chemical crosslinking or UV crosslinking moieties known in the art (see, e.g., Wong, 1991, Chemistry of Protein Conjugation and Cross-Linking, CRC Press, incorporated herein by reference in its entirety) can be employed. In certain embodiments, the linker comprises a click chemistry handle. As used herein, the term "click chemistry handle" refers to a reactant or a reactive group that can partake in a click chemistry reaction. Exemplary click chemistry handles are demonstrated in U.S. Patent Publication 20130266512, which is incorporated by reference herein in its entirety.

In certain embodiments, the linker comprises a peptide linker. In certain embodiments, the peptide linker comprises an amino acid sequence that can be recognized and/or cleaved by a protease. In certain embodiments, the protease is expressed in a mammalian cell (e.g., a human cell). In certain embodiments, the protease is expressed in an antigen-presenting cell (e.g., B cell, macrophage, dendritic cell). In certain embodiments, the protease is a serine protease. In certain embodiments, the protease is trypsin, chymotrypsin, papain, V8 protease, or elastase. In certain embodiments, the peptide linker comprises or consists of the amino acid sequence of FFRK (SEQ ID NO: 13). In certain embodiments, the peptide linker comprises or consists of the amino acid sequence of FR.

TABLE 2

Amino acid sequences of linkers and HSP-binding peptides with linkers

| Description | Amino Acid Sequence | SEQ ID NO |
|---|---|---|
| Linker | FFRK | 13 |
| Linker | FR | N/A |
| Consensus sequence 1 with N-terminal linker | FFRKX$_1$LX$_2$LTX$_3$, wherein: X$_1$ is W or F; X$_2$ is R or K; and X$_3$ is W, F, or G | 14 |

TABLE 2-continued

Amino acid sequences of linkers and
HSP-binding peptides with linkers

| Description | Amino Acid Sequence | SEQ ID NO |
|---|---|---|
| Consensus sequence 2 with N-terminal linker | FFRKNX$_1$LX$_2$LTX$_3$, wherein: X$_1$ is W or F; X$_2$ is R or K; and X$_3$ is W, F, or G | 15 |
| Consensus sequence 3 with N-terminal linker | FFRKWLX$_1$LTX$_2$, wherein: X$_1$ is R or K; and X$_2$ is W or G | 16 |
| Consensus sequence 4 with N-terminal linker | FFRKNWLX$_1$LTX$_2$, wherein: X$_1$ is R or K; and X$_2$ is W or G | 17 |
| Consensus sequence 5 with N-terminal linker | FFRKNWX$_1$X$_2$X$_3$X$_4$X$_5$, wherein: X$_1$ is L or I; X$_2$ is L, R, or K; X$_3$ is L or I; X$_4$ is T, L, F, K, R, or W; and X$_5$ is W or K | 233 |
| PEP001 | FFRKNLLRLTG | 71 |
| PEP003 | FFRKNWLLLTW | 166 |
| PEP004 | FFRKNLLRWTG | 167 |
| PEP006 | FFRKNWLRLTW | 18 |
| PEP012 | FFRKNWLKLTW | 19 |
| PEP013 | FFRKNWIRITW | 173 |
| PEP014 | FFRKQWLRLTW | 174 |
| PEP026 | FFRKNWLRLTG | 20 |
| PEP027 | FFRKNFLRLTF | 21 |
| PEP028 | FRNWLRLTW | 22 |
| PEP029 | FRNWLKLTW | 23 |
| PEP030 | FRNWLRLTG | 24 |
| PEP031 | FRNFLRLTF | 25 |
| PEP055 | FFRKNWLKLKW | 72 |
| PEP057 | FFRKNWLKLRW | 74 |
| PEP058 | FFRKNWLKLWK | 75 |
| Consensus sequence 1 with C-terminal linker | X$_1$LX$_2$LTX$_3$FFRK, wherein: X$_1$ is W or F; X$_2$ is R or K; and X$_3$ is W, F, or G | 26 |
| Consensus sequence 2 with C-terminal linker | NX$_1$LX$_2$LTX$_3$FFRK, wherein: X$_1$ is W or F; X$_2$ is R or K; and X$_3$ is W, F, or G | 27 |
| Consensus sequence 3 with C-terminal linker | WLX$_1$LTX$_2$FFRK, wherein: X$_1$ is R or K; and X$_2$ is W or G | 28 |
| Consensus sequence 4 with C-terminal linker | NWLX$_1$LTX$_2$FFRK, wherein: X$_1$ is R or K; and X$_2$ is W or G | 29 |
| Consensus sequence 5 with C-terminal linker | NWX$_1$X$_2$X$_3$X$_4$X$_5$FFRK, wherein: X$_1$ is L or I; X$_2$ is L, R, or K; X$_3$ is L or I; | 234 |

TABLE 2-continued

Amino acid sequences of linkers and
HSP-binding peptides with linkers

| Description | Amino Acid Sequence | SEQ ID NO |
|---|---|---|
| | $X_4$ is T, L, F, K, R, or W; and $X_5$ is W or K | |
| PEP032 | NWLRLTWFFRK | 30 |
| PEP033 | NWLKLTWFFRK | 31 |
| PEP034 | NWLRLTGFFRK | 32 |
| PEP035 | NFLRLTFFFRK | 33 |
| PEP036 | NWLRLTWFR | 34 |
| PEP037 | NWLKLTWFR | 35 |
| PEP038 | NWLRLTGFR | 36 |
| PEP039 | NFLRLTFFR | 37 |
| PEP197 | NLLRLTWFFRK | 216 |
| PEP198 | NRLLLTGFFRK | 217 |
| PEP199 | NWLLLTWFFRK | 218 |
| PEP200 | NLLRWTGFFRK | 219 |
| PEP201 | NRLWLTGFFRK | 220 |
| PEP202 | FWLRLTWFFRK | 221 |
| PEP203 | NWLRLLWFFRK | 222 |
| PEP204 | NWLRLFWFFRK | 223 |
| PEP205 | NWLRLKWFFRK | 224 |
| PEP206 | NWIRITWFFRK | 225 |
| PEP207 | QWLRLTWFFRK | 226 |
| PEP208 | NWLKLKWFFRK | 227 |
| PEP209 | NWLKLRWFFRK | 228 |
| PEP210 | NWLKLWKFFRK | 229 |

In certain embodiments, the polypeptide comprises any one of the amino acid sequences provided in Table 2.

In certain embodiments, the linker is N-terminal to the HSP-binding peptide. In certain embodiments, the polypeptide comprises the amino acid sequence of SEQ ID NO: 14, 15, 16, 17, or 233. In certain embodiments, the polypeptide comprises the amino acid sequence of SEQ ID NO: 18, 19, 20, 21, 22, 23, 24, 25, 71, 72, 74, 75, 166, 167, 173, or 174. In certain embodiments, the amino acid sequence of the polypeptide consists of the amino acid sequence of SEQ ID NO: 14, 15, 16, 17, or 233. In certain embodiments, the amino acid sequence of the polypeptide consists of the amino acid sequence of SEQ ID NO: 18, 19, 20, 21, 22, 23, 24, 25, 71, 72, 74, 75, 166, 167, 173, or 174.

In certain embodiments, the linker is C-terminal to the HSP-binding peptide. In certain embodiments, the polypeptide comprises the amino acid sequence of SEQ ID NO: 26, 27, 28, 29, or 234. In certain embodiments, the polypeptide comprises the amino acid sequence of SEQ ID NO: 30, 31, 32, 33, 34, 35, 36, 37, 216, 217, 218, 219, 220, 221, 222, 223, 224, 225, 226, 227, 228, or 229. In certain embodiments, the amino acid sequence of the polypeptide consists of the amino acid sequence of SEQ ID NO: 26, 27, 28, 29, or 234. In certain embodiments, the amino acid sequence of the polypeptide consists of the amino acid sequence of SEQ ID NO: 30, 31, 32, 33, 34, 35, 36, 37, 216, 217, 218, 219, 220, 221, 222, 223, 224, 225, 226, 227, 228, or 229.

5.3 Polypeptides Comprising HSP-Binding Peptides

In one aspect, the instant disclosure provides a polypeptide comprising an HSP-binding peptide as disclosed herein and an antigenic peptide comprising one or more MHC-binding epitopes.

MHC-binding epitopes can be identified by methods known in the art, e.g., by an assay that measures the binding of a peptide to an MHC molecule (e.g., an HLA molecule). Non-limiting examples of such assays include inhibition of antigen presentation (Sette, et al., J. Immunol. 141:3893, 1991), in vitro assembly assays (Townsend, et al., Cell 62:285, 1990), and FACS based assays using mutated cells, such as RMA.S (Melief, et al., Eur. J. Immunol. 21:2963, 1991). In some instances, an MHC-binding epitope can be predicted to bind an MHC molecule (e.g., an HLA molecule)

by a software program (e.g. SYFPEITHI, Rammensee, et al., Immunogenetics 50, 213-219, 1999, incorporated herein by reference in its entirety). Other methods that can be used to identify an MHC-binding epitope include, without limitation, those disclosed in Guan, P. et al., (2003) Applied Bioinformatics, 2: 63-66; Blythe, M. J. et al., (2002) Bioinformatics, 18: 434-439; Flower, D. R. and Doytchinova, I. A. (2002). Applied Bioinformatics, 1: 167-176; Yu, K. et al., (2002) Molecular Medicine, 8: 137-48; Brusic, V. et al., (2002) Immunology and Cell Biology, 80: 280-285; Jung, G. et al., (2001) Biologicals, 29: 179-181 (which describes T cell epitope prediction programme EPIPREDICT); Kwok, W. W. et al., (2001) Trends in Immunology, 22: 583-588; Mallios, R. R. (2001) Bioinformatics, 17: 942-948; Romisch, K. (2001). Trends in Biochemical Sciences, 26: 531; Schirle, M. et al., (2001) Journal of Immunological Methods, 257: 1-16; Singh, H. and Raghava, G. P. S. (2001) Bioinformatics, 17: 1236-1237; Andersen, M. H. et al., (2000) Tissue Antigens, 55: 519-531; Buus, S. (1999). Current Opinion in Immunology, 11: 209-213; Mallios, R. R. (1999) Bioinformatics, 15: 432-439; Maffei, A. and Harris, P. E. (1998). Peptides, 19: 179-198; and Vita R. et al., (2015) Nucleic Acids Res., 43: D405-D412 (which describes the immune epitope database (IEDB) 3.0., available at www.iedb.org) (each of which is incorporated herein by reference in its entirety).

MHC molecules are classified as either Class I or Class II molecules. Class II MHC molecules are expressed primarily on cells involved in initiating and sustaining immune responses, such as dendritic cells, B lymphocytes, macrophages, etc. Class II MHC molecules are recognized by helper T lymphocytes and induce proliferation of helper T lymphocytes and amplification of the immune response to the particular immunogenic peptide that is displayed. Class I MHC molecules are expressed on almost all nucleated cells and are recognized by cytotoxic T lymphocytes (CTLs), which then destroy the antigen-bearing cells. Cytotoxic T lymphocytes are particularly important in tumor rejection and in fighting viral infections. The CTL recognizes the antigen in the form of a peptide fragment bound to the MHC class I molecules rather than the intact foreign antigen itself. The capacity of peptides to bind MHC molecules can be measured in a variety of different ways, such as by inhibition of antigen presentation (Sette, et al., J. Immunol. 141:3893, 1991, incorporated herein by reference in its entirety), in vitro assembly assays (Townsend, et al., Cell 62:285, 1990), and FACS based assays using mutated cells, such as RMA.S (Melief, et al., Eur. J. Immunol. 21:2963, 1991, incorporated herein by reference in its entirety). MHC-binding epitopes predicted to bind MHC class I molecules are typically between 8 to 11 residues, while MHC-binding epitopes predicted to bind MHC class II molecules are typically in the range of 10 to 20 residues.

In certain embodiments, the MHC-binding epitope is an HLA-binding epitope. In certain embodiments, the MHC-binding epitope binds to an MHC I molecule with an IC50 smaller than or equal to 500 nM (e.g., smaller than or equal to 1, 2, 3, 4, 5, 6, 7, 8, 9, 10, 20, 30, 40, 50, 60, 70, 80, 90, 100, 150, 200, 250, 300, 350, 400, or 450 nM). In certain embodiments, the MHC-binding epitope binds to an MHC II molecule with an IC50 smaller than or equal to 1000 nM (e.g., smaller than or equal to 1, 2, 3, 4, 5, 6, 7, 8, 9, 10, 20, 30, 40, 50, 60, 70, 80, 90, 100, 150, 200, 250, 300, 350, 400, 450, 500, 600, 700, 800, or 900 nM).

In certain embodiments, the sequence of the MHC-binding epitope is identified from one or more of a subject's cancer cells (e.g., cells of cervical cancer, adenocarcinoma, glioblastoma, or multiple myeloma). In certain embodiments, the amino acid sequence of the MHC-binding epitope is 100% identical to the sequence identified from the cancer cell(s). In certain embodiments, the amino acid sequence of the MHC-binding epitope is at least 70%, 80%, 90%, or 95% identical to the sequence identified from the cancer cell, optionally wherein the difference comprises mostly or only conservative substitutions of amino acids. The amino acid sequence identified from the cancer cell can be either wild-type or mutant relative to the most frequent sequence of the population of the species. Where the amino acid sequence identified from the cancer cell is mutant, it can comprise an amino acid mutation (e.g., a substitution, deletion, or insertion mutation) or a gene fusion mutation (e.g., as a result of genomic translocation or transposition).

In certain embodiments, the sequence of the MHC-binding epitope is identified from a pathogenic microbe. The pathogenic microbe can be a virus, a bacterium, a fungus, a protozoan, or a parasite. Exemplary viruses include hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus (e.g., human papillomavirus (HPV)), papova virus, cytomegalovirus, echinovirus, arbovirus, hantavirus, coxsackie virus, mumps virus, measles virus, rubella virus, polio virus, Epstein Barr virus (EBV), human immunodeficiency virus type I (HIV-I), human immunodeficiency virus type II (HIV-II), dengue virus, smallpox virus, and Zika virus. Exemplary bacteria include *Escherichia coli, Klebsiella pneumoniae, Staphylococcus aureus, Enterococcus faecalis, Proteus vulgaris, Staphylococcus viridans*, and *Pseudomonas aeruginosa*. Exemplary fungi include *Candida* (e.g., *Candida glabrata*), *Pneumocystis carinii, Fusarium* keratitis, coccidioidal, *Aspergillus niger, Cryptococcus neoformans*, and *Curvularia geniculata*. Exemplary protozoa include *leishmania*, coccidiosis, *trypanosoma schistosoma*, and malaria. Exemplary parasites include *chlamydia* and *rickettsia*.

In certain embodiments, the MHC-binding epitope comprises a modified amino acid residue. In certain embodiments, the MHC-binding epitope comprises a phosphorylated residue (e.g., a Tyr, Ser, Thr, Arg, Lys, or His that has been phosphorylated on a side chain hydroxyl or amine). In certain embodiments, the MHC-binding epitope comprises a phosphomimetic residue (e.g., a mimetic of a Tyr, Ser, Thr, Arg, Lys, or His amino acid that has been phosphorylated on a side chain hydroxyl or amine). Non-limiting examples of phosphomimetic groups include O-boranophospho, borono, O-dithiophospho, phosphoramide, H-phosphonate, alkylphosphonate, phosphorothiolate, phosphodithiolate and phosphorofluoridate, any of which may be derivatized on Tyr, Thr, Ser, Arg, Lys, or His residues. In certain embodiments, an Asp or Glu residue is used as a phosphomimetic in place of a phospho-Tyr, phospho-Thr, phospho-Ser, phospho-Arg, phospho-Lys and/or phospho-His residue in a peptide. In certain embodiments, the phosphomimetic residue is a non-hydrolyzable analogue of a phosphorylated residue.

The antigenic peptide can comprise one or more MHC-binding epitopes. In certain embodiments, the antigenic peptide comprises one MHC-binding epitope. In certain embodiments, the antigenic peptide comprises two or more (e.g., 3, 4, 5, 6, 7, 8, 9, 10, or more) MHC-binding epitopes. The two or more MHC-binding epitopes can be linked via a chemical linker or a peptide linker, wherein the peptide linker optionally comprises an amino acid sequence that can be recognized and/or cleaved by a protease.

In certain embodiments, the antigenic peptide is 8 to 50 amino acids (e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids) in length. In certain embodiments, the antigenic peptide is 12 to 50, 20 to 40, 20 to 35, 25 to 40, 20 to 30, 25 to 35, or 30 to 40 amino acids in length.

The HSP-binding peptide can be linked to the antigenic peptide via a chemical linker or a peptide linker. In certain embodiments, the HSP-binding peptide can be linked to the antigenic peptide via a chemical linker. Any chemical linkers can be employed to link the HSP-binding peptide and the antigenic peptide. Exemplary chemical linkers include moieties generated from chemical crosslinking (see, e.g., Wong, 1991, Chemistry of Protein Conjugation and Cross-Linking, CRC Press, incorporated herein by reference in its entirety), UV crosslinking, and click chemistry reactions (see, e.g., U.S. Patent Publication 20130266512, which is incorporated by reference herein in its entirety). In certain embodiments, the HSP-binding peptide can be linked to the antigenic peptide via a peptide linker (e.g., a peptide linker as disclosed in Section 5.2).

The HSP-binding sequence can be linked to the antigenic peptide at any amino acid position. In certain embodiments, the C-terminus of the HSP-binding sequence is linked to the N-terminus of the antigenic peptide via a chemical linker. In certain embodiments, the N-terminus of the HSP-binding sequence is linked to the C-terminus of the antigenic peptide via a chemical linker. In certain embodiments, the C-terminus of the HSP-binding sequence is linked to the N-terminus of the antigenic peptide via a peptide linker. In certain embodiments, the N-terminus of the HSP-binding sequence is linked to the C-terminus of the antigenic peptide via a peptide linker. In certain embodiments, the HSP-binding peptide is at the C-terminus of the polypeptide. Polypeptides having an HSP-binding peptide at the C-terminus are generally advantageous in having an improved purity when produced by solid-phase synthesis. In certain embodiments, the HSP-binding peptide is at the N-terminus of the polypeptide. In certain embodiments, the heat shock protein-binding peptide is not at the N-terminus or the C-terminus of the polypeptide. In certain embodiments, the heat shock protein-binding peptide is at the center of the polypeptide.

In certain embodiments, the polypeptide comprises, from N-terminus to C-terminus, an antigenic peptide comprising one or more MHC-binding epitopes, a peptide linker, and an HSP-binding peptide disclosed herein. In certain embodiments, the polypeptide comprises the amino acid sequence of SEQ ID NO: 14, 15, 16, 17, or 233. In certain embodiments, the polypeptide comprises the amino acid sequence of SEQ ID NO: 18, 19, 20, 21, 22, 23, 24, 25, 71, 72, 74, 75, 166, 167, 173, or 174. In certain embodiments, the amino acid sequence of the polypeptide consists of, from N-terminus to C-terminus, the amino acid sequence of an antigenic peptide disclosed herein, and the amino acid sequence of SEQ ID NO: 14, 15, 16, 17, or 233. In certain embodiments, the amino acid sequence of the polypeptide consists of, from N-terminus to C-terminus, the amino acid sequence of an antigenic peptide disclosed herein, and the amino acid sequence of SEQ ID NO: 18, 19, 20, 21, 22, 23, 24, 25, 71, 72, 74, 75, 166, 167, 173, or 174.

In certain embodiments, the polypeptide comprises, from N-terminus to C-terminus, an HSP-binding peptide disclosed herein, a peptide linker, and an antigenic peptide comprising one or more MHC-binding epitopes. In certain embodiments, the polypeptide comprises the amino acid sequence of SEQ ID NO: 26, 27, 28, 29, or 234. In certain embodiments, the polypeptide comprises the amino acid sequence of SEQ ID NO: 30, 31, 32, 33, 34, 35, 36, 37, or 216, 217, 218, 219, 220, 221, 222, 223, 224, 225, 226, 227, 228, or 229. In certain embodiments, the amino acid sequence of the polypeptide consists of, from N-terminus to C-terminus, the amino acid sequence of SEQ ID NO: 26, 27, 28, 29, or 234, and the amino acid sequence of an antigenic peptide disclosed herein. In certain embodiments, the amino acid sequence of the polypeptide consists of, from N-terminus to C-terminus, the amino acid sequence of SEQ ID NO: 30, 31, 32, 33, 34, 35, 36, 37, 216, 217, 218, 219, 220, 221, 222, 223, 224, 225, 226, 227, 228, or 229, and the amino acid sequence of an antigenic peptide disclosed herein.

In certain embodiments, the polypeptide disclosed herein is no more than 500 amino acids (e.g., no more than 400, 300, 200, 100, 90, 80, 70, 60, 50, or 40 amino acids) in length. In certain embodiments, the amino acid sequence of the polypeptide is not naturally occurring.

In certain embodiments, the polypeptide binds to an HSP (e.g., Hsc70, Hsp70, Hsp90, Hsp110, Grp170, Gp96, or Calreticulin) with a $K_d$ lower than $10^{-3}$ M, $10^{-4}$ M, $10^{-5}$ M, $10^{-6}$ M, $10^{-7}$ M, $10^{-8}$ M, or $10^{-9}$ M. In certain embodiments, the polypeptide binds to Hsc70 (e.g., human Hsc70) with a $K_d$ of $10^{-3}$ M, $10^{-4}$ M, $10^{-5}$ M, $10^{-6}$ M, $10^{-7}$ M, $10^{-8}$ M, $10^{-9}$ M, or lower.

5.3.1 Production of Polypeptides by Chemical Synthesis

Polypeptides disclosed herein can be synthesized by standard chemical methods including the use of a peptide synthesizer. Conventional peptide synthesis or other synthetic protocols well known in the art can be used.

In certain embodiments, the polypeptide disclosed herein consists of amino acid residues linked by peptide bonds. Such polypeptides can be synthesized, for example, by solid-phase peptide synthesis using procedures similar to those described by Merrifield, 1963, J. Am. Chem. Soc., 85:2149, incorporated herein by reference in its entirety. During synthesis, N-α-protected amino acids having protected side chains are added stepwise to a growing polypeptide chain linked by its C-terminal and to an insoluble polymeric support i.e., polystyrene beads. The polypeptides are synthesized by linking an amino group of an N-α-deprotected amino acid to an α-carboxyl group of an N-α-protected amino acid that has been activated by reacting it with a reagent such as dicyclohexylcarbodiimide or 2-(6-Chloro-1-H-benzotriazole-1-yl)-1,1,3,3-tetramethylaminium hexafluorophosphate. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag, each of which is incorporated herein by reference in its entirety).

In addition, analogs and derivatives of polypeptides can be chemically synthesized as described supra. If desired, nonclassical amino acids or chemical amino acid analogs can be introduced as a substitution or addition into the peptide sequence. Non-classical amino acids include, but are not limited to, the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, C-α-methyl amino acids, and N-α-methyl amino acids.

Polypeptides phosphorylated on the side chains of Tyr, Ser, Thr, Arg, Lys, and His can be synthesized in Fmoc solid phase synthesis using the appropriate side chain protected Fmoc-phospho amino acid. In this way, polypeptides with a combination of phosphorylated and non-phosphorylated Tyr, Ser, Thr, Arg, Lys, and His residues can be synthesized. For example, the method of Staerkaer et al can be applied (1991, Tetrahedron Letters 32: 5389-5392). Other procedures (some for specific amino acids) are detailed in De Bont et al. (1987, Tray. Chim Pays Bas 106: 641, 642), Bannwarth and Trezeciak (1987, Helv. Chim. Acta 70: 175-186), Perich and Johns (1988, Tetrahedron Letters 29: 2369-2372), Kitas et al. (1990, J. Org. Chem. 55:4181-4187), Valerio et al. (1989, Int. J. Peptide Protein Res. 33:428-438), Perich et al. (1991, Tetrahedron Letters 32:4033-4034), Pennington (1994, Meth. Molec. Biol. 35:195-2), and Perich (1997, Methods Enzymol. 289:245-266, each of which is incorporated herein by reference in its entirety).

A phosphorylated polypeptide can also be produced by first culturing a cell transformed with a nucleic acid that encodes the amino acid sequence of the polypeptide. After producing such a polypeptide by cell culture, the hydroxyl groups of the appropriate amino acid are substituted by phosphate groups using organic synthesis or enzymatic methods with phosphorylation enzymes. For example, in the case of serine-specific phosphorylation, serine kinases can be used.

Phosphopeptide mimetics can also be synthesized, wherein a phosphorylated amino acid residue in a polypeptide is replaced with a phosphomimetic group. Non-limiting examples of phosphomimetic groups include O-boranophospho, borono, O-dithiophospho, phosphoramide, H-phosphonate, alkylphosphonate, phosphorothiolate, phosphodithiolate and phosphorofluoridate, any of which may be derivatized on Tyr, Thr, Ser, Arg, Lys, or His residues. In certain embodiments, an Asp or Glu residue is used as a phosphomimetic. Asp or Glu residues can also function as phosphomimetic groups, and be used in place of a phospho-Tyr, phospho-Thr, phospho-Ser, phospho-Arg, phospho-Lys and/or phospho-His residue in a peptide.

Purification of the resulting peptide is accomplished using conventional procedures, such as preparative HPLC using reverse-phase, gel permeation, partition and/or ion exchange chromatography. The choice of appropriate matrices and buffers are well known in the art and so are not described in detail herein.

5.3.2 Production of Polypeptides Using Recombinant DNA Technology

Polypeptides disclosed herein can also be prepared by recombinant DNA methods known in the art. A nucleic acid sequence encoding a polypeptide can be obtained by back translation of the amino acid sequence and synthesized by standard chemical methods, such as the use of an oligonucleotide synthesizer. Alternatively, coding information for polypeptides can be obtained from DNA templates using specifically designed oligonucleotide primers and PCR methodologies. Variations and fragments of the polypeptides can be made by substitutions, insertions or deletions that provide for functionally equivalent molecules. Due to the degeneracy of nucleotide coding sequences, DNA sequences which encode the same or a variant of a polypeptide may be used in the practice of the present invention. These include, but are not limited to, nucleotide sequences which are altered by the substitution of different codons that encode a functionally equivalent amino acid residue within the sequence, thus producing a silent or conservative change. The nucleic acid encoding a polypeptide can be inserted into an expression vector for propagation and expression in host cells.

As the coding sequence for peptides of the length contemplated herein can be synthesized by chemical techniques, for example, the phosphotriester method of Matteucci et al., J. Am. Chem. Soc. 103:3185 (1981) (incorporated herein by reference in its entirety), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired peptide or fusion protein. A number of such vectors and suitable host systems are now available. For expression of the peptide or fusion proteins, the coding sequence will be provided with operably linked start and stop codons, promoter and terminator regions and usually a replication system to provide an expression vector for expression in the desired cellular host.

An expression construct refers to a nucleotide sequence encoding a polypeptide operably linked with one or more regulatory regions which enables expression of the peptide in an appropriate host cell. "Operably-linked" refers to an association in which the regulatory regions and the peptide sequence to be expressed are joined and positioned in such a way as to permit transcription, and ultimately, translation.

The regulatory regions necessary for transcription of the peptide can be provided by the expression vector. A translation initiation codon (ATG) may also be provided if the peptide gene sequence lacking its cognate initiation codon is to be expressed. In a compatible host-construct system, cellular transcriptional factors, such as RNA polymerase, will bind to the regulatory regions on the expression construct to effect transcription of the peptide sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to the peptide gene sequence or to insert the peptide gene sequence into the cloning site of a vector, linkers or adapters providing the appropriate compatible restriction sites may be ligated to the ends of the cDNAs by techniques well known in the art (Wu et al., 1987, Methods in Enzymol 152:343-349, incorporated herein by reference in its entirety). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising a polypeptide coding sequence operably linked with regulatory regions can be directly introduced into appropriate host cells for expression and production of the peptide without further cloning. The expression constructs can also contain DNA sequences that facilitate integration of the DNA sequence into the genome of the host cell, e.g., via homologous recombination. In this instance, it is not necessary to use an expression vector comprising a replication origin suitable for appropriate host cells in order to propagate and express the peptide in the host cells.

A variety of expression vectors may be used including plasmids, cosmids, phage, phagemids or modified viruses. Typically, such expression vectors comprise a functional origin of replication for propagation of the vector in an appropriate host cell, one or more restriction endonuclease sites for insertion of the peptide gene sequence, and one or more selection markers. Expression vectors may be constructed to carry nucleotide sequences for one or more of the polypeptides disclosed herein. The expression vector must be used with a compatible host cell which may be derived from a prokaryotic or eukaryotic organism including but not limited to bacteria, yeasts, insects, mammals and humans. Such host cells can be transformed to express one or more polypeptides disclosed herein, such as by transformation of the host cell with a single expression vector containing a plurality of nucleotide sequences encoding any of the polypeptides disclosed herein, or by transformation of the host cell with multiple expression vectors encoding different polypeptides disclosed herein.

In bacterial systems, a number of expression vectors may be advantageously selected to produce polypeptides. For example, when a large quantity of such a protein is to be produced, such as for the generation of pharmaceutical compositions, vectors that direct the expression of high levels of fusion protein products that are readily purified may be desirable. Such vectors include the E. coli expression vector pUR278 (Ruther et al., 1983, EMBO J. 2, 1791, incorporated herein by reference in its entirety), in which the peptide coding sequence may be ligated individually into the vector in frame with the lac Z coding region so that a fusion protein is produced; pIN vectors (Inouye and Inouye, 1985, Nucleic Acids Res. 13, 3101-3109; Van Heeke and Schuster, 1989, J. Biol. Chem 264, 5503-5509, each of which is incorporated herein by reference in its entirety); and the like. pGEX vectors may also be used to express these peptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the polypeptide can be released from the GST moiety.

Alternatively, for long term, high yield production of properly processed peptide complexes, stable expression in mammalian cells is preferred. Cell lines that stably express peptide complexes may be engineered by using a vector that contains a selectable marker. By way of example, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while the peptide is expressed continuously.

The recombinant cells may be cultured under standard conditions of temperature, incubation time, optical density and media composition. However, conditions for growth of recombinant cells may be different from those for expression of the polypeptides. Modified culture conditions and media may also be used to enhance production of the peptides. For example, recombinant cells containing peptides with their cognate promoters may be exposed to heat or other environmental stress, or chemical stress. Any techniques known in the art may be applied to establish the optimal conditions for producing peptide complexes.

In one embodiment of the invention, a codon encoding methionine is added at the 5' end of the nucleotide sequence encoding a polypeptide to provide a signal for initiation of translation of the peptide. This methionine may remain attached to the polypeptide, or the methionine may be removed by the addition of an enzyme or enzymes that can catalyze the cleavage of methionine from the peptide. For example, in both prokaryotes and eukaryotes, N-terminal methionine is removed by a methionine aminopeptidase (MAP) (Tsunasawa et al., 1985, J. Biol. Chem. 260, 5382-5391, incorporated herein by reference in its entirety). Methionine aminopeptidases have been isolated and cloned from several organisms, including E. coli, yeast, and rat.

The peptide may be recovered from the bacterial, mammalian, or other host cell types, or from the culture medium, by known methods (see, for example, Current Protocols in Immunology, vol. 2, chapter 8, Coligan et al. (ed.), John Wiley & Sons, Inc.; Pathogenic and Clinical Microbiology: A Laboratory Manual by Rowland et al., Little Brown & Co., June 1994, incorporated herein by reference in its entirety).

Both of the foregoing methods can be used for synthesizing a polypeptide disclosed herein. For example, a peptide comprising the amino acid sequence of the HSP-binding peptide can be synthesized chemically, and joined to an antigenic peptide, optionally produced by recombinant DNA technology, via a peptide bond.

Included within the scope of the invention are derivatives or analogs of the polypeptides disclosed herein that are modified during or after translation, e.g., by glycosylation, acetylation, phosphorylation, amidation (e.g., of the C-terminal carboxyl group), or derivatization by known protecting/blocking groups, or proteolytic cleavage. Any of numerous chemical modifications may be carried out by known techniques, including but not limited to, reagents useful for protection or modification of free $NH_2$— groups, free COOH— groups, OH— groups, side groups of Trp-, Tyr-, Phe-, His-, Arg-, or Lys-; specific chemical cleavage by cyanogen bromide, hydroxylamine, BNPS-Skatole, acid, or alkali hydrolysis; enzymatic cleavage by trypsin, chymotrypsin, papain, V8 protease, $NaBH_4$; acetylation, formylation, oxidation, reduction; metabolic synthesis in the presence of tunicamycin; etc.

5.4 Pharmaceutical Compositions

In another aspect, the instant disclosure provides a composition (e.g., a pharmaceutical composition) comprising one or more polypeptide as disclosed herein. In certain embodiments, the instant disclosure provides a composition (e.g., a pharmaceutical composition) comprising one or more (e.g., two or more, three or more, four or more, five or more, ten or more, or 20 or more) different polypeptides as disclosed herein. In certain embodiments, the instant disclosure provides a composition (e.g., a pharmaceutical composition) comprising no more than 30 different polypeptides as disclosed herein. In certain embodiments, the instant disclosure provides a composition (e.g., a pharmaceutical composition) comprising 1 to 30 (e.g., 2 to 20, 3 to 20, 4 to 20, 5 to 20, 5 to 15, or 5 to 10) different polypeptides as disclosed herein. In certain embodiments, the different polypeptides each comprise the same HSP-binding peptide and a different antigenic peptide.

In certain embodiments, the composition further comprises a purified stress protein. Such composition is useful as a vaccine formulation. Also provided is a method for making a vaccine, the method comprising mixing one or more compositions disclosed herein with a purified stress protein such that the purified stress protein binds to at least one of the HSP-binding antigenic conjugates or peptides.

5.4.1 Polypeptides in Complex with Stress Proteins

In a particular aspect, the instant disclosure provides a composition (e.g., a pharmaceutical composition) comprising one or more polypeptides as disclosed herein and a purified stress protein. In certain embodiments, at least a portion of the purified stress protein binds to the polypeptide in the composition. Such compositions are useful as vaccine formulations for the treatment of a cancer or an infection of a pathogenic microbe.

In certain embodiments, prior to complexation with purified stress proteins, the polypeptides may be reconstituted from powder in 100% DMSO. Equimolar amounts of the peptides may then be pooled in a solution of 75% DMSO diluted in sterile water.

In certain embodiments, prior to complexation with purified stress proteins, the polypeptides may be reconstituted in neutral water.

In certain embodiments, prior to complexation with purified stress proteins, the polypeptides may be reconstituted in acidic water containing HCl.

In certain embodiments, prior to complexation with purified stress proteins, the polypeptides may be reconstituted in basic water containing NaOH.

In certain embodiments, prior to complexation with purified stress proteins, the solubility of each polypeptide in water may be tested. If a polypeptide is soluble in neutral water, neutral water may be used as a solvent for the polypeptide. If the polypeptide is not soluble in neutral water, solubility in acidic water containing HCl, or another acid, e.g., acetic acid, phosphoric acid, or sulfuric acid may be tested. If the polypeptide is soluble in acidic water containing HCl (or another acid), acidic water containing HCl (or another acid) may be used as the solvent for the polypeptide. If the polypeptide is not soluble in acidic water containing HCl (or another acid), solubility in basic water containing NaOH may be tested. If the polypeptide is soluble in basic water containing NaOH, basic water containing NaOH may be used as the solvent for the polypeptide. If the polypeptide is not soluble in basic water containing NaOH, the polypeptide may be dissolved in DMSO. If the polypeptide is not soluble in DMSO the polypeptide may be excluded from the vaccine. The dissolved polypeptides may then be mixed to make a pool of polypeptides. The dissolved polypeptides may be mixed at equal volume. The dissolved polypeptides may be mixed in equimolar amounts.

Stress proteins, which are also referred to interchangeably herein as heat shock proteins (HSPs), useful in the practice of the instant invention can be selected from among any cellular protein that is capable of binding other proteins or peptides and capable of releasing the bound proteins or peptides in the presence of adenosine triphosphate (ATP) or under acidic conditions. The intracellular concentration of such protein may increase when a cell is exposed to a stressful stimulus. In addition to those heat shock proteins that are induced by stress, the HSP60, HSP70, HSP90, HSP100, sHSPs, and PDI families also include proteins that are related to stress-induced HSPs in sequence similarity, for example, having greater than 35% amino acid identity, but whose expression levels are not altered by stress. Therefore, stress protein or heat shock protein embraces other proteins, mutants, analogs, and variants thereof having at least 35% (e.g., at least 40, 45, 50, 55, 60, 65, 70, 75, 80, 85, 90, 95, or 99%) amino acid identity with members of these families whose expression levels in a cell are enhanced in response to a stressful stimulus. Accordingly, in certain embodiments, the stress protein is a member of the hsp60, hsp70, or hsp90 family of stress proteins (e.g., Hsc70, human Hsc70), or a mutant, analog, or variant thereof. In certain embodiments, the stress protein is selected from the group consisting of hsc70, hsp70, hsp90, hsp110, grp170, gp96, calreticulin, a mutant thereof, and combinations of two or more thereof. In certain embodiments, the stress protein is Hsc70 (e.g., human Hsc70). In certain embodiments, the stress protein is Hsp70 (e.g., human Hsp70). In certain embodiments, the stress protein (e.g., human hsc70) is a recombinant protein.

Amino acid sequences and nucleotide sequences of naturally occurring HSPs are generally available in sequence databases, such as GenBank. For example, Homo sapiens heat shock protein HSP70 (Heat Shock 70 kDa Protein 1A) has the following identifiers HGNC: 5232; Entrez Gene: 3303; Ensembl: ENSG00000204389; OMIM: 140550; UniProtKB: P08107 and NCBI Reference Sequence: NM_005345.5. Computer programs, such as Entrez, can be used to browse the database, and retrieve any amino acid sequence and genetic sequence data of interest by accession number. These databases can also be searched to identify sequences with various degrees of similarities to a query sequence using programs, such as FASTA and BLAST, which rank the similar sequences by alignment scores and statistics. Nucleotide sequences of non-limiting examples of HSPs that can be used for preparation of the HSP peptide-binding fragments of the invention are as follows: human Hsp70, Genbank Accession No. NM_005345, Sargent et al., 1989, Proc. Natl. Acad. Sci. U.S.A., 86:1968-1972; human Hsc70: Genbank Accession Nos. P11142, Y00371; human Hsp90, Genbank Accession No. X15183, Yamazaki et al., Nucl. Acids Res. 17:7108; human gp96: Genbank Accession No. X15187, Maki et al., 1990, Proc. Natl. Acad Sci., 87: 5658-5562; human BiP: Genbank Accession No. M19645; Ting et al., 1988, DNA 7: 275-286; human Hsp27, Genbank Accession No. M24743; Hickey et al., 1986, Nucleic Acids Res. 14:4127-45; mouse Hsp70: Genbank Accession No. M35021, Hunt et al., 1990, Gene, 87:199-204; mouse gp96: Genbank Accession No. M16370, Srivastava et al., 1987, Proc. Natl. Acad. Sci., 85:3807-3811; and mouse BiP: Genbank Accession No. U16277, Haas et al., 1988, Proc. Natl. Acad. Sci. U.S.A., 85: 2250-2254 (each of these references is incorporated herein by reference in its entirety).

In addition to the major stress protein families described above, an endoplasmic reticulum resident protein, calreticulin, has also been identified as yet another heat shock protein useful for eliciting an immune response when complexed to antigenic molecules (Basu and Srivastava, 1999, J. Exp. Med. 189:797-202; incorporated herein by reference in its entirety). Other stress proteins that can be used in the invention include grp78 (or BiP), protein disulfide isomerase (PDI), hsp110, and grp170 (Lin et al., 1993, Mol. Biol. Cell, 4:1109-1119; Wang et al., 2001, J. Immunol., 165:490-497, each of which is incorporated herein by reference in its entirety). Many members of these families were found subsequently to be induced in response to other stressful stimuli including nutrient deprivation, metabolic disruption, oxygen radicals, hypoxia and infection with intracellular pathogens (see Welch, May 1993, Scientific American 56-64; Young, 1990, Annu. Rev. Immunol. 8:401-420; Craig, 1993, Science 260:1902-1903; Gething, et al., 1992, Nature 355:33-45; and Lindquist, et al., 1988, Annu. Rev. Genetics 22:631-677, each of which is incorporated herein by reference in its entirety). It is contemplated that HSPs/stress proteins belonging to all of these families can be used in the practice of the invention. In certain embodiments, a stress protein encompasses any chaperone protein that facilitates peptide-MHC presentation. Suitable chaperone proteins include, but are not limited to, ER chaperones and tapasin (e.g., human tapasin).

The major stress proteins can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch, et al., 1985, J. Cell. Biol. 101:1198-1211, incorporated herein by reference in its entirety). In contrast, hsp90 and hsp60 proteins are abundant at normal temperatures in most, but not all, mammalian cells and are further induced by heat (Lai, et al., 1984, Mol. Cell. Biol. 4:2802-10; van Bergen en Henegouwen, et al., 1987, Genes Dev. 1:525-31, each of which is incorporated herein by reference in its entirety).

In various embodiments, nucleotide sequences encoding heat shock protein within a family or variants of a heat shock protein can be identified and obtained by hybridization with a probe comprising nucleotide sequence encoding an HSP under conditions of low to medium stringency. By way of example, procedures using such conditions of low stringency are as follows (see also Shilo and Weinberg, 1981, Proc. Natl. Acad. Sci. USA 78:6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for signal detection. If necessary, filters are washed for a third time at 65-68° C. before signal detection. Other conditions of low stringency which may be used are well known in the art (e.g., as used for cross-species hybridizations).

Where stress proteins are used, peptide-binding fragments of stress proteins and functionally active derivatives, analogs, and variants thereof can also be used. Accordingly, in certain embodiments, the stress protein is a full-length HSP. In certain embodiments, the stress protein is a polypeptide comprising a domain of an HSP (e.g., a member of the Hsp60, Hsp70, or Hsp90 family, such as Hsc70, particularly human Hsc70), wherein the domain is capable of being noncovalently associated with a peptide (e.g., an HSP-binding peptide as described herein) to form a complex and optionally eliciting an immune response, and wherein the stress protein is not a full-length HSP.

In certain embodiments, the stress protein is a polypeptide that is capable of being noncovalently associated with a peptide (e.g., an HSP-binding peptide as described herein) to form a complex and optionally eliciting an immune response, wherein the stress protein shares a high degree of sequence similarity with a wild-type HSP (e.g., a member of the Hsp60, Hsp70, or Hsp90 family, such as Hsc70, particularly human Hsc70). To determine a region of identity between two amino acid sequences or nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions× 100%). In one embodiment, the two sequences are the same length.

The determination of percent identity between two sequences can also be accomplished using a mathematical algorithm. A non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877 (each of which is incorporated herein by reference in its entirety). Such an algorithm is incorporated into the NBLAST and XBLAST programs of Altschul, et al., 1990, J. Mol. Biol. 215:403-410 (incorporated herein by reference in its entirety). BLAST nucleotide searches can be performed with the NBLAST program, e.g., score=100, wordlength=12 to obtain nucleotide sequences homologous to a nucleic acid molecules of the invention. BLAST protein searches can be performed with the XBLAST program, e.g., score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used. Another example of a mathematical algorithm utilized for the comparison of sequences is the algorithm of Myers and Miller, 1988, CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In certain embodiments, isolated peptide-binding domains of a stress protein (e.g., Hsp70 and Hsc70) are employed. These peptide-binding domains can be identified by computer modeling of the three dimensional structure of the peptide-binding site of a stress protein (e.g., Hsp70 and Hsc70). See for example, the peptide-binding fragments of HSPs disclosed in United States patent publication US 2001/0034042 (incorporated herein by reference in its entirety).

In certain embodiments, the stress protein is a mutated stress protein which has an affinity for a target polypeptide that is greater than a native stress protein. Such mutated stress proteins can be useful when the target polypeptide is phosphorylated or is a phosphopeptide mimetic (such as non-hydrolyzable analogs) or has some other post-translational modification.

The stress proteins can be prepared by purification from tissues, or by recombinant DNA techniques. HSPs can be purified from tissues in the presence of ATP or under acidic conditions (pH 1 to pH 6.9), for subsequent in vitro complexing to one or more polypeptides. See Peng, et al., 1997, J. Immunol. Methods, 204:13-21; Li and Srivastava, 1993, EMBO J. 12:3143-3151 (each of these references is incorporated herein by reference in its entirety). "Purified" stress proteins are substantially free of materials that are associated with the proteins in a cell, in a cell extract, in a cell culture medium, or in an individual. In certain embodiments, the stress protein purified from a tissue is a mixture of different HSPs, for example, hsp70 and hsc70.

Using the defined amino acid or cDNA sequences of a given HSP or a peptide-binding domain thereof, one can make a genetic construct which is transfected into and expressed in a host cell. The recombinant host cells may contain one or more copies of a nucleic acid sequence comprising a sequence that encodes an HSP or a peptide-binding fragment, operably linked with regulatory region(s) that drives the expression of the HSP nucleic acid sequence in the host cell. Recombinant DNA techniques can be readily utilized to generate recombinant HSP genes or fragments of HSP genes, and standard techniques can be used to express such HSP gene fragments. Any nucleic acid sequence encoding an HSP peptide-binding domain, including cDNA and genomic DNA, can be used to prepare the HSPs or peptide-binding fragments of the invention. The nucleic acid sequence can be wild-type or a codon-optimized variant that encodes the same amino acid sequence. An HSP gene fragment containing the peptide-binding domain can be inserted into an appropriate cloning vector and introduced into host cells so that many copies of the gene sequence are generated. A large number of vector-host systems known in the art may be used such as, but not limited to, bacteriophages such as lambda derivatives, or plasmids such as pBR322, pUC plasmid derivatives, the Bluescript vectors (Stratagene) or the pET series of vectors (Novagen). Any technique for mutagenesis known in the art can be used to modify individual nucleotides in a DNA sequence, for purpose of making amino acid substitution(s) in the expressed peptide sequence, or for creating/deleting restriction sites to facilitate further manipulations.

The stress proteins may be expressed as fusion proteins to facilitate recovery and purification from the cells in which they are expressed. For example, the stress proteins may contain a signal sequence leader peptide to direct its translocation across the endoplasmic reticulum membrane for secretion into culture medium. Further, the stress protein may contain an affinity label fused to any portion of the protein not involved in binding to a target polypeptide, for example, the carboxyl terminus. The affinity label can be used to facilitate purification of the protein, by binding to an affinity partner molecule. A variety of affinity labels known in the art may be used, non-limiting examples of which include the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience, incorporated herein by reference in its entirety), glutathione S-transferase (GST; Smith, 1993, Methods Mol. Cell Bio. 4:220-229, incorporated herein by reference in its entirety), the *E. coli* maltose binding protein (Guan et al., 1987, Gene 67:21-30, incorporated herein by reference in its entirety), and various cellulose binding domains (U.S. Pat. Nos. 5,496,934; 5,202,247; 5,137,819; Tomme et al., 1994, Protein Eng. 7:117-123, each of which is incorporated herein by reference in its entirety).

Such recombinant stress proteins can be assayed for peptide binding activity (see, e.g., Klappa et al., 1998, EMBO J., 17:927-935, incorporated herein by reference in its entirety) for their ability to elicit an immune response. In certain embodiments, the recombinant stress protein produced in the host cell is of the same species as the intended recipient of the immunogenic composition (e.g., human).

The stress protein may be bound to the polypeptide(s) non-covalently or covalently. In certain embodiments, the stress protein is non-covalently bound to the polypeptide. Methods of preparing such complexes are set forth infra.

The molar ratio of total polypeptide(s) to total stress protein(s) can be any ratio from about 0.01:1 to about 100:1, including but not limited to about 0.01:1, 0.02:1, 0.05:1. 0.1:1. 0.2:1, 0.5:1, 1:1, 1.5:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1. In certain embodiments, the composition comprises a plurality of complexes each comprising a polypeptide disclosed herein and a stress protein, wherein the molar ratio of the polypeptide to the stress protein in each complex is at least about 1:1 (e.g., about 1.5:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1).

In certain embodiments, the molar ratio of total polypeptide(s) to total stress protein(s) is about 0.5:1 to 5:1. In certain embodiments, the molar ratio of total polypeptide(s) to total stress protein(s) is about 1:1 to 2:1. In certain embodiments, the molar ratio of total polypeptide(s) to total stress protein(s) is about 1:1, 1.25:1, or 1.5:1. Such ratios, particularly the ratios close to 1:1, are advantageous in that the composition does not comprise a great excess of free peptide(s) that is not bound to a stress protein. Since many antigenic peptides comprising MHC-binding epitopes tend to comprise hydrophobic regions, an excess amount of free peptide(s) may tend to aggregate during preparation and storage of the composition. Substantial complexation with a stress protein at a molar ratio of total polypeptide(s) to total stress protein(s) close to 1:1 (e.g., 1:1, 1.25:1, 1.5:1, or 2:1) is enabled by a high binding affinity of the polypeptide to the stress protein. Accordingly, in certain embodiments, the polypeptide binds to an HSP (e.g., Hsc70, Hsp70, Hsp90, Hsp110, Grp170, Gp96, or Calreticulin) with a $K_d$ lower than $10^{-3}$ M, $10^{-4}$ M, $10^{-5}$ M, $10^{-6}$ M, $10^{-7}$ M, $10^{-8}$ M, or $10^{-9}$ M. In certain embodiments, the polypeptide binds to Hsc70 (e.g., human Hsc70) with a $K_d$ of $10^{-3}$ M, $10^{-4}$ M, $10^{-5}$ M, $10^{-6}$ M, $10^{-7}$ M, $10^{-8}$ M, $10^{-9}$ M, or lower.

In certain embodiments, at least 40%, 45%, 50%, 55%, 60%, 65%, 70%, 75%, 80%, 85%, 90%, or 95% of the stress protein binds to the polypeptide in the composition. In certain embodiments, substantially all of the stress protein binds to the polypeptide in the composition.

Any number of different polypeptides can be included in a single composition as disclosed herein. In certain embodiments, the compositions comprise no more than 100 different polypeptides, e.g., 2-50, 2-30, 2-20, 5-20, 5-15, 5-10, or 10-15 different polypeptides. In certain embodiments, each of the polypeptides comprises the same HSP-binding peptide and a different antigenic peptide. In certain embodiments, the composition comprises a single stress protein, wherein the stress protein is capable of binding to the HSP-binding peptide. Pharmaceutical compositions of the invention can be formulated to contain one or more pharmaceutically acceptable carriers or excipients including bulking agents, stabilizing agents, buffering agents, sodium chloride, calcium salts, surfactants, antioxidants, chelating agents, other excipients, and combinations thereof.

Bulking agents are preferred in the preparation of lyophilized formulations of the vaccine composition. Such bulking agents form the crystalline portion of the lyophilized product and may be selected from the group consisting of mannitol, glycine, alanine, and hydroxyethyl starch (HES).

Stabilizing agents may be selected from the group consisting of sucrose, trehalose, raffinose, and arginine. These agents are preferably present in amounts between 1-4%. Sodium chloride can be included in the present formulations preferably in an amount of 100-300 mM, or if used without the aforementioned bulking agents, can be included in the formulations in an amount of between 300-500 mM NaCl. Calcium salts include calcium chloride, calcium gluconate, calcium glubionate, or calcium gluceptate.

Buffering agents can be any physiologically acceptable chemical entity or combination of chemical entities which have a capacity to act as buffers, including but not limited to histidine, potassium phosphate, TRIS [tris-(hydroxymethyl)-aminomethane], BIS-Tris Propane (1,3-bis-[tris-(hydroxymethyl)methylamino]-propane), PIPES [piperazine-N,N'-bis-(2-ethanesulfonic acid)], MOPS [3-(N-morpholino)ethanesulfonic acid], HEPES (N-2-hydroxyethyl-piperazine-N'-2-ethanesulfonic acid), MES [2-(N-morpholino)ethanesulfonic acid], and ACES (N-2-acetamido-2-aminoethanesulfonic acid). Typically, the buffering agent is included in a concentration of 10-50 mM. Specific examples of base buffers include (i) PBS; (ii) 10 mM $KPO_4$, 150 mM NaCl; (iii) 10 mM HEPES, 150 mM NaCl; (iv) 10 mM imidazole, 150 mM NaCl; and (v) 20 mM sodium citrate. Excipients that can be used include (i) glycerol (10%, 20%); (ii) Tween 50 (0.05%, 0.005%); (iii) 9% sucrose; (iv) 20% sorbitol; (v) 10 mM lysine; or (vi) 0.01 mM dextran sulfate.

Surfactants, if present, are preferably in a concentration of 0.1% or less, and may be chosen from the group including but not limited to polysorbate 20, polysorbate 80, pluronic polyols, and BRIJ 35 (polyoxyethylene 23 laurel ether). Antioxidants, if used, must be compatible for use with a pharmaceutical preparation, and are preferably water soluble. Suitable antioxidants include homocysteine, glutathione, lipoic acid, 6-hydroxy-2,5,7,8-tetramethylchroman-2-carboxylic acid (Trolox), methionine, sodium thiosulfate, platinum, glycine-glycine-histidine (tripeptide), and butylatedhydroxytoluene (BHT). Chelating agents should preferably bind metals such as copper and iron with greater affinity than calcium, if a calcium salt is being used in the composition. An exemplary chelator is deferoxamine.

Many formulations known in the art can be used. For example, U.S. Pat. No. 5,763,401 describes a therapeutic formulation, comprising 15-60 mM sucrose, up to 50 mM NaCl, up to 5 mM calcium chloride, 65-400 mM glycine, and up to 50 mM histidine. In some embodiments, the therapeutic formulation is a solution of 9% sucrose in potassium phosphate buffer.

U.S. Pat. No. 5,733,873 (incorporated herein by reference in its entirety) discloses formulations which include between 0.01-1 mg/ml of a surfactant. This patent discloses formulations having the following ranges of excipients: polysorbate 20 or 80 in an amount of at least 0.01 mg/ml, preferably 0.02-1.0 mg/ml; at least 0.1 M NaCl; at least 0.5 mM calcium salt; and at least 1 mM histidine. More particularly, the following specific formulations are also disclosed: (1) 14.7-50-65 mM histidine, 0.31-0.6 M NaCl, 4 mM calcium chloride, 0.001-0.02-0.025% polysorbate 80, with or without 0.1% PEG 4000 or 19.9 mM sucrose; and (2) 20 mg/ml mannitol, 2.67 mg/ml histidine, 18 mg/ml NaCl, 3.7 mM calcium chloride, and 0.23 mg/ml polysorbate 80.

The use of low or high concentrations of sodium chloride has been described, for example U.S. Pat. No. 4,877,608 (incorporated herein by reference in its entirety) teaches formulations with relatively low concentrations of sodium chloride, such as formulations comprising 0.5 mM-15 mM NaCl, 5 mM calcium chloride, 0.2 mM-5 mM histidine, 0.01-10 mM lysine hydrochloride and up to 10% maltose, 10% sucrose, or 5% mannitol.

U.S. Pat. No. 5,605,884 (incorporated herein by reference in its entirety) teaches the use of formulations with relatively high concentrations of sodium chloride. These formulations include 0.35 M-1.2 M NaCl, 1.5-40 mM calcium chloride, 1 mM-50 mM histidine, and up to 10% sugar such as mannitol, sucrose, or maltose. A formulation comprising 0.45 M NaCl, 2.3 mM calcium chloride, and 1.4 mM histidine is exemplified.

International Patent Application WO 96/22107 (incorporated herein by reference in its entirety) describes formulations which include the sugar trehalose, for example formulations comprising: (1) 0.1 M NaCl, 15 mM calcium chloride, 15 mM histidine, and 1.27 M (48%) trehalose; or (2) 0.011% calcium chloride, 0.12% histidine, 0.002% TRIS, 0.002% Tween 80, 0.004% PEG 3350, 7.5% trehalose; and either 0.13% or 1.03% NaCl.

U.S. Pat. No. 5,328,694 (incorporated herein by reference in its entirety) describes a formulation which includes 100-650 mM disaccharide and 100 mM-1.0 M amino acid, for example (1) 0.9 M sucrose, 0.25 M glycine, 0.25 M lysine, and 3 mM calcium chloride; and (2) 0.7 M sucrose, 0.5 M glycine, and 5 mM calcium chloride. Pharmaceutical compositions can be optionally prepared as lyophilized product, which may then be formulated for oral administration or reconstituted to a liquid form for parenteral administration.

In certain embodiments, the composition stimulates a T-cell response against a cell expressing or displaying a polypeptide comprising one or more of the MHC-binding epitopes in a subject to whom the composition is administered. The cell expressing the polypeptide may be a cell comprising a polynucleotide encoding the polypeptide, wherein the polynucleotide is in the genome of the cell, in an episomal vector, or in the genome of a virus that has infected the cell. The cell displaying the polypeptide may not comprise a polynucleotide encoding the polypeptide, and may be produced by contacting the cell with the polypeptide or a derivative thereof.

In certain embodiments, the composition induces in vitro activation of T cells in peripheral blood mononuclear cells (PBMCs) isolated from a subject. The in vitro activation of T cells includes, without limitation, in vitro proliferation of T cells, production of cytokines (e.g., IFNγ) from T cells, and increased surface expression of activation markers (e.g., CD25, CD45RO) on T cells.

5.4.2 Preparation of Complexes of Polypeptides and Stress Proteins

In another aspect, the instant disclosure provides a method of making a vaccine, the method comprising mixing one or more polypeptides as disclosed herein with a purified stress protein in vitro under suitable conditions such that the purified stress protein binds to at least one of the polypeptides. The method is also referred to as a complexing reaction herein. In certain embodiments, two or more purified stress proteins are employed, wherein each purified stress protein binds to at least one of the polypeptides.

The stress protein may be bound to the polypeptide non-covalently or covalently. In certain embodiments, the stress protein is non-covalently bound to the polypeptide. In various embodiments, the complexes formed in vitro are optionally purified. Purified complexes of stress proteins and polypeptides are substantially free of materials that are associated with such complexes in a cell, or in a cell extract. Where purified stress proteins and purified polypeptides are used in an in vitro complexing reaction, the term "purified complex(es)" does not exclude a composition that also comprises free stress proteins and conjugates or peptides not in complexes.

Any stress proteins described supra may be employed in the method of the invention. In certain embodiments, the stress protein is selected from the group consisting of Hsc70, Hsp70, Hsp90, Hsp110, Grp170, Gp96, Calreticulin, a mutant thereof, and combinations of two or more thereof. In one embodiment, the stress protein is an Hsc70, e.g., a human Hsc70. In another embodiment, the stress protein is an Hsp70, e.g., a human Hsp70. In certain embodiments, the stress protein (e.g., human Hsc70 or human Hsp70) is a recombinant protein.

Prior to complexing, HSPs can be pretreated with ATP or exposed to acidic conditions to remove any peptides that may be non-covalently associated with the HSP of interest. Acidic conditions are any pH levels below pH 7, including the ranges pH 1-pH 2, pH 2-pH 3, pH 3-pH 4, pH 4-pH 5, pH 5-pH 6, and pH 6-pH 6.9. When the ATP procedure is used, excess ATP is removed from the preparation by the addition of apyranase as described by Levy, et al., 1991, Cell 67:265-274 (incorporated herein by reference in its entirety). When acidic conditions are used, the buffer is readjusted to neutral pH by the addition of pH modifying reagents.

The molar ratio of total polypeptide(s) to total stress protein(s) can be any ratio from 0.01:1 to 100:1, including but not limited to 0.01:1, 0.02:1, 0.05:1. 0.1:1. 0.2:1, 0.5:1, 1:1, 1.5:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1. In certain embodiments, the composition to be prepared comprises a plurality of complexes each comprising a polypeptide disclosed herein and a stress protein, and the complexing reaction comprises mixing the polypeptides with the stress proteins, wherein the molar ratio of the polypeptide to the stress protein in each complex is at least 1:1 (e.g., about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1).

In certain embodiments, the molar ratio of total polypeptide(s) to total stress protein(s) is about 0.5:1 to 5:1. In certain embodiments, the molar ratio of total polypeptide(s) to total stress protein(s) is about 1:1 to 2:1. In certain embodiments, the molar ratio of total polypeptide(s) to total stress protein(s) is about 1:1, 1.25:1, or 1.5:1. Such ratios, particularly the ratios close to 1:1, are advantageous in that the composition does not comprise a great excess of free peptide(s) that is not bound to a stress protein. Since many antigenic peptides comprising MHC-binding epitopes tend to comprise hydrophobic regions, an excess amount of free peptide(s) may tend to aggregate during preparation and storage of the composition. Substantial complexation with a stress protein at a molar ratio of total polypeptide(s) to total stress protein(s) close to 1:1 (e.g., 1:1, 1.25:1, 1.5:1, or 2:1) is enabled by a high binding affinity of the polypeptide to the stress protein. Accordingly, in certain embodiments, the polypeptide used in the complexing reaction binds to an HSP (e.g., Hsc70, Hsp70, Hsp90, Hsp110, Grp170, Gp96, or Calreticulin) with a $K_d$ lower than $10^{-3}$ M, $10^{-4}$ M, $10^{-5}$ M, $10^{-6}$ M, $10^{-7}$ M, $10^{-8}$ M, or $10^{-9}$ M. In certain embodiments, the polypeptide binds to Hsc70 (e.g., human Hsc70) with a $K_d$ of $10^{-3}$ M, $10^{-4}$ M, $10^{-5}$ M, $10^{-6}$ M, $10^{-7}$ M, $10^{-8}$ M, $10^{-9}$ M, or lower.

The method disclosed herein can be used to prepare a composition (e.g., a pharmaceutical composition or a vaccine) in bulk (e.g., greater than or equal to 30 mg, 50 mg, 100 mg, 200 mg, 300 mg, 500 mg, or 1 g of total peptide and protein). The prepared composition can then be transferred to single-use or multi-use containers, or apportioned to unit dosage forms. Alternatively, method disclosed herein can be used to prepare a composition (e.g., a pharmaceutical composition or a vaccine) in a small amount (e.g., less than or equal to 300 µg, 1 mg, 3 mg, 10 mg, 30 mg, or 100 mg of total peptide and protein). In certain embodiments, the composition is prepared for single use, optionally in a unit dosage form.

In certain embodiments, the total amount of the polypeptide(s) and stress protein in the pharmaceutical composition is about 10 µg to 600 µg (e.g., about 50 µg, 100 µg, 200 µg, 300 µg, 400 µg, or 500 µg). In certain embodiments, the total amount of the polypeptide(s) and stress protein in the pharmaceutical composition is about 300 µg. Amounts of the stress protein(s) and polypeptide(s) in a unit dosage form are disclosed infra.

An exemplary protocol for noncovalent complexing of a population of polypeptides to a stress protein in vitro is provided herein. The population of polypeptides can comprise a mixture of the different polypeptide species of the invention. Then, the mixture is incubated with the purified and/or pretreated stress protein for from 15 minutes to 3 hours (e.g., 1 hour) at from 40 to 50° C. (e.g., 37° C.) in a suitable binding buffer, such as phosphate buffered saline pH 7.4 optionally supplemented with 0.01% Polysorbate 20; a buffer comprising 9% sucrose in potassium phosphate buffer; a buffer comprising 2.7 mM Sodium Phosphate Dibasic, 1.5 mM Potassium Phosphate Monobasic, 150 mM NaCl, pH 7.2; a buffer containing 20 mM sodium phosphate, pH 7.2-7.5, 350-500 mM NaCl, 3 mM $MgCl_2$ and 1 mM phenyl methyl sulfonyl fluoride (PMSF); and the buffer optionally comprising 1 mM ADP. Any buffer may be used that is compatible with the stress protein. The preparations are then optionally purified by centrifugation through a Centricon 10 assembly (Millipore; Billerica, Mass.) to remove any unbound peptide. The non-covalent association of the proteins/peptides with the HSPs can be assayed by High Performance Liquid Chromatography (HPLC), Mass Spectrometry (MS), mixed lymphocyte target cell assay (MLTC), or enzyme-linked immunospot (ELISPOT) assay (Taguchi T, et al., J Immunol Methods 1990; 128: 65-73, incorporated herein by reference in its entirety). Once the complexes have been isolated and diluted, they can be optionally characterized further in animal models using the administration protocols and excipients described herein (see, e.g., Example 2 infra).

Complexes of stress proteins and polypeptides from separate covalent and/or non-covalent complexing reactions can be prepared to form a composition before administration to a subject. In certain embodiments, the composition is prepared within 1, 2, 3, 4, 5, 6, or 7 days before administration to a subject. In certain embodiments, the composition is prepared within 1, 2, 3, 4, 5, 6, 7, or 8 weeks before administration to a subject. In certain embodiments, the composition is prepared within 1, 2, 3, 4, 5, 6, 7, 8, 9, 10, 11, or 12 months before administration to a subject. The composition can optionally be stored at about 4° C., −20° C., or −80° C. after preparation and before use.

In certain embodiments, the complexes prepared by the method disclosed herein are mixed with an adjuvant at bedside just prior to administration to a patient. In certain embodiments, the adjuvant comprises a saponin or an immunostimulatory nucleic acid. In certain embodiments, the adjuvant comprises QS-21. In certain embodiments, the dose of QS-21 is 10 µg, 25 µg, or 50 µg. In certain embodiments, the dose of QS-21 is 50 µg. In certain embodiments, the adjuvant comprises a TLR agonist. In certain embodiments, the TRL agonist is an agonist of TLR4. In certain embodiments, the TRL agonist is an agonist of TLR7 and/or TLR8. In certain embodiments, the TRL agonist is an agonist of TLR9. In certain embodiments, the TRL agonist is an agonist of TLR5.

As an alternative to making non-covalent complexes of stress proteins and polypeptides, the polypeptides can be covalently attached to stress proteins, e.g., by chemical crosslinking or UV crosslinking. Any chemical crosslinking or UV crosslinking methods known in the art (see, e.g., Wong, 1991, Chemistry of Protein Conjugation and Cross-Linking, CRC Press, incorporated herein by reference in its entirety) can be employed. For example, glutaraldehyde crosslinking (see, e.g., Barrios et al., 1992, Eur. J. Immunol. 22: 1365-1372, incorporated herein by reference in its entirety) may be used. In an exemplary protocol, 1-2 mg of HSP-peptide complex is cross-linked in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302, incorporated herein by reference in its entirety).

5.4.3 Vaccines

The compositions disclosed herein are useful as vaccines. Accordingly, in another aspect, the instant disclosure provides a vaccine formulation. The vaccine formulation may be prepared by any method that results in a stable, sterile, preferably injectable formulation.

In certain embodiments, the vaccine comprises one or more compositions disclosed herein and one or more adjuvants. A variety of adjuvants may be employed, including, for example, systemic adjuvants and mucosal adjuvants. A systemic adjuvant is an adjuvant that can be delivered parenterally. Systemic adjuvants include adjuvants that create a depot effect, adjuvants that stimulate the immune system, and adjuvants that do both.

An adjuvant that creates a depot effect is an adjuvant that causes the antigen to be slowly released in the body, thus prolonging the exposure of immune cells to the antigen. This class of adjuvants includes alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

Other adjuvants stimulate the immune system, for instance, cause an immune cell to produce and secrete cytokines or IgG. This class of adjuvants includes immunostimulatory nucleic acids, such as CpG oligonucleotides; saponins purified from the bark of the Q. saponaria tree, such as QS-21; poly[di(carboxylatophenoxy)phosphazene (PCPP polymer; Virus Research Institute, USA); RNA mimetics such as polyinosinic:polycytidylic acid (poly I:C) or poly I:C stabilized with poly-lysine (poly-ICLC [Hiltonol®; Oncovir, Inc.]; derivatives of lipopolysaccharides (LPS) such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Other systemic adjuvants are adjuvants that create a depot effect and stimulate the immune system. These compounds have both of the above-identified functions of systemic adjuvants. This class of adjuvants includes but is not limited to ISCOMs (Immunostimulating complexes which contain mixed saponins, lipids and form virus-sized particles with pores that can hold antigen; CSL, Melbourne, Australia); AS01 which is a liposome based formulation containing MPL and QS-21 (GlaxoSmithKline, Belgium); AS02 (GlaxoSmithKline, which is an oil-in-water emulsion containing MPL and QS-21: GlaxoSmithKline, Rixensart, Belgium); AS04 (GlaxoSmithKline, which contains alum and MPL; GSK, Belgium); AS15 which is a liposome based formulation containing CpG oligonucleotides, MPL and QS-21 (GlaxoSmithKline, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

The mucosal adjuvants useful according to the invention are adjuvants that are capable of inducing a mucosal immune response in a subject when administered to a mucosal surface in conjunction with complexes of the invention. Mucosal adjuvants include CpG nucleic acids (e.g. PCT published patent application WO 99/61056, incorporated herein by reference in its entirety), bacterial toxins: e.g., Cholera toxin (CT), CT derivatives including but not limited to CT B subunit (CTB); CTD53 (Val to Asp); CTK97 (Val to Lys); CTK104 (Tyr to Lys); CTD53/K63 (Val to Asp, Ser to Lys); CTH54 (Arg to His); CTN107 (His to Asn); CTE114 (Ser to Glu); CTE112K (Glu to Lys); CTS61F (Ser to Phe); CTS 106 (Pro to Lys); and CTK63 (Ser to Lys), Zonula occludens toxin (zot), *Escherichia coli* heat-labile enterotoxin, Labile Toxin (LT), LT derivatives including but not limited to LT B subunit (LTB); LT7K (Arg to Lys); LT61F (Ser to Phe); LT112K (Glu to Lys); LT118E (Gly to Glu); LT146E (Arg to Glu); LT192G (Arg to Gly); LTK63 (Ser to Lys); and LTR72 (Ala to Arg), Pertussis toxin, PT. including PT-9K/129G; Toxin derivatives (see below); Lipid A derivatives (e.g., monophosphoryl lipid A, MPL); Muramyl Dipeptide (MDP) derivatives; bacterial outer membrane proteins (e.g., outer surface protein A (OspA) lipoprotein of *Borrelia burgdorferi*, outer membrane protein of *Neisseria meningitidis*); oil-in-water emulsions (e.g., MF59; aluminum salts (Isaka et al., 1998, 1999); and Saponins (e.g., QS-21, e.g., QS-21 Stimulon®, Antigenics LLC, Lexington, Mass.), ISCOMs, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micelle-forming agent; IDEC Pharmaceuticals Corporation, San Diego, Calif.); Syntex Adjuvant Formulation (SAF; Syntex Chemicals, Inc., Boulder, Colo.); poly[di(carboxylatophenoxy)]

phosphazene (PCPP polymer; Virus Research Institute, USA) and *Leishmania* elongation factor (Corixa Corporation, Seattle, Wash.).

In certain embodiments, the adjuvant added to the compositions disclosed herein comprises a saponin and/or an immunostimulatory nucleic acid. In certain embodiments, the adjuvant added to the composition comprises or further comprises QS-21.

In certain embodiments, the adjuvant added to the compositions disclosed herein comprises a Toll-like receptor (TLR) agonist. In certain embodiments, the TRL agonist is an agonist of TLR4. In certain embodiments, the TRL agonist is an agonist of TLR7 and/or TLR8. In certain embodiments, the TRL agonist is an agonist of TLR9. In certain embodiments, the TRL agonist is an agonist of TLR5.

The compositions of the invention described herein may be combined with an adjuvant in several ways. For example, different polypeptides may be mixed together first to form a mixture and then complexed with stress protein(s) and/or adjuvant(s) to form a composition. As another example, different polypeptides may be complexed individually with a stress protein and/or adjuvant(s), and the resulting batches of complexes may then be mixed to form a composition.

The adjuvant can be administered prior to, during, or following administration of the compositions comprising complexes of stress protein and polypeptides. Administration of the adjuvant and the compositions can be at the same or different administration sites.

5.4.4 Unit Dosage Forms

In another aspect, the instant disclosure provides a unit dosage form of a pharmaceutical composition or vaccine disclosed herein.

The amounts and concentrations of the polypeptides, stress proteins, and/or adjuvants at which the efficacy of a vaccine formulation of the invention may vary depending on the chemical nature and the potency of the polypeptides, stress proteins, and/or adjuvants. Typically, the starting amounts and concentrations in the vaccine formulation are the ones conventionally used for eliciting the desired immune response, using the conventional routes of administration, e.g., intramuscular injection. The amounts and concentrations of the peptides, conjugates, stress proteins, and/or adjuvants can then be adjusted, e.g., by dilution using a diluent, so that an effective protective immune response is achieved as assessed using standard methods known in the art (e.g., determined by the antibody or T-cell response to the vaccine formulation relative to a control formulation).

In certain embodiments, the total amount of the polypeptides and stress protein in the pharmaceutical composition is about 10 μg to 600 μg (e.g., about 50 μg, 100 μg, 200 μg, 300 μg, 400 μg, or 500 μg). In certain embodiments, the total amount of the polypeptides and stress protein in the pharmaceutical composition is about 300 μg. In certain embodiments, the amount of the stress protein in the composition is about 250 μg to 290 μg.

In certain embodiments, the amount of the stress protein in the pharmaceutical composition is about 10 μg to 600 μg (e.g., about 50 μg, 100 μg, 200 μg, 300 μg, 400 μg, or 500 μg). In certain embodiments, the amount of the stress protein in the pharmaceutical composition is about 300 μg. The amount of the polypeptide is calculated based on a designated molar ratio and the molecular weight of the polypeptides.

In certain embodiments, the total molar amount of the polypeptides in the unit dosage form of the pharmaceutical composition is about 0.1 to 10 nmol (e.g., about 0.1 nmol, 0.5 nmol, 1 nmol, 2 nmol, 3 nmol, 4 nmol, 5 nmol, 6 nmol, 7 nmol, 8 nmol, 9 nmol, or 10 nmol). In certain embodiments, the total molar amount of the polypeptides in the unit dosage form of the pharmaceutical composition is about 4 nmol. In certain embodiments, the total molar amount of the polypeptides in the unit dosage form of the pharmaceutical composition is about 5 nmol.

The molar ratio of total polypeptides to total stress proteins can be any ratio from about 0.01:1 to about 100:1, including but not limited to about 0.01:1, 0.02:1, 0.05:1. 0.1:1. 0.2:1, 0.5:1, 1:1, 1.5:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1. In certain embodiments, the composition comprises a plurality of complexes each comprising a polypeptide and a stress protein, wherein the molar ratio of the polypeptide to the stress protein in each complex is at least about 1:1 (e.g., about 1.5:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1). In certain embodiments, the molar ratio of total polypeptide(s) to total stress protein(s) is about 0.5:1 to 5:1.

In certain embodiments, the molar ratio of total polypeptide(s) to total stress protein(s) is about 1:1 to 2:1. In certain embodiments, the molar ratio of total polypeptide(s) to total stress protein(s) is about 1:1, 1.25:1, or 1.5:1. Such ratios, particularly the ratios close to 1:1, are advantageous in that the composition does not comprise a great excess of free peptide(s) that is not bound to a stress protein. Since many antigenic peptides comprising MHC-binding epitopes tend to comprise hydrophobic regions, an excess amount of free peptide(s) may tend to aggregate during preparation and storage of the composition. Substantial complexation with a stress protein at a molar ratio of total polypeptide(s) to total stress protein(s) close to 1:1 (e.g., 1:1, 1.25:1, 1.5:1, or 2:1) is enabled by a high binding affinity of the polypeptide to the stress protein. Accordingly, in certain embodiments, the polypeptide binds to an HSP (e.g., Hsc70, Hsp70, Hsp90, Hsp110, Grp170, Gp96, or Calreticulin) with a $K_d$ lower than $10^{-3}$ M, $10^{-4}$ M, $10^{-5}$ M, $10^{-6}$ M, $10^{-7}$ M, $10^{-8}$ M, or $10^{-9}$ M. In certain embodiments, the polypeptide binds to Hsc70 (e.g., human Hsc70) with a $K_d$ of $10^{-3}$ M, $10^{-4}$ M, $10^{-5}$ M, $10^{-6}$ M, $10^{-7}$ M, $10^{-8}$ M, $10^{-9}$ M, or lower.

Methods of calculating the amounts of components in the unit dosage form are provided. For example, in certain embodiments, the polypeptides have an average molecular weight of about 3 kD, and the molecular weight of Hsc70 is about 71 kD. Assuming in one embodiment that the total amount of the polypeptides and stress protein in the pharmaceutical composition is 300 μg, and the molar ratio of the polypeptides to hsc70 is 1.5:1. The molar amount of Hsc70 can be calculated as 300 μg divided by 71 kD+1.5×3 kD, resulting in about 4.0 nmol, and the mass amount of Hsc70 can be calculated by multiplying the molar amount with 71 kD, resulting in about 280 kD. The total molar amount of the polypeptides can be calculated as 1.5×4.0 nmol, resulting in 6.0 nmol. If 10 different polypeptides are employed, the molar amount of each polypeptide is 0.60 nmol. Assuming in another embodiment that a 300 μg dose of Hsc70 is intended to be included in a unit dosage form, and the molar ratio of polypeptides to Hsc70 is 1.5:1. The total molar amount of the polypeptides can be calculated as 300 μg divided by 71 kD then times 1.5, resulting in 6.3 nmol. If 10 different polypeptides are employed, the molar amount of each polypeptide is 0.63 nmol. In cases where one or more of the variables are different from those in the examples, the quantities of the stress proteins and of the polypeptides are scaled accordingly.

It is further appreciated that the unit dosage form can optionally comprise one or more adjuvants as disclosed supra. In certain embodiments, the adjuvant comprises a saponin and/or an immunostimulatory nucleic acid. In certain embodiments, the adjuvant comprises or further comprises QS-21. In certain embodiments, the amount of QS-21 in the unit dosage form of pharmaceutical composition is 10 µg, 25 µg, or 50 µg. In certain embodiments, the amount of QS-21 in the unit dosage form of pharmaceutical composition is 50 µg. In certain embodiments, the adjuvant comprises a Toll-like receptor (TLR) agonist. In certain embodiments, the TRL agonist is an agonist of TLR4. In certain embodiments, the TRL agonist is an agonist of TLR7 and/or TLR8. In certain embodiments, the TRL agonist is an agonist of TLR9. In certain embodiments, the TRL agonist is an agonist of TLR5.

5.5 Methods of Use

The compositions (e.g., pharmaceutical compositions), vaccine formulations, and unit dosage forms disclosed herein are useful for inducing a cellular immune response. Stress proteins can deliver immunogenic peptides through the cross-presentation pathway in antigen presenting cells (APCs) (e.g., macrophages and dendritic cells (DCs) via membrane receptors (mainly CD91) or by binding to Toll-like receptors, thereby leading to activation of $CD8^+$ and $CD4^+$ T cells. Internalization of a stress protein-peptide complex results in functional maturation of the APCs with chemokine and cytokine production leading to activation of natural killer cells (NK), monocytes and Th1 and Th-2-mediated immune responses.

Accordingly, in one aspect, the instant disclosure provides a method of inducing a cellular immune response to an antigenic peptide in a subject, the method comprising administering to the subject an effective amount of a composition, vaccine formulations, or unit dosage form as disclosed herein. In another aspect, the instant disclosure provides a method of treating a disease (e.g., cancer or infection) in a subject, the method comprising administering to the subject an effective amount of a composition, vaccine formulations, or unit dosage form as disclosed herein. The compositions (e.g., pharmaceutical compositions), vaccine formulations, and unit dosage forms disclosed herein can also be used in preparing a medicament or vaccine for the treatment of a subject.

In various embodiments, such subjects can be an animal, e.g., a mammal, a non-human primate, and a human. The term "animal" includes companion animals, such as cats and dogs; zoo animals; wild animals, including deer, foxes and raccoons; farm animals, livestock and fowl, including horses, cattle, sheep, pigs, turkeys, ducks, and chickens, and laboratory animals, such as rodents, rabbits, and guinea pigs. In certain embodiments, the subject has cancer. In certain embodiments, the subject has infection of a pathogenic microbe.

5.5.1 Treatment of Cancer

The compositions, vaccine formulations, or unit dosage forms of the invention can be used alone or in combination with other therapies for the treatment of cancer. One or more of the MHC-binding epitopes in the HSP-binding antigenic conjugate(s) or peptide(s) can be present in the subject's cancer cells. In certain embodiments, one or more of the MHC-binding epitopes are common to or frequently found in the type and/or stage of the cancer. As used herein, the term "frequently found in cancers" refers to one or more mutant MHC-binding epitopes that are found in greater than 5% of cancers. In certain embodiments, one or more of the MHC-binding epitopes are specific to the cancer of the subject.

Cancers that can be treated using the compositions, vaccine formulations, or unit dosage forms of the invention include, without limitation, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage or metastatic cancer. In certain embodiments, the cancer is associated with elevated PD-1 activity (e.g., elevated PD-1 expression).

In one embodiment, the cancer is chosen from a lung cancer (e.g., lung adenocarcinoma or a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma), a liver cancer (e.g., hepatocellular carcinoma or intrahepatic cholangiocellular carcinoma), a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC), anal cancer, gastro-esophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease). In one embodiment, the cancer is NSCLC. In one embodiment, the cancer is a renal cell carcinoma. In one embodiment, the cancer is an ovarian cancer, optionally wherein the ovarian cancer is associated with human papillomavirus (HPV) infection. In a specific embodiment, the ovarian cancer is a platinum-refractory ovarian cancer.

In one embodiment, the cancer is a hematological cancer, for example, a leukemia, a lymphoma, or a myeloma. In one embodiment, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CML), chronic myeloid leukemia (CML), chronic myelomonocytic leukemia (CMML), chronic lymphocytic leukemia (CLL), or hairy cell leukemia. In one embodiment, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, or extranodal marginal zone lymphoma. In one embodiment the cancer is a myeloma, for example, multiple myeloma.

In another embodiment, the cancer is chosen from a carcinoma (e.g., advanced or metastatic carcinoma), melanoma or a lung carcinoma, e.g., a non-small cell lung carcinoma.

In one embodiment, the cancer is a lung cancer, e.g., a lung adenocarcinoma, non-small cell lung cancer or small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the compositions, vaccine formulations, or unit dosage forms disclosed herein is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

The compositions, vaccine formulations, or unit dosage forms of the invention may be administered when a cancer is detected, or prior to or during an episode of recurrence. Administration can begin at the first sign of cancer or recurrence, followed by boosting doses until at least symptoms are substantially abated and for a period thereafter.

In some embodiments, the compositions can be administered to a subject with cancer who has undergone tumor resection surgery that results in an insufficient amount of resected tumor tissue (e.g., less than 7 g, less than 6 g, less than 5 g, less than 4 g, less than 3 g, less than 2 g, or less than 1 g of resected tumor tissue) for production of a therapeutically effective amount of an autologous cancer vaccine comprising a representative set of antigens collected from the resected tumor tissue. See, for example, cancer vaccines described in Expert Opin. Biol. Ther. 2009 February; 9(2):179-86; incorporated herein by reference.

The compositions, vaccine formulations, and unit dosage forms of the invention can also be used for immunization against recurrence of cancers. Prophylactic administration of a composition to an individual can confer protection against a future recurrence of a cancer.

5.5.2 Treatment of Infection

The compositions, vaccine formulations, or unit dosage forms of the invention can be used alone or in combination with other therapies for the treatment of a microbial infection (e.g., a pathogenic microbial infection). One or more of the MHC-binding epitopes in the HSP-binding antigenic conjugate(s) or peptide(s) can be identified from the microbe. In certain embodiments, one or more of the MHC-binding epitopes are present at the surface of the microbe or a cell infected with the microbe.

Infections that can be treated using the compositions, vaccine formulations, or unit dosage forms of the invention include, without limitation, a viral infection, a bacterial infection, a fungal infection, a protozoal infection, or a parasitic infection.

Viral infections that can be treated by the compositions, vaccine formulations, or unit dosage forms disclosed herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus (e.g., human papillomavirus (HPV)), papova virus, cytomegalovirus, echinovirus, arbovirus, hantavirus, coxsackie virus, mumps virus, measles virus, rubella virus, polio virus, Epstein Barr virus (EBV), human immunodeficiency virus type I (HIV-I), human immunodeficiency virus type II (HIV-II), dengue virus, smallpox virus, rabies virus, rabies virus, and Zika virus. Viral diseases caused by any of these viruses that can be treated in accordance with the methods described herein include, but are not limited to, fever, immunodeficiency, viral meningitis, and encephalitis.

Bacterial infections that can be treated by the compositions, vaccine formulations, or unit dosage forms disclosed herein include, but are not limited to, infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by any of these bacteria that can be treated in accordance with the methods described herein include, but are not limited to, Mycobacteria *rickettsia, Mycoplasma, Neisseria, S. pneumonia, Borrelia burgdorferi* (Lyme disease), *Bacillus antracis* (anthrax), tetanus, *Streptococcus, Staphylococcus, mycobacterium*, pertissus, cholera, plague, diptheria, *chlamydia, S. aureus* and *legionella*.

Fungal infections that can be treated by the compositions, vaccine formulations, or unit dosage forms disclosed herein include, but are not limited to, infections caused by *Candida* (e.g., *Candida glabrata*), *Pneumocystis carinii, Fusarium keratitis, coccidioidal, Aspergillus niger, Cryptococcus neoformans*, and *Curvularia geniculata*. Fungal diseases caused by any of these bacteria that can be treated in accordance with the methods described herein include, but are not limited to, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, fungal peritonitis, staphylococcal endophthalmitis, sporotrichosis, and dermatophytosis.

Protozoal infections that can be treated by the compositions, vaccine formulations, or unit dosage forms disclosed herein include, but are not limited to, infections caused by *leishmania*, coccidiosis, *trypanosoma schistosoma*, and malaria.

Parasitic infections that can be treated by the compositions, vaccine formulations, or unit dosage forms disclosed herein include, but are not limited to, infections caused by *chlamydia* and *rickettsia*.

The compositions, vaccine formulations, and unit dosage forms of the invention can be used for immunization against subjects who have been diagnosed, by any medical methods known in the art, to have infections. They can be used for immunization against subjects who have been exposed to a pathogenic microbe, will be exposed to a pathogenic microbe, or are otherwise at a high risk of contracting an infectious disease, for prophylaxis.

5.5.3 Combination Therapy

Combination therapy refers to the use of compositions, vaccine formulations, or unit dosage forms of the invention, as a first modality, with a second modality to treat cancer or infections. Accordingly, in certain embodiments, the instant disclosure provides a method of inducing a cellular immune response to an antigenic peptide in a subject as disclosed herein, or a method of treating a disease in a subject as disclosed herein, the method comprising administering to the subject an effective amount of (a) a composition, vaccine formulations, or unit dosage form as disclosed herein and (b) a second modality.

In one embodiment, the second modality is a non-HSP modality, e.g., a modality that does not comprise HSP as a component. This approach is commonly termed combination therapy, adjunctive therapy or conjunctive therapy (the terms are used interchangeably). With combination therapy, additive potency or additive therapeutic effect can be observed. Synergistic outcomes are sought where the therapeutic efficacy is greater than additive. The use of combination therapy can also provide better therapeutic profiles than the administration of either the first or the second modality alone.

The additive or synergistic effect may allow for a reduction in the dosage and/or dosing frequency of either or both modalities to mitigate adverse effects. In certain embodiments, the second modality administered alone is not clinically adequate to treat the subject (e.g., the subject is non-responsive or refractory to the single modality), such that the subject needs an additional modality. In certain embodiments, the subject has responded to the second modality, yet suffers from side effects, relapses, develops resistance, etc., such that the subject needs an additional modality. Methods of the invention comprising administration of the compositions, vaccine formulations, or unit dosage forms of the invention to such subjects to improve the therapeutic effectiveness of the second modality. The effectiveness of a treatment modality can be assayed in vivo or in vitro using methods known in the art.

In one embodiment, a lesser amount of the second modality is required to produce a therapeutic benefit in a subject. In specific embodiments, a reduction of about 10%, 20%, 30%, 40% and 50% of the amount of second modality can be achieved. The amount of the second modality, including amounts in a range that does not produce any observable therapeutic benefits, can be determined by dose-response experiments conducted in animal models by methods well known in the art.

In certain embodiments, the second modality comprises a TCR, e.g., a soluble TCR or a cell expressing a TCR. In certain embodiments, the second modality comprises a cell expressing a chimeric antigen receptor (CAR). In certain embodiments, the cell expressing the TCR or CAR is a T cell. In a particular embodiment, the TCR or CAR binds to (e.g., specifically binds to) at least one MHC-binding epitope in the composition, vaccine formulation, or unit dosage form of the invention.

In certain embodiments, the second modality comprises a TCR mimic antibody. In certain embodiments, the TCR mimic antibody is an antibody that specifically binds to a peptide-MHC complex. Non-limiting examples of TCR mimic antibodies are disclosed in U.S. Pat. No. 9,074,000, U.S. Publication Nos. US 2009/0304679 A1 and US 2014/0134191 A1, all of which are incorporated herein by reference in their entireties. In a particular embodiment, the TCR mimic antibody binds to (e.g., specifically binds to) at least one MHC-binding epitope in the composition, vaccine formulation, or unit dosage form of the invention.

In certain embodiments, the second modality comprises a checkpoint targeting agent. In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-CEACAM1 antibody, an agonist anti-CD137 antibody, an antagonist anti-TIGIT antibody, an antagonist anti-VISTA antibody, an agonist anti-GITR antibody, and an agonist anti-OX40 antibody.

In certain embodiments, an anti-PD-1 antibody is used as the second modality in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used as the second modality in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, a compound that targets an immunomodulatory enzyme(s) such as IDO (indoleamine-(2,3)-dioxygenase) and/or TDO (tryptophan 2,3-dioxygenase) is used as the second modality in methods disclosed herein. Therefore, in one embodiment, the compound targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, an anti-TIM-3 (e.g., human TIM-3) antibody disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, the second modality comprises a different vaccine (e.g., a peptide vaccine, a DNA vaccine, or an RNA vaccine) for treating cancer or infection. In certain embodiments, the vaccine is a heat shock protein based tumor vaccine or a heat shock protein based pathogen vaccine (e.g., a vaccine as described in WO 2016/183486, which is incorporated herein by reference in its entirety). In a specific embodiment, the second modality comprises a stress protein-based vaccine. For example, in certain embodiments, the second modality comprises a composition, vaccine formulation, or unit dosage form as disclosed herein that is different from the first modality. In certain embodiments, the second modality comprises a composition, vaccine formulation, or unit dosage form analogous to those disclosed herein except for having a different sequence of the HSP-binding peptide. In certain embodiments, the stress protein-based vaccine is derived from a tumor preparation, such that the immunity elicited by the vaccine is specifically directed against the unique antigenic peptide repertoire expressed by the cancer of each subject.

In certain embodiments, the second modality comprises one or more adjuvants, such as the ones disclosed supra that may be included in the vaccine formulation disclosed herein. In certain embodiments, the second modality comprises a saponin, an immunostimulatory nucleic acid, and/or QS-21. In certain embodiments, the second modality comprises a Toll-like receptor (TLR) agonist. In certain embodiments, the TRL agonist is an agonist of TLR4. In certain embodiments, the TRL agonist is an agonist of TLR7 and/or TLR8. In certain embodiments, the TRL agonist is an agonist of TLR9. In certain embodiments, the TRL agonist is an agonist of TLR5.

In certain embodiments, the second modality comprises one or more of the agents selected from the group consisting of lenalidomide, dexamethasone, interleukin-2, recombinant interferon alfa-2b, and peginterferon alfa-2b.

In certain embodiments, where the pharmaceutical composition, vaccine formulation, or unit dosage form is used for treating a subject having cancer, the second modality comprises a chemotherapeutic or a radiotherapeutic. In certain embodiments, the chemotherapeutic agent is a hypomethylating agent (e.g., azacitidine).

In certain embodiments, where the pharmaceutical composition, vaccine formulation, or unit dosage form is used for treating a subject having infection of a pathogenic microbe, the second modality comprises one or more anti-infective interventions (e.g., antivirals, antibacterials, antifungals, or anti-helminthics) for the treatment of the infectious disease.

The composition, vaccine formulation, or unit dosage form of the invention can be administered separately, sequentially, or concurrently from the second modality (e.g., chemotherapeutic, radiotherapeutic, checkpoint targeting agent, IDO inhibitor, vaccine, adjuvant, soluble TCR, cell expressing a TCR, cell expressing a CAR, and/or TCR mimic antibody), by the same or different delivery routes.

5.5.4 Dosage Regimen

The dosage of the compositions or vaccine formulations disclosed herein, and the dosage of any additional treatment modality if combination therapy is to be administered, depends to a large extent on the weight and general state of health of the subject being treated, as well as the frequency of treatment and the route of administration. Amounts effective for this use will also depend on the stage and severity of the disease and the judgment of the prescribing physician, but generally range for the initial immunization (that is, for therapeutic administration) from about 1.0 µg to about 1000 µg (1 mg) (including, for example, 10, 20, 25, 30, 40, 50, 60, 70, 80, 90, 100, 150, 200, 240, 250, 300, 350, 400, 450, 500, 550, 600, 650, 700, 750, 800, 850, 900, 950, or 1000 µg) of any one of the compositions disclosed herein for a 70 kg patient, followed by boosting dosages of from about 1.0 μg to about 1000 μg of the composition (including, for example, 10, 20, 25, 30, 40, 50, 60, 70, 80, 90, 100, 150, 200, 250, 300, 350, 400, 450, 500, 550, 600, 650, 700, 750, 800, 850, 900, 950, or 1000 μg) pursuant to a boosting regimen over weeks to months depending upon the patient's response and condition by measuring specific CTL activity in the patient's blood. Regimens for continuing therapy, including site, dose and frequency may be guided by the initial response and clinical judgment. Dosage ranges and regimens for adjuvants are known to those in the art, see, e.g., Vogel and Powell, 1995, A Compendium of Vaccine Adjuvants and Excipients; M. F. Powell, M. J. Newman (eds.), Plenum Press, New York, pages 141-228.

Preferred adjuvants include QS-21, e.g., QS-21 Stimulon®, and CpG oligonucleotides. Exemplary dosage ranges for QS-21 are 1 μg to 200 μg per administration. In other embodiments, dosages for QS-21 can be 10, 25, and 50 μg per administration. In certain embodiments, the adjuvant comprises a Toll-like receptor (TLR) agonist. In certain embodiments, the TRL agonist is an agonist of TLR4. In certain embodiments, the TRL agonist is an agonist of TLR7 and/or TLR8. In certain embodiments, the TRL agonist is an agonist of TLR9. In certain embodiments, the TRL agonist is an agonist of TLR5.

In certain embodiments, the administered amount of compositions depends on the route of administration and the type of HSPs in the compositions. For example, the amount of HSP in the compositions can range, for example, from 5 to 1000 μg (1 mg) per administration. In certain embodiments, the administered amount of compositions comprising Hsc70-, Hsp70- and/or Gp96-polypeptide complexes is, for example, 5, 10, 20, 25, 30, 40, 50, 60, 70, 80, 90, 100, 200, 250, 300, 400, 500, 600, 700, 750, 800, 900, or 1000 μg. In certain embodiments, the administered amount of the composition is in the range of about 10 to 600 μg per administration and about 5 to 100 μg if the composition is administered intradermally. In certain embodiments, the administered amount of the composition is about 5 μg to 600 μg, about 5 μg to 300 μg, about 5 μg to 150 μg, or about 5 μg to 60 μg. In certain embodiments, the administered amount of the composition is less than 100 μg. In certain embodiments, the administered amount of the composition is about 5 μg, 25 μg, 50 μg, or 240 μg. In certain embodiments, the compositions comprising complexes of stress proteins and polypeptides are purified.

In one embodiment of a therapeutic regimen, a dosage substantially equivalent to that observed to be effective in smaller non-human animals (e.g., mice or guinea pigs) is effective for human administration, optionally subject to a correction factor not exceeding a fifty fold increase, based on the relative lymph node sizes in such mammals and in humans. Specifically, interspecies dose-response equivalence for stress proteins (or HSPs) noncovalently bound to or mixed with antigenic molecules for a human dose is estimated as the product of the therapeutic dosage observed in mice and a single scaling ratio, not exceeding a fifty fold increase. In certain embodiment, the dosages of the composition can be much smaller than the dosage estimated by extrapolation.

The doses recited above can be given once or repeatedly, such as daily, every other day, weekly, biweekly, or monthly, for a period up to a year or over a year. Doses are preferably given once every 28 days for a period of about 52 weeks or more.

In one embodiment, the compositions are administered to a subject at reasonably the same time as an additional treatment modality or modalities. This method provides that the two administrations are performed within a time frame of less than one minute to about five minutes, or up to about sixty minutes from each other, for example, at the same doctor's visit.

In another embodiment, the compositions and an additional treatment modality or modalities are administered at exactly the same time.

In yet another embodiment the compositions and an additional treatment modality or modalities are administered in a sequence and within a time interval such that the complexes of the invention and the additional treatment modality or modalities can act together to provide an increased benefit than if they were administered alone.

In another embodiment, the compositions and an additional treatment modality or modalities are administered sufficiently close in time so as to provide the desired therapeutic or prophylactic outcome. Each can be administered simultaneously or separately, in any appropriate form and by any suitable route. In one embodiment, the complexes of the invention and the additional treatment modality or modalities are administered by different routes of administration. In an alternate embodiment, each is administered by the same route of administration. The compositions can be administered at the same or different sites, e.g. arm and leg. When administered simultaneously, the compositions and an additional treatment modality or modalities may or may not be administered in admixture or at the same site of administration by the same route of administration.

In various embodiments, the compositions and an additional treatment modality or modalities are administered less than 1 hour apart, at about 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In other embodiments, the compositions and a vaccine composition are administered 2 to 4 days apart, 4 to 6 days apart, 1 week a part, 1 to 2 weeks apart, 2 to 4 weeks apart, one month apart, 1 to 2 months apart, or 2 or more months apart. In preferred embodiments, the compositions and an additional treatment modality or modalities are administered in a time frame where both are still active. One skilled in the art would be able to determine such a time frame by determining the half-life of each administered component.

In certain embodiments, the compositions are administered to the subject weekly for at least four weeks. In certain embodiments, after the four weekly doses, at least 2 (e.g., 2, 3, 4, 5, 6, 7, 8, 9, 10, 11, 12, 13, 14, 15, 16, 17, 18, 19, or 20) further doses of the compositions are administered biweekly to the subject. In certain embodiments, the compositions administered as a booster three months after the final weekly or biweekly dose. The three monthly booster can be administered for the life of the subject (e.g., at least 1, 2, 3, 4, 5, 6, 7, 8, 9, 10, 11, 12, 13, 14, 15, 16, 17, 18, 19, 20, 25, 30, 40, 50, or more years). In certain embodiments, the total number of doses of the compositions administered to the subject is 1, 2, 3, 4, 5, 6, 7, 8, 9, 10, 11, 12, 13, 14, 15, 16, 17, 18, 19, or 20.

In one embodiment, the compositions and an additional treatment modality or modalities are administered within the same patient visit. In certain embodiments, the compositions are administered prior to the administration of an additional treatment modality or modalities. In an alternate specific embodiment, the compositions are administered subsequent to the administration of an additional treatment modality or modalities.

In certain embodiments, the compositions and an additional treatment modality or modalities are cyclically administered to a subject. Cycling therapy involves the administration of the compositions for a period of time, followed by the administration of a modality for a period of time and repeating this sequential administration. Cycling therapy can reduce the development of resistance to one or more of the therapies, avoid or reduce the side effects of one of the therapies, and/or improve the efficacy of the treatment. In such embodiments, the disclosure contemplates the alternating administration of the compositions followed by the administration of a modality 4 to 6 days later, preferable 2 to 4 days, later, more preferably 1 to 2 days later, wherein such a cycle may be repeated as many times as desired. In certain embodiments, the compositions and the modality are alternately administered in a cycle of less than 3 weeks, once every two weeks, once every 10 days or once every week. In certain embodiments, the compositions are administered to a subject within a time frame of one hour to twenty four hours after the administration of a modality. The time frame can be extended further to a few days or more if a slow- or continuous-release type of modality delivery system is used.

5.5.5 Routes of Administration

The compositions disclosed herein may be administered using any desired route of administration. Many methods may be used to introduce the compositions described above, including but not limited to, oral, intradermal, intramuscular, intraperitoneal, intravenous, subcutaneous, mucosal, intranasal, intra-tumoral, and intra-lymph node routes. Non-mucosal routes of administration include, but are not limited to, intradermal and topical administration. Mucosal routes of administration include, but are not limited to, oral, rectal and nasal administration. Advantages of intradermal administration include use of lower doses and rapid absorption, respectively. Advantages of subcutaneous or intramuscular administration include suitability for some insoluble suspensions and oily suspensions, respectively. Preparations for mucosal administrations are suitable in various formulations as described below.

Solubility and the site of the administration are factors which should be considered when choosing the route of administration of the compositions. The mode of administration can be varied between multiple routes of administration, including those listed above.

If the compositions are water-soluble, then it may be formulated in an appropriate buffer, for example, phosphate buffered saline or other physiologically compatible solutions, preferably sterile. Alternatively, if a composition has poor solubility in aqueous solvents, then it may be formulated with a non-ionic surfactant such as Tween, or polyethylene glycol. Thus, the compositions may be formulated for administration by inhalation or insufflation (either through the mouth or the nose) or oral, buccal, parenteral, or rectal administration.

For oral administration, the composition may be in liquid form, for example, solutions, syrups or suspensions, or may be presented as a drug product for reconstitution with water or other suitable vehicle before use. Such a liquid preparation may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

The compositions for oral administration may be suitably formulated to be released in a controlled and/or timed manner.

For buccal administration, the compositions may take the form of tablets or lozenges formulated in conventional manner.

The preparation may be formulated for parenteral administration by injection, e.g., by bolus injection or continuous infusion. Formulations for injection may be presented in unit dosage form, e.g., in ampoules or in multi-dose containers, with an added preservative. The preparation may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The preparation may also be formulated in a rectal preparation such as a suppository or retention enema, e.g., containing conventional suppository bases such as cocoa butter or other glycerides.

In addition to the formulations described above, the preparation may also be formulated as a depot preparation. Such long acting formulations may be administered by implantation (for example, subcutaneously or intramuscularly) or by intramuscular injection. Thus, for example, the preparation may be formulated with suitable polymeric or hydrophobic materials (for example, as emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

For administration by inhalation, the compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

5.5.6 Patient (Subject) Evaluation

Patients treated with the compositions disclosed herein may be tested for an anti-tumor immune response. In this regard, peripheral blood from patients may be obtained and assayed for markers of anti-tumor immunity. Using standard laboratory procedures, leukocytes may be obtained from the peripheral blood and assayed for frequency of different immune cell phenotypes, HLA subtype, and function of anti-tumor immune cells.

The majority of effector immune cells in the anti-tumor response is $CD8^+$ T cells and thus is HLA class I restricted. Using immunotherapeutic strategies in other tumor types, expansion of CD8+ cells that recognize HLA class I restricted antigens is found in a majority of patients. However, other cell types are involved in the anti-tumor immune response, including, for example, CD4+ T cells, and macrophages and dendritic cells, which may act as antigen-presenting cells. Populations of T cells (CD4+, CD8+, and Treg cells), macrophages, and antigen presenting cells may be determined using flow cytometry. HLA typing may be performed using routine methods in the art, such as methods described in Boegel et al. Genome Medicine 2012, 4:102 (seq2HLA), or using a TruSight® HLA sequencing panel (Illumina, Inc.). The HLA subtype of CD8+ T cells may be determined by a complement-dependent microcytotoxicity test.

To determine if there is an increase in anti-tumor T cell response, an enzyme linked immunospot assay may be performed to quantify the IFNγ-producing peripheral blood mononuclear cells (PBMC). This technique provides an assay for antigen recognition and immune cell function. In some embodiments, subjects who respond clinically to the vaccine may have an increase in tumor-specific T cells and/or IFNγ-producing PBMCs. In some embodiments, immune cell frequency is evaluated using flow cytometry. In some embodiments, antigen recognition and immune cell function is evaluated using enzyme linked immunospot assays.

In some embodiments, a panel of assays may be performed to characterize the immune response generated to the composition alone or given in combination with standard of care (e.g., maximal surgical resection, radiotherapy, and concomitant and adjuvant chemotherapy with temozolomide for glioblastoma multiforme). In some embodiments, the panel of assays includes one or more of the following tests: whole blood cell count, absolute lymphocyte count, monocyte count, percentage of CD4$^+$CD3$^+$ T cells, percentage of CD8$^+$CD3$^+$ T cells, percentage of CD4$^+$CD25$^+$FoxP3$^+$ regulatory T cells and other phenotyping of PBL surface markers, intracellular cytokine staining to detect proinflammatory cytokines at the protein level, qPCR to detect cytokines at the mRNA level and CFSE dilution to assay T cell proliferation.

In evaluating a subject, a number of other tests may be performed to determine the overall health of the subject. For example, blood samples may be collected from subjects and analyzed for hematology, coagulation times and serum biochemistry. Hematology for CBC may include red blood cell count, platelets, hematocrit, hemoglobin, white blood cell (WBC) count, plus WBC differential to be provided with absolute counts for neutrophils, eosinophils, basophils, lymphocytes, and monocytes. Serum biochemistry may include albumin, alkaline phosphatase, aspartate amino transferase, alanine amino transferase, total bilirubin, BUN, glucose, creatinine, potassium and sodium. Protime (PT) and partial thromboplastin time (PTT) may also be tested. One or more of the following tests may also be conducted: anti-thyroid (anti-microsomal or thyroglobulin) antibody tests, assessment for anti-nuclear antibody, and rheumatoid factor. Urinalysis may be performed to evaluated protein, RBC, and WBC levels in urine. Also, a blood draw to determine histocompatibility leukocyte antigen (HLA) status may be performed.

In some embodiments, radiologic tumor evaluations are performed one or more times throughout a treatment to evaluate tumor size and status. For example, tumor evaluation scans may be performed within 30 days prior to surgery, within 48 hours after surgery (e.g., to evaluate percentage resection), 1 week (maximum 14 days) prior to the first vaccination (e.g., as a baseline evaluation), and approximately every 8 weeks thereafter for a particular duration. MRI or CT imaging may be used. Typically, the same imaging modality used for the baseline assessment is used for each tumor evaluation visit.

5.6 Kits

Kits are also provided for carrying out the prophylactic and therapeutic methods disclosed herein. The kits may optionally further comprise instructions on how to use the various components of the kits.

In certain embodiments, the kit comprises a first container containing the composition disclosed herein, and a second container containing one or more adjuvants. The adjuvant can be any adjuvant disclosed herein, e.g., a saponin, an immunostimulatory nucleic acid, or QS-21 (e.g., QS-21 Stimulon®). In certain embodiments, the kit further comprises a third container containing an additional treatment modality. The kit can further comprise an instruction on the indication, dosage regimen, and route of administration of the composition, adjuvant, and additional treatment modality, e.g., as disclosed in Section 5.5 herein.

Alternatively, the kit can comprise the stress protein(s) and polypeptide(s) of a composition disclosed herein in separate containers. In certain embodiments, the kit comprises a first container containing one or more polypeptides disclosed herein, and a second container containing a purified stress protein capable of binding to the polypeptide.

The first container can contain any number of different polypeptides. For example, in certain embodiments, the first container contains no more than 100 different polypeptides, e.g., 2-50, 2-30, 2-20, 5-20, 5-15, 5-10, or 10-15 different polypeptides. In certain embodiments, each of the different polypeptides comprises the same HSP-binding peptide and a different antigenic peptide. In certain embodiments, the total amount of the polypeptide(s) in the first container is a suitable amount for a unit dosage. In certain embodiments, the total amount of the polypeptide(s) in the first container is about 0.1 to 20 nmol (e.g., 3, 4, 5, or 6 nmol).

The second container can contain any stress protein disclosed herein. In certain embodiments, the stress protein is selected from the group consisting of Hsc70, Hsp70, Hsp90, Hsp110, Grp170, Gp96, or Calreticulin, and a mutant or fusion protein thereof. In certain embodiments, the stress protein is Hsc70 (e.g., human Hsc70). In certain embodiments, the stress protein is a recombinant protein. In certain embodiments, the total amount of the stress protein(s) in the second container is about 10 μg to 600 μg (e.g., 250 μg to 290 μg). In certain embodiments, the total amount of the stress protein(s) in the second container is about 50 μg, 100 μg, 200 μg, 300 μg, 400 μg, or 500 μg. In certain embodiments, the amount of the stress protein in the pharmaceutical composition is about 300 μg. In certain embodiments, the total molar amount of the stress protein(s) in the second container is calculated based on the total molar amount of the polypeptide(s) in the first container, such that the molar ratio of the polypeptide(s) to the stress protein(s) is about 0.5:1 to 5:1 (e.g., about 1:1 to 2:1, e.g., about 1:1, 1.25:1, or 1.5:1). In certain embodiments, the total amount of the stress protein(s) in the second container is an amount for multiple administrations (e.g., less than or equal to 1 mg, 3 mg, 10 mg, 30 mg, or 100 mg).

In certain embodiments, the kit further comprises an instruction for preparing a composition from the polypeptide(s) in the first container and the stress protein(s)

in the second container (e.g., an instruction for the complexing reaction as disclosed in Section 5.4.2 herein).

In certain embodiments, the kit further comprises a third container containing one or more adjuvants. The adjuvant can be any adjuvant disclosed herein, e.g., a saponin, an immunostimulatory nucleic acid, or QS-21 (e.g., QS-21 Stimulon®). In certain embodiments, the kit further comprises a fourth container containing an additional treatment modality. The kit can further comprise an instruction on the indication, dosage regimen, and route of administration of the composition prepared from the polypeptide(s) and stress protein(s), the adjuvant, and the additional treatment modality, e.g., as disclosed in Section 5.5 herein.

In certain embodiments, the composition, polypeptide(s), stress protein(s), adjuvant(s), and additional treatment modality in the containers are present in pre-determined amounts effective to treat cancers or infections. If desired, the compositions can be presented in a pack or dispenser device which may contain one or more unit dosage forms of the compositions. The pack may, for example, comprise metal or plastic foil, such as a blister pack. The pack or dispenser device may be accompanied by instructions for administration.

5.7 HPV Peptides

In another aspect, the instant disclosure provides a polypeptide comprising an HSP-binding peptide and an amino acid sequence from a human papillomavirus (HPV) (e.g., HPV16 or HPV18). Such amino acid sequence is also referred to as an HPV peptide herein.

The HPV peptide can comprise any amino acid sequence as disclosed in Table 3. In certain embodiments, the amino acid sequence from HPV comprises the amino acid sequence of SEQ ID NO: 38, 39, 40, 41, 42, 43, 44, 45, 46, 47, 48, 49, 50, 51, 52, or 53.

TABLE 3

Amino acid sequences of antigenic HPV peptides

| Peptide Name | Amino Acid Sequence | SEQ ID NO: |
|---|---|---|
| PEP087 | MHQKRTAMFQDPQERPRKLPQLCTELQTTI | 38 |
| PEP088 | PRKLPQLCTELQTTIHDIILECVYCKQQLL | 39 |
| PEP089 | HDIILECVYCKQQLLRREVYDFAFRDLCIV | 40 |

TABLE 3-continued

Amino acid sequences of antigenic HPV peptides

| Peptide Name | Amino Acid Sequence | SEQ ID NO: |
|---|---|---|
| PEP090 | RREVYDFAFRDLCIVYRDGNPYAVCDKCLKF | 41 |
| PEP091 | RDGNPYAVCDKCLKFYSKISEYRHYCYSLY | 42 |
| PEP092 | YSKISEYRHYCYSLYGTTLEQQYNKPLCDL | 43 |
| PEP093 | GTTLEQQYNKPLCDLLIRCINCQKPLCP | 44 |
| PEP094 | DLLIRCINCQKPLCPEEKQRHLDKKQRFH | 45 |
| PEP095 | PEEKQRHLDKKQRFHNIRGRWTG | 46 |
| PEP096 | DKKQRFHNIRGRWTGRCMSCCRSSRTRRETQL | 47 |
| PEP097 | MHGDTPTLHEYMLDLQPETTDLYCYEQLN | 48 |
| PEP098 | LQPETTDLYCYEQLNDSSEEEDEIDGP | 49 |
| PEP099 | QLNDSSEEEDEIDGPAGQAEPDRAHYNIV | 50 |
| PEP100 | PAGQAEPDRAHYNIVTFCCKCDSTLRLCV | 51 |
| PEP101 | VTFCCKCDSTLRLCVQSTHVDIRTLEDLL | 52 |
| PEP102 | VQSTHVDIRTLEDLLMGTLGIVCPICSQKP | 53 |

The HSP-binding peptide can be any HSP-binding peptide disclosed in Section 5.2, or any HSP-binding peptide known in the art (see, e.g., US20160331821A1 and U.S. Pat. No. 7,309,491B2, each of which is incorporated by reference herein in its entirety). In certain embodiments, the HSP-binding peptide comprises the amino acid sequence of SEQ ID NO: 1, 2, 3, 4, or 232. In certain embodiments, the HSP-binding peptide comprises the amino acid sequence of SEQ ID NO: 5, 6, 7, 8, 9, 10, 11, 12, 98, 99, 100, 101, 102, 103, 104, 105, 106, 107, 108, 109, 110, 111, 112, 113, 204, 205, 207, 208, 209, 210, 211, 212, 213, 214, or 215. In certain embodiments, the HSP-binding peptide comprises the amino acid sequence of SEQ ID NO: 6.

The HPV peptide can be linked to the HSP-binding peptide via any linker disclosed herein (e.g., in Section 5.3). In certain embodiments, the HPV peptide is linked to the HSP-binding peptide via a peptide linker. In certain embodiments, the peptide linker comprises the amino acid sequence of FR or FFRK (SEQ ID NO: 13).

In certain embodiments, the HPV peptide comprises the amino acid sequence of SEQ ID NO: 54, 55, 56, 57, 58, 59, 60, 61, 62, 63, 64, 65, 66, 67, 68, or 69.

TABLE 4

Amino acid sequences of HSP-binding antigenic HPV peptides

| Peptide Name | Description | Amino Acid Sequence | SEQ ID NO: |
|---|---|---|---|
| PEP071 | HPV16 E6 1-30 linked to PEP006 | MHQKRTAMFQDPQERPRKLPQLCT ELQTTIFFRKNWLRLTW | 54 |
| PEP072 | HPV16 E6 16-45 linked to PEP006 | PRKLPQLCTELQTTIHDIILECVYCK QQLLFFRKNWLRLTW | 55 |
| PEP073 | HPV16 E6 31-60 linked to PEP006 | HDIILECVYCKQQLLRREVYDFAFR DLCIVFFRKNWLRLTW | 56 |
| PEP074 | HPV16 E6 46-76 linked to PEP006 | RREVYDFAFRDLCIVYRDGNPYAVC DKCLKFFFRKNWLRLTW | 57 |

TABLE 4-continued

Amino acid sequences of HSP-binding antigenic HPV peptides

| Peptide Name | Description | Amino Acid Sequence | SEQ ID NO: |
|---|---|---|---|
| PEP075 | HPV16 E6 62-91 linked to PEP006 | RDGNPYAVCDKCLKFYSKISEYRHY CYSLYFFRKNWLRLTW | 58 |
| PEP076 | HPV16 E6 77-106 linked to PEP006 | YSKISEYRHYCYSLYGTTLEQQYNK PLCDLFFRKNWLRLTW | 59 |
| PEP077 | HPV16 E6 92-119 linked to PEP006 | GTTLEQQYNKPLCDLLIRCINCQKPL CPFFRKNWLRLTW | 60 |
| PEP078 | HPV16 E6 105-133 linked to PEP006 | DLLIRCINCQKPLCPEEKQRHLDKKQ RFHFFRKNWLRLTW | 61 |
| PEP079 | HPV16 E6 119-141 linked to PEP006 | PEEKQRHLDKKQRFHNIRGRWTGFF RKNWLRLTW | 62 |
| PEP080 | HPV16 E6 127-158 linked to PEP006 | DKKQRFHNIRGRWTGRCMSCCRSS RTRRETQLFFRKNWLRLTW | 63 |
| PEP081 | HPV16 E7 1-29 linked to PEP006 | MHGDTPTLHEYMLDLQPETTDLYC YEQLNFFRKNWLRLTW | 64 |
| PEP082 | HPV16 E7 15-41 linked to PEP006 | LQPETTDLYCYEQLNDSSEEEDEIDG PFFRKNWLRLTW | 65 |
| PEP083 | HPV16 E7 27-55 linked to PEP006 | QLNDSSEEEDEIDGPAGQAEPDRAH YNIVFFRKNWLRLTW | 66 |
| PEP084 | HPV16 E7 41-69 linked to PEP006 | PAGQAEPDRAHYNIVTFCCKCDSTL RLCVFFRKNWLRLTW | 67 |
| PEP085 | HPV16 E7 55-83 linked to PEP006 | VTFCCKCDSTLRLCVQSTHVDIRTLE DLLFFRKNWLRLTW | 68 |
| PEP086 | HPV16 E7 69-98 linked to PEP006 | VQSTHVDIRTLEDLLMGTLGIVCPIC SQKPFFRKNWLRLTW | 69 |

In another aspect, the instant disclosure provides a composition (e.g., pharmaceutical composition) comprising a plurality of different polypeptides, wherein each polypeptide comprises an HSP-binding peptide and an HPV peptide. In certain embodiments, the amino acid sequence of at least one HPV peptide is selected from the group consisting of SEQ ID NOs: 38-53. In certain embodiments, the amino acid sequence of each HPV peptide is selected from the group consisting of SEQ ID NOs: 38-53. In certain embodiments, the composition comprises at least 2, 3, 4, 5, 6, 7, 8, 9, 10, 11, 12, 13, 14, 15, or 16 different HPV peptides.

In certain embodiments, the amino acid sequence of at least one polypeptide is selected from the group consisting of SEQ ID NOs: 54-69. In certain embodiments, the amino acid sequence of each polypeptide is selected from the group consisting of SEQ ID NOs: 54-69. In certain embodiments, the composition comprises at least 2, 3, 4, 5, 6, 7, 8, 9, 10, 11, 12, 13, 14, 15, or 16 different polypeptides.

In certain embodiments, the composition further comprises a purified stress protein. Any stress protein disclosed herein (e.g., in Section 5.4) can be used. For example, in certain embodiments, the stress protein is selected from the group consisting of Hsc70, Hsp70, Hsp90, Hsp110, Grp170, Gp96, Calreticulin, and a mutant or fusion protein thereof. In certain embodiments, the stress protein is Hsc70 (e.g., human Hsc70).

The ratio of polypeptide to stress protein can be any ratio disclosed herein, e.g., about 0.5:1 to 5:1. In certain embodiments, the ratio of polypeptide to stress protein is about 1:1 to 2:1. In certain embodiments, the ratio of polypeptide to stress protein is about 1:1, 1.25:1, or 1.5:1. Also, the amounts of the polypeptide(s) and of the stress protein(s) can be any amounts disclosed in Section 5.4 herein. In certain embodiments, the composition is in a unit dosage form.

In another aspect, the instant disclosure provides a kit comprising the composition disclosed herein either in a single container or in separate containers, optionally further comprising containers containing one or more adjuvants and additional treatment modalities, as disclosed in Section 5.6 herein.

In another aspect, the instant disclosure provides a method of inducing a cellular immune response to an HPV peptide in a subject, the method comprising administering to the subject an effective amount of a composition as disclosed in this section. In another aspect, the instant disclosure provides a method of treating an HPV-associated disease in a subject, the method comprising administering to the subject an effective amount of a composition as disclosed this section. In certain embodiments, the HPV-associated disease is a cancer (e.g., cervical cancer). In certain embodiments, the HPV is HPV16 or HPV18. Any dosage regimen as disclosed in Section 5.5.4 herein and any route of administration as disclosed in Section 5.5.5 herein can be used. The method can further comprise an additional treatment modality as disclosed in Section 5.5.3 herein, and can further comprise a patient evaluation step as disclosed in Section 5.5.6 herein.

6. EXAMPLES

The examples in this Section (i.e., Section 6) are offered by way of illustration, and not by way of limitation.

6.1 Example 1: Identification of Peptides that Bind to Hsc70 with High Affinity This example describes the design of heat shock protein (HSP)-binding peptide with improved binding to HSPs as compared to a heat shock protein-binding peptide having the amino acid sequence of NLLRLTG (SEQ ID NO: 70) (see U.S. patent application published as US20160331821A1, incorporated herein by reference in its entirety).

6.1.1 Binding of Peptides to Hsc70

To identify peptides that bind to human Hsc70 with high affinity, variants of the NLLRLTG (SEQ ID NO: 70) sequence were designed, and a linker having the amino acid sequence of FFRK (SEQ ID NO: 13) was added to the N-terminus. The amino acid sequences of the peptides synthesized and tested are provided in Table 5.

TABLE 5

Amino acid sequences of HSP-binding peptides

| Peptide Name | Amino Acid Sequence | SEQ ID NO: |
|---|---|---|
| PEP001 | FFRKNLLRLTG | 71 |
| PEP006 | FFRKNWLRLTW | 18 |
| PEP012 | FFRKNWLKLTW | 19 |
| PEP055 | FFRKNWLKLKW | 72 |
| PEP056 | FFRKNWLKLKW amide* | 73 |
| PEP057 | FFRKNWLKLRW | 74 |
| PEP058 | FFRKNWLKLWK | 75 |

*amidation of C-terminal carboxyl group

The peptides were synthesized using standard Fmoc solid-phase chemical synthesis with pre-loaded polystyrene wang (PS-Wang) resin in a Symphony-X automatic synthesizer (Gyros Protein Technologies Inc). Fmoc protected L-amino acids were applied with standard HCTU/NMM activation chemistry. With respect to resin substitution, 5-fold excess of amino acid, 5-fold excess of activating reagent (HCTU) and 10-fold excess of N-methyl morpholine was used for coupling the amino acid to make the peptide bond. The reaction was performed for 6 min with double coupling cycle for any incomplete coupling throughout the synthesis. These steps were repeated until the desired sequence was obtained. At the end of the synthesis, resin was washed with dichloromethane (DCM) and dried. Upon completion of peptide assembly, the resin was transferred to another cleavage vessel for cleaving the peptide from the resin. A cleavage cocktail reagent Trifluoroacetic acid: Dithiothreitol water: Triisopropylsilane (88:5:5:2 v/w/v/v) was mixed with the resin and stirred for 4 hours at 25° C. The crude peptides were isolated from the resin by filtration and evaporated with $N_2$ gas followed by precipitation with chilled diethyl ether and stored at −20° C. for 12 hours. The precipitated peptides were centrifuged and washed 2× with ether, dried, dissolved in the choice of solvent, and lyophilized to produce a crude dry powder. The crude peptides were purified by prep-HPLC with a C18 column (Ultimate 3000, Thermo Scientific) using a water (0.1% TFA)-acetonitrile (0.1% TFA) gradient. Peptide purity was tested using an analytical C18-column. Further characterization was confirmed by 6550 Q-TOF (Agilent Technologies) mass spectrometry.

Individual peptides were solubilized in 100% DMSO at 10 mg/ml followed by a second dilution step to 320 μM in 75% DMSO. To form a peptide-Hsc70 complex, Hsc70 was mixed at a concentration of 7 μM (0.5 mg/ml) with the appropriate concentration of peptide in 1×PBS with a final volume of 25 μl. The mixed samples were then incubated at 37° C. for 1 hour and cooled down on ice for 10 min. To evaluate the quantity of the complex in the solution, 20 μl (10 μg) of the sample was loaded on a size exclusion chromatography (SEC) column TSKgel SuperSW3000 (Tosoh Bioscience) at a flow rate of 0.2 ml/min with 1×PBS as a running buffer. The data was collected by measuring the absorbance at both 280 and 214 nm.

In a separate experiment, further variants of the peptide NLLRLTG (SEQ ID NO: 70) were generated and the ability of these peptides to form a peptide-Hsc70 complex was analyzed. Peptides were again synthesized using standard Fmoc solid-phase chemical synthesis, as described above. Individual peptides were solubilized in pH adjusted water at a concentration of 250 μM, and spiked with polysorbate 20 to a final concentration of 0.1%. To form a peptide-Hsc70 complex, Hsc70 (1 mg/ml, 0.1% polysorbate) was mixed with peptide at peptide:Hsc70 molar ratios of, 0.25:1, 0.5:1, 1:1, 2:1, and 4:1, for 60 minutes at 30° C. Following incubation, samples were cooled for 5 minutes at room temperature and transferred to HPLC vials for analysis. To evaluate the quantity of the complex in the solution, 20 μl (10 μg) of the sample was loaded on a size exclusion chromatography column TSKgel SuperSW3000 (Tosoh Bioscience) at a flow rate of 0.2 ml/min with 1×PBS as a running buffer. The data was collected by measuring the absorbance at 214 nm.

The percent of Hsc70 bound to peptide was calculated by SEC. As shown in the SEC chromatogram depicted in FIG. 1, recombinant human heat shock cognate 71 kDa protein (Hsc70) appeared as monomer (M), dimer (D), trimer (T), and higher order high molecular weight (HMW) oligomeric species when subjected to SEC chromatography. Resolution and evaluation of the extent to which peptide-Hsc70 complex was formed with a given peptide or peptide mixture was complicated by the close elution of a complex of Hsc70 monomer with peptide (Msh). The peaks corresponding to monomer and complex overlap and were not fully resolved by conventional SEC media. In order to more accurately calculate the extent of complex formation, the following data analytical method was used. A central feature of this method was based on the observation that trimeric and dimeric forms of Hsc70 were observed to be recruited to the formation of monomeric peptide complexes. Peak area integrations of these protein species were well resolved from the complex and monomer. Further, the extent to which complex was formed appeared to be inversely proportional to the extent to which trimer and dimer were recruited to complex formation. Because of this observation, changes in trimer and dimer reflected the extent to which monomer was recruited to the formation of complex. Thus, the progression of changes in the level of trimer and dimer was used to calculate expected changes in the peak areas of overlapping complex and monomer species, and these calculated peak areas were used to calculate net formation of complex. This data analysis method is described below.

Terms used for various chromatographic fractions include: High Molecular Weight (HMW), Trimer and other mid-order oligomer (T), Dimer (D), Complex (C), Monomer shoulder (Msh), and Monomer (M) (see FIG. 1). Peak areas of the various fractions were extracted from SEC data and the percentage of peptide-Hsc70 complex formation was calculated using the following set of equations:

$$\% \text{ Complex} = (\text{AREA}_{complex}/\text{AREA}_{Total}) \times 100$$

$$\text{AREA}_{complex} = \text{AREA}_{Total} - (\text{Area}_{T+D} + \text{Area}_{Mshx} + \text{Area}_{Mx})$$

$$\text{AREA}_{Total} = \text{AREA}_{T+D,C,Msh,M} + (\text{AREA}_{HDw-x} - \text{AREA}_{HDW-0})$$

$$\text{AREA}_{Mshx} = \text{AREA}_{Msh0} \times (\text{AREA}_{(T+D)x})/(\text{AREA}_{(T+D)0})$$

$$\text{AREA}_{Mx} = \text{AREA}_{M0} \times (\text{AREA}_{(T+D)x})/(\text{AREA}_{(T+D)0})$$

$\text{AREA}_{Total}$ is the sum of total integrated peak areas from trimer/oligomer region through the monomer peak and excludes the initial HMW peak area but includes the excess increase of the HMW peak area that was observed when peptide was added. The HMW peak was excluded from the complexation calculation on the basis that it was aggregated protein that was not functional for complexation. This correction took into account $\text{Area}_{Total}$ factors in the minor increase in HMW area, adding it back to base total area used to calculate area of complex. Including this adjustment resulted in a more stable $\text{Area}_{Total}$ across the range of peptide concentrations used to form complexes.

Figure 1:
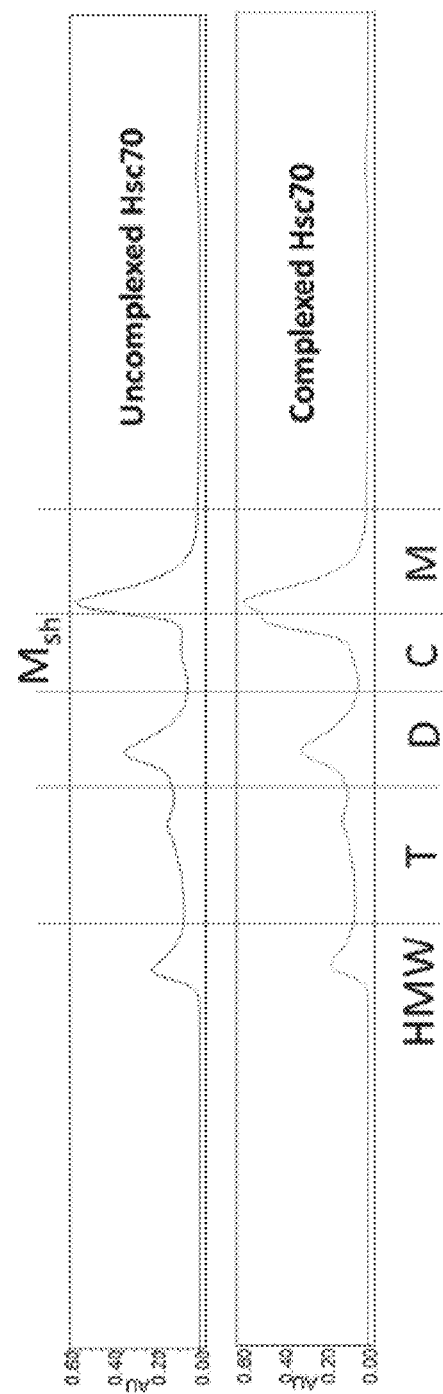

The foregoing method was applied to the SEC chromatogram for each complexation reaction by applying vertical lines to the chromatogram to produce HMW, T, C, D, and M segments (as shown in FIG. 1), calculating the area under the curve for of each of the indicated HMW, T, C, D, and M segments, and inputting the values into the equations described above. The results of this analysis are show in Table 6.

TABLE 6

Percent complexation of peptides with Hsc70

| Peptide Name | SEQ ID NO: | Sequence | 0.25:1 | 0.5:1 | 1:1 | 2:1 | 4:1 |
|---|---|---|---|---|---|---|---|
| PEP001 | 71 | FFRKNLLRLTG | 23.4 | 44.7 | 68.1 | 82.5 | 90.1 |
| PEP002 | 165 | FFRKNRLLLTG | 19.2 | 32.0 | 48.7 | 64.8 | 78.8 |
| PEP003 | 166 | FFRKNWLLLTW | 26.8 | 45.6 | 67.2 | 81.3 | 87.6 |
| PEP004 | 167 | FFRKNLLRWTG | 15.4 | 29.0 | 46.8 | 62.5 | 75.3 |
| PEP005 | 168 | FFRKNRLWLTG | 16.0 | 32.7 | 54.8 | 67.6 | 77.6 |
| PEP006 | 18 | FFRKNWLRLTW | 25.4 | 53.4 | 81.5 | 88.3 | 91.8 |
| PEP027 | 21 | FFRKNFLRLTF | 19.1 | 49.0 | 77.0 | 85.6 | 90.0 |
| PEP008 | 169 | FFRKFWLRLTW | 24.4 | 38.3 | 61.8 | 79.1 | 81.6 |
| PEP009 | 170 | FFRKNWLRLLW | 32.8 | 63.5 | 81.0 | 85.3 | 89.0 |
| PEP010 | 171 | FFRKNWLRLFW | 19.1 | 42.2 | 64.9 | 79.3 | 86.5 |
| PEP011 | 172 | FFRKNWLRLKW | 31.2 | 58.2 | 81.6 | 87.8 | 90.4 |
| PEP012 | 19 | FFRKNWLKLTW | 29.9 | 58.2 | 79.2 | 86.2 | 89.5 |
| PEP013 | 173 | FFRKNWIRITW | 25.6 | 48.3 | 69.6 | 81.9 | 87.7 |
| PEP014 | 174 | FFRKQWLRLTW | 29.3 | 54.4 | 80.9 | 88.1 | 90.3 |

TABLE 6-continued

Percent complexation of peptides with Hsc70

| Peptide Name | SEQ ID NO: | Sequence | 0.25:1 | 0.5:1 | 1:1 | 2:1 | 4:1 |
|---|---|---|---|---|---|---|---|
| PEP028 | 22 | FRNWLRLTW | 24.0 | 46.4 | 75.6 | 84.1 | 87.5 |
| PEP055 | 72 | FFRKNWLKLKW | 24.1 | 52.2 | 75.9 | 83.7 | 86.3 |
| PEP057 | 74 | FFRKNWLKLRW | 24.9 | 50.0 | 72.2 | 82.8 | 88.3 |
| PEP058 | 75 | FFRKNWLKLWK | 22.7 | 43.5 | 66.5 | 78.8 | 83.9 |
| PEP155 | 164 | FFRKNLLRLTW | 22.5 | 48.1 | 75.6 | 82.9 | 86.6 |

PEP006 was selected for further characterization.

6.1.2 Complexation of Hsc70 with PEP006

This example demonstrates the ability of PEP006 to bind to Hsc70 at a range of molar ratios from 0.25:1 to 3:1, as determined by size exclusion chromatography.

Briefly, PEP006 peptide was reconstituted in water for injection (WFI) to a concentration of 645 µM. Recombinant human Hsc70 (rhHsc70) was diluted at a concentration of 1.66 mg/mL. Both solutions were pre-warmed in a 37° C. incubator for 10 minutes, and were combined and incubated at 37° C. for 60 minutes. The final concentration of rhHsc70 was 1 mg/mL (about 14.1 µM), and the molar ratio of PEP006 to rhHsc70 was 0.25:1, 0.5:1, 1:1, 1.5:1, 2:1, 2.5:1, and 3:1. A negative control containing only rhHsc70 at 1 mg/mL was also prepared.

A quantity of 10 µg of each sample was injected neat in triplicate for resolution by size exclusion HPLC (Alliance HPLC, Waters Model #2695 Separations Module; Dual Wavelength UV Detector, Waters Model 2487) using a chromatography column TSKgel SuperSW3000 (Tosoh Bioscience, Catalog #18675). The column temperature was controlled at 25° C.±5° C., and the autosampler temperature was controlled at 5° C.±3° C. The mobile phase was composed of 10 mM sodium phosphate with 300 mM sodium chloride, pH 7.2, and was delivered at a flow rate of 0.2 mL/min for 30 minutes. UV absorbance of PEP006 peptide and rhHsc70 protein was measured at the wavelengths of 214 nm and 280 nm. The absorbance data was processed by Waters Empower (V2) software.

Figure 2:
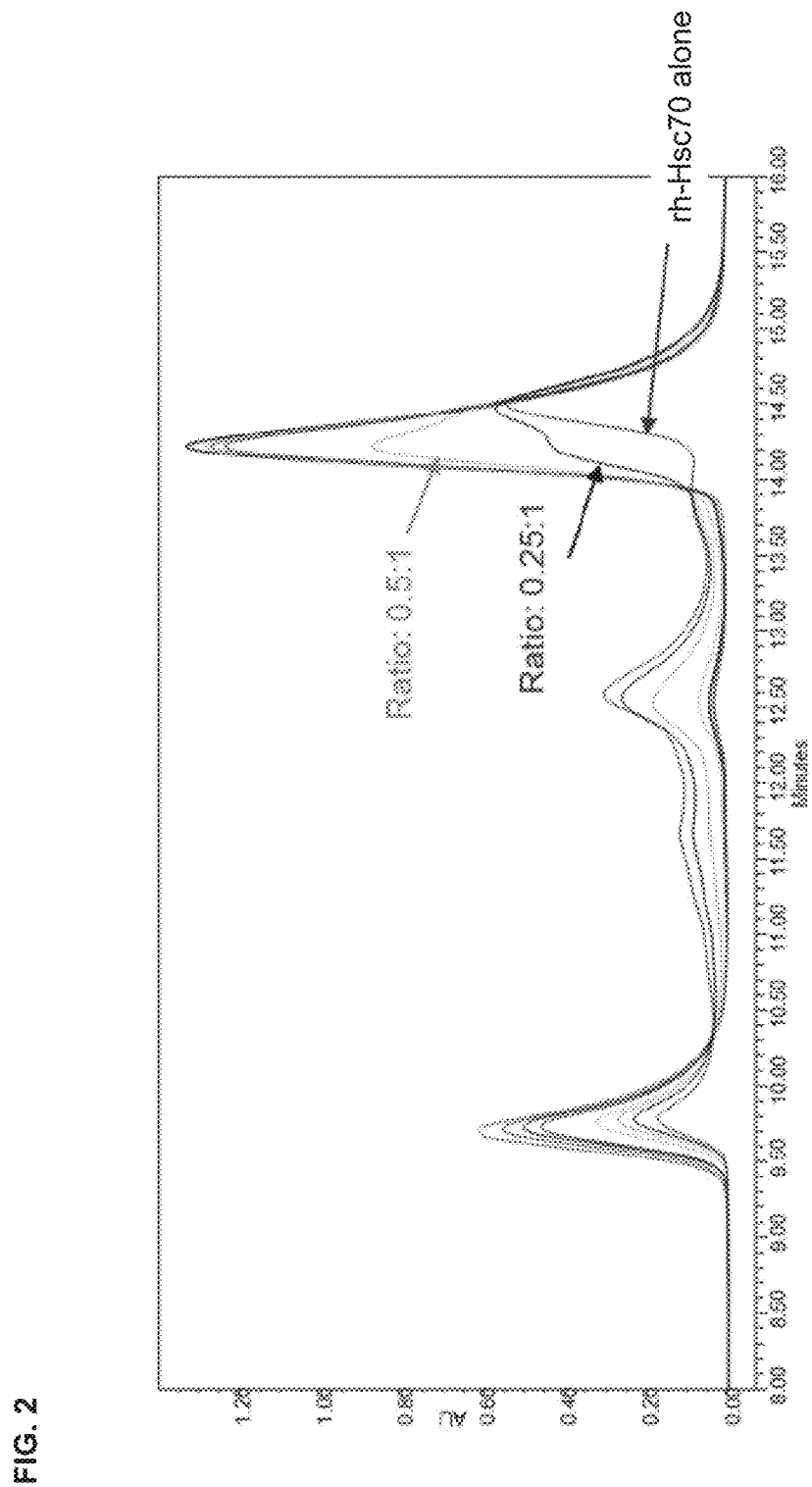

FIG. 2 shows a chromatogram of the PEP006-Hsc70 complexation products, wherein the column retention time became shorter when rhHsc70 bound to PEP006.

6.1.3 Complexation of Hsc70 with Polypeptides Comprising PEP006

This example describes characterization of the binding of Hsc70 to the polypeptide LGVVRPRALHRELDLVDD-SPTPGSPGSFFRKNWLRLTW (SEQ ID NO: 77), which comprises PEP006 and a peptide observed from a patient's tumor (LGVVRPRALHRELDLVDDSPTPGSPGS (SEQ ID NO: 76)). The molar ratios of polypeptide to Hsc70 tested in this example were 0.125:1, 0.25:1, 0.5:1, 1:1, 1.5:1, 2:1, 2.5:1, 3:1, 3.5:1, and 4:1.

Figure 3A:
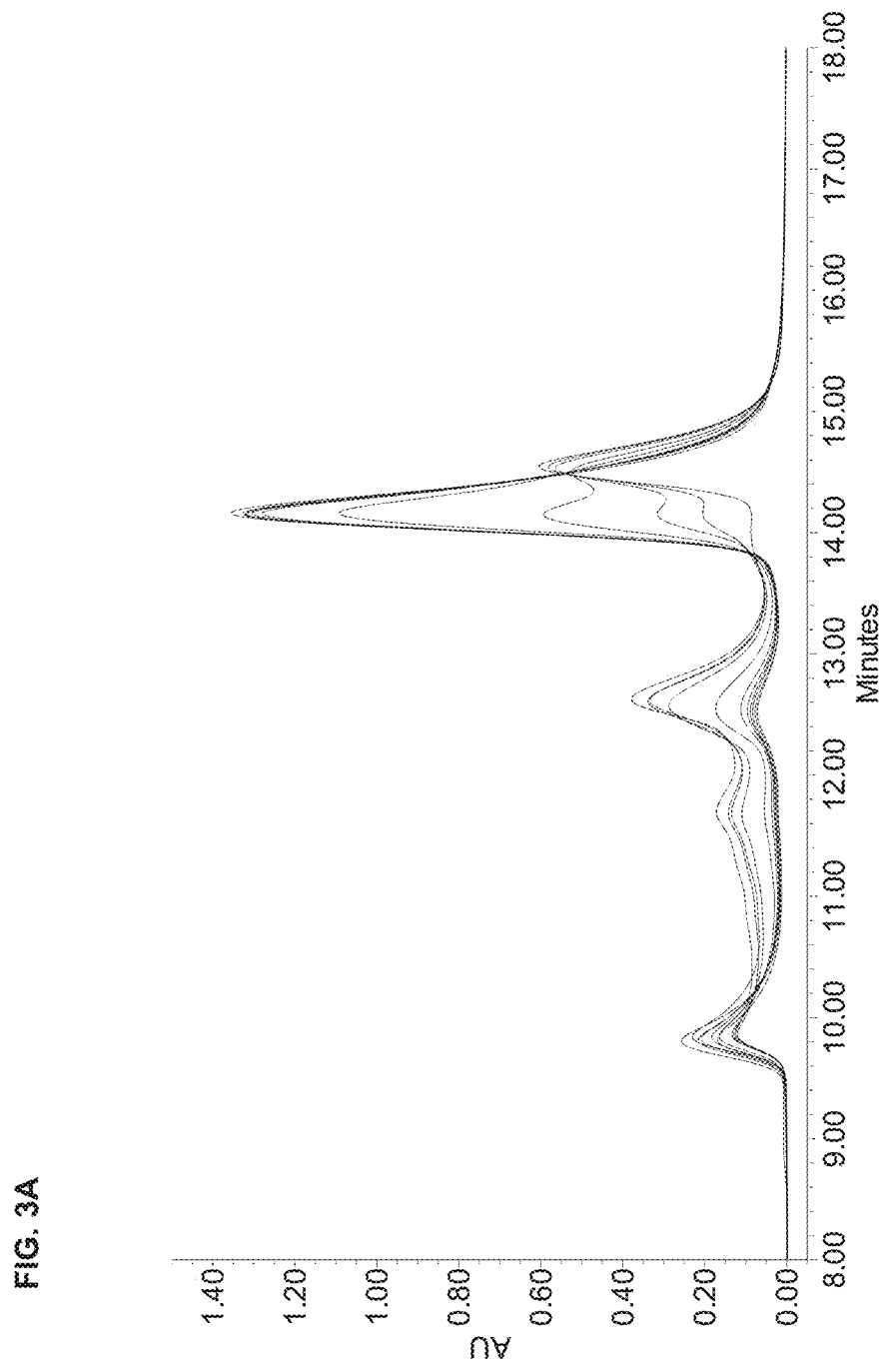
Figure 3B:
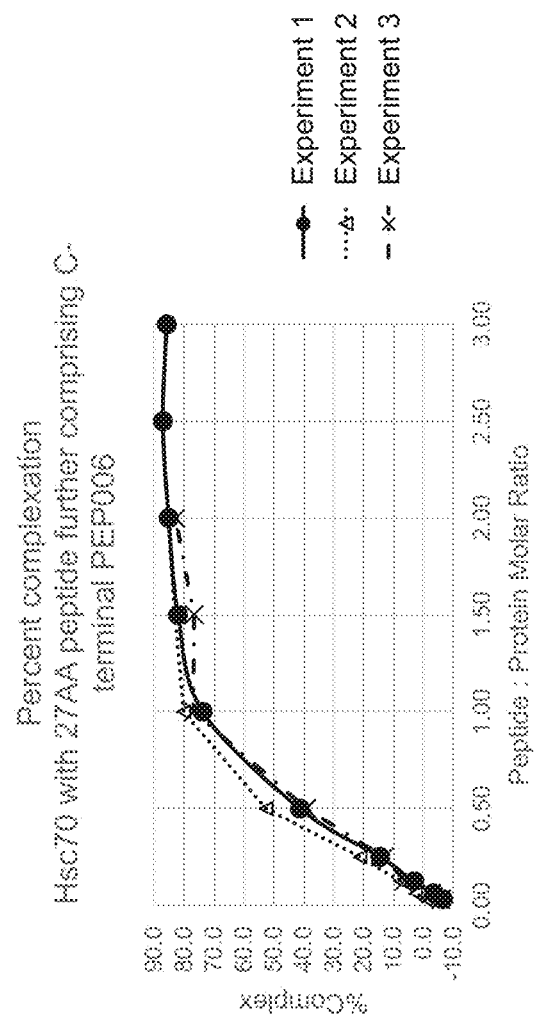

FIG. 3A shows a chromatogram of the polypeptide-Hsc70 complexation products, wherein the column retention time became shorter when rhHsc70 bound to the polypeptide. FIG. 3B is a graph showing percent complexation of a polypeptide comprising PEP006 with HSC70 over a range of polypeptide:Hsc70 molar ratios from 0.125:1 to 4:1, as calculated from size exclusion chromatography traces similar to those in FIG. 3A, using the methods described Example 6.1.1. Three independent experiments are shown.

To further characterize binding of Hsc70 to polypeptides comprising C-terminal PEP006 or PEP001, a range of polypeptides was generated with C-terminal PEP001, PEP006, and in some cases, the same polypeptide without a C-terminal HSC70 binding peptide. The peptides used are shown in Table 7 below. Polypeptides were synthesized, complexation was performed, and SEC data was analyzed according to the methods described in Example 6.1.1, above.

TABLE 7

Polypeptides

| Peptide Name | Sequence | SEQ ID NO: |
|---|---|---|
| PEP165 | AKFVAAWTLKAAA | 184 |
| PEP166 | AKFVAAWTLKAAAFFRKNLLRLTG | 185 |
| PEP167 | AKFVAAWTLKAAAFFRKNWLRLTW | 186 |
| PEP168 | PLLPFYPPDEALEIGLELNSSALPPTE | 187 |
| PEP169 | PLLPFYPPDEALEIGLELNSSALPPTEF FRKNLLRLTG | 188 |
| PEP170 | PLLPFYPPDEALEIGLELNSSALPPTEF FRKNWLRLTW | 189 |
| PEP171 | EHIHRAGGLFV ADAIQVGFGRIGKHFW | 190 |
| PEP172 | EHIHRAGGLFV ADAIQVGFGRIGKHF WFFRKNLLRLTG | 191 |
| PEP173 | EHIHRAGGLFV ADAIQVGFGRIGKHF WFFRKNWLRLTW | 192 |
| PEP174 | DKPLRRNNSYTSYIMAICGMPLDSFRA | 193 |
| PEP175 | DKPLRRNNSYTSYIMAICGMPLDSFR AFFRKNLLRLTG | 194 |
| PEP176 | DKPLRRNNSYTSYIMAICGMPLDSFR AFFRKNWLRLTW | 195 |
| PEP177 | EVIQTSKYYMRDVIAIESAWLLELAPH | 196 |
| PEP178 | EVIQTSKYYMRDVIAIESAWLLELAP H FFRKNLLRLTG | 197 |
| PEP179 | EVIQTSKYYMRDVIAIESAWLLELAP HFFRKNWLRLTW | 198 |

TABLE 7-continued

Polypeptides

| Peptide Name | Sequence | SEQ ID NO: |
|---|---|---|
| PEP180 | VILPQAPSGPSYATYLQPAQAQMLTPP | 199 |
| PEP181 | VILPQAPSGPSYATYLQPAQAQMLTP PFFRKNLLRLTG | 200 |
| PEP182 | VILPQAPSGPSYATYLQPAQAQMLTP PFFRKNWLRLTW | 201 |

Figure 4A:
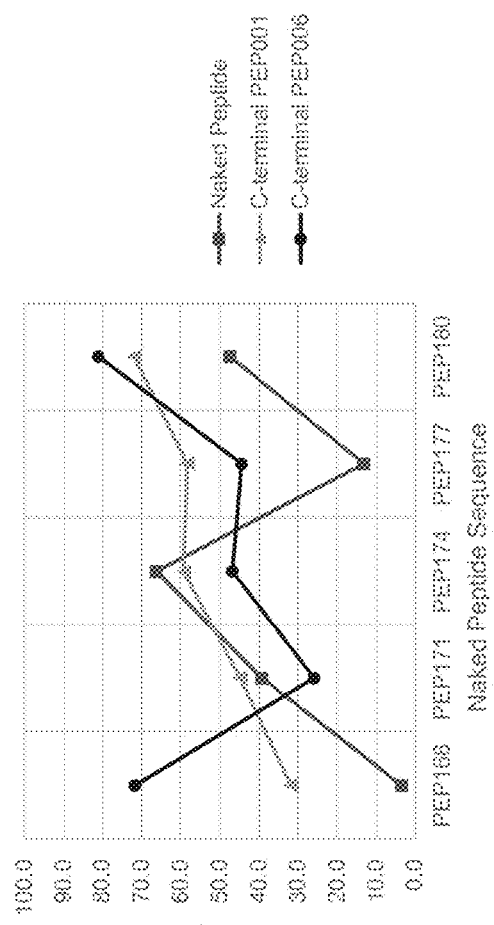
Figure 4B:
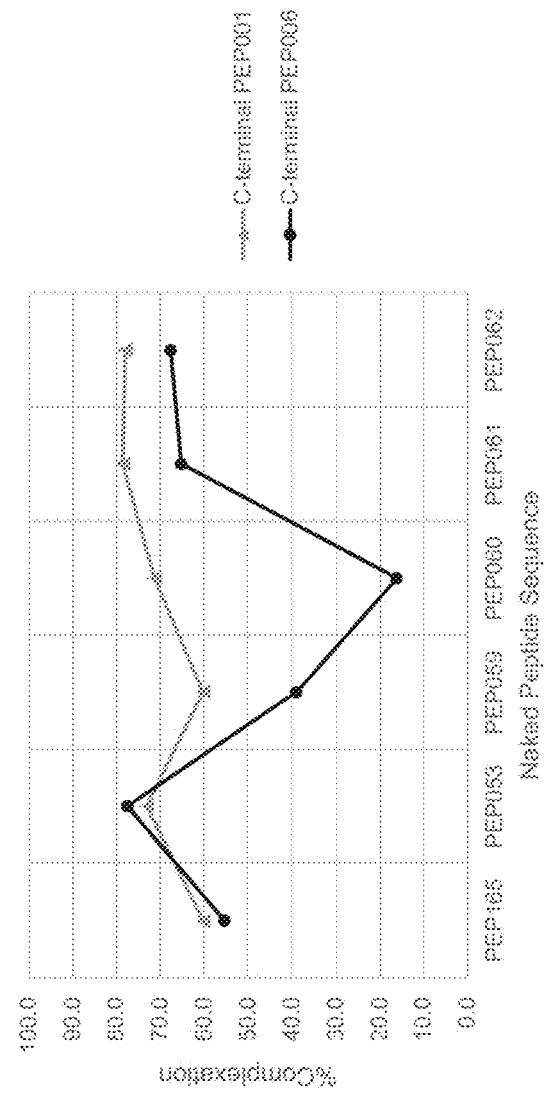

FIG. 4A is a graph showing percent complexation for five different peptides, where each of the five different peptides comprised, C-terminal PEP001, C-terminal PEP006, or no C-terminal HSC70 binding peptide. FIG. 4B is a graph showing percent complexation for six different peptides, where each of the six different peptides comprised either, C-terminal PEP001, or C-terminal PEP006.

6.2 Example 2: Enhancement of Cellular Immunity by HSP-Binding Peptides

This example demonstrates immunogenicity and tumor-suppressing activity of polypeptides comprising HPV E6-E7 peptides and PEP001 or PEP006 in two animal models.

6.2.1 Increase of Antigenic Peptide Immunogenicity by HSP-Binding Peptides

In this example, immunogenicity of a pool of four polypeptides, each comprising an immunogenic HPV E6 or E7 peptide linked to PEP001 or PEP006, or not linked to an HSP-binding peptide, was analyzed in an immunogenicity animal model.

Briefly, four HPV E6 or E7 peptides either alone or linked to PEP001 or PEP006, having the amino acid sequences provided in Table 8, were chemically synthesized and dissolved in 100% DMSO at concentrations ranging from 25 to 100 mg/ml. These HPV E6 and E7 peptides were known to be immunogenic in C57BL/6 mice (see Bartkowiak et al. (2015) Proc Natl Acad Sci USA. 112(38); and Manuri et al. (2007) Vaccine 25(17):3302-10, each of which is incorporated by reference herein in its entirety). The known epitope sequence of PEP059 and PEP060 was RAHYNIVTF (SEQ ID NO: 78), and the known epitope sequence of PEP061 and PEP062 was VYDFAFRDL (SEQ ID NO: 79).

TABLE 8

Amino acid sequences of HPV peptides*

| Peptide pool | Peptide Name | Description | Amino Acid Sequence | SEQ ID NO: |
|---|---|---|---|---|
| Naked peptides | PEP059 | HPV16 E7 44-62 Q19D | QAEPDRAHYNIVTFCCKCD | 80 |
|  | PEP060 | HPV16 E7 49-57 R9F | RAHYNIVTF | 81 |
|  | PEP061 | HPV16 E6 43-57 Q15L | QLLRREVYDFAFRDL | 82 |
|  | PEP062 | HPV16 E6 49-58 V10C | VYDFAFRDLC | 83 |
| PEP001-linked peptides | PEP067 | PEP059 linked to C-terminal PEP001 | QAEPDRAHYNIVTFCCKCDF FRKNLLRLTG | 84 |
|  | PEP068 | PEP060 linked to C-terminal PEP001 | RAHYNIVTFFFRKNLLRLTG | 85 |
|  | PEP069 | PEP061 linked to C-terminal PEP001 | QLLRREVYDFAFRDLFFRKN LLRLTG | 86 |
|  | PEP070 | PEP062 linked to C-terminal PEP001 | VYDFAFRDLCFFRKNLLRLTG | 87 |

TABLE 8-continued

Amino acid sequences of HPV peptides*

| Peptide pool | Peptide Name | Description | Amino Acid Sequence | SEQ ID NO: |
|---|---|---|---|---|
| PEP006-linked peptides | PEP063 | PEP059 linked to C-terminal PEP006 | QAEPDRAHYNIVTFCCKCDF FRKNWLRLTW | 88 |
| | PEP064 | PEP060 linked to C-terminal PEP006 | RAHYNIVTFFFRKNWLRLTW | 89 |
| | PEP065 | PEP061 linked to C-terminal PEP006 | QLLRREVYDFAFRDLFFRKN WLRLTW | 90 |
| | PEP066 | PEP062 linked to C-terminal PEP006 | VYDFAFRDLCFFRKNWLRLTW | 91 |

*The PEP001 and PEP006 sequences in the polypeptides are underlined

Recombinant human Hsc70 (rhHsc70) protein was purified from rhHsc70-expressing *E. coli* by chromatography using, sequentially, a weak anionic Q Sepharose column, an ATP agarose affinity column, and a DEAE-FF weak anion exchange column. The purified rhHsc70 protein was diluted in filtered PBS supplemented with 0.01% Polysorbate 20.

For vaccines preparation, an equimolar pool of four polypeptides was prepared in 75% DMSO at a total concentration of 320 µM. The purified rhHsc70 protein was pre-incubated at 37° C. for 30 minutes, and the polypeptide pool was added to the rhHsc70 protein solution at 2:1 or 1:1 molar ratio to reach an rhHsc70 protein concentration of 0.5 mg/ml. The mixture was incubated for 1 hour at 37° C. and filtered sequentially through a 0.8 µm and a 0.2 µm filter. The mixture was then placed on ice for 30 min and stored at −80° C.

For vaccination, six-week-old female C57BL/6J mice purchased from the Jackson Laboratory were maintained in a specific pathogen-free environment. The mice were immunized by subcutaneous injection of the vaccine. Each injection contained a total of 30 µg (about 0.42 nmol) Hsc70 complexed to the peptide pool (0.42 nmol for 1:1 ratio or 0.84 nmol for 2:1 ratio), supplemented with 10 µg of QS-21 Stimulon®, diluted in BioXcell InVivoPure pH 7.0 Dilution Buffer to a final volume of 200 µl. For each injection in the free peptide groups (without complexation with Hsc70), an equimolar pool of the four polypeptides at a total concentration of 10 nmol, supplemented with 10 µg of the adjuvant QS-21 Stimulon®, was diluted in filtered PBS with 0.1% Polysorbate 20 to a final volume of 200 µl. One week after the initial immunization, a boosting dose containing the same amount of vaccine was injected subcutaneously to each mouse.

One week after the second immunization, an IFNγ ELISpot assay was performed. Briefly, immunized mice were euthanized, splenocytes were gently isolated, and 5×10⁵ to 1×10⁶ live cells from each mouse were seeded on a plate previously coated with a murine IFNγ capture antibody. The cells were re-stimulated overnight using the naked peptides (PEP059-062). The cells were removed by lysis, and the IFNγ bound to the capture antibody was detected using a detection antibody couple to horseradish peroxidase (HRP). The number of spots in each well, representing the number of IFNγ-producing cells in this well, was counted using CTL S6 ImmunoSpot® analyzer and software.

As shown in FIG. 5A, HPV vaccines containing PEP001- or PEP006-linked peptides complexed with Hsc70 demonstrated increased immunogenicity as compared to the naked HPV peptides. With these particular HPV peptides, the vaccines containing PEP006-linked peptides complexed with Hsc70 showed a greater immunogenicity than the vaccines containing PEP001-linked peptides complexed with Hsc70 under the conditions used.

To compare the immunogenicity of PEP001- and PEP006-containing vaccines with vaccines employing naked peptides at the same peptide dose, an additional experiment was performed using the same procedure as described above, except that in the absence of Hsc70, the amounts of free peptides were 0.84 nmol and 0.42 nmol in the 2:1 ratio group and 1:1 ratio group, respectively.

As shown in FIG. 5B, HPV vaccines containing PEP001- or PEP006-linked peptides complexed with Hsc70 elicited a greater number of IFNγ-producing splenocytes than the equivalent doses of naked peptide complexed with Hsc70 at mole ratios of 1:1 and 2:1. The vaccines containing PEP001- and PEP006-linked peptides complexed with Hsc70 also elicited a greater response than an equivalent dose of free peptides not complexed with Hsc70 at mole ratios of 1:1 and 2:1. With these particular HPV peptides, the vaccines containing PEP006-linked peptides complexed with Hsc70 showed a greater immunogenicity than the vaccines containing PEP001-linked peptides complexed with Hsc70 under the conditions used.

Figure 6:
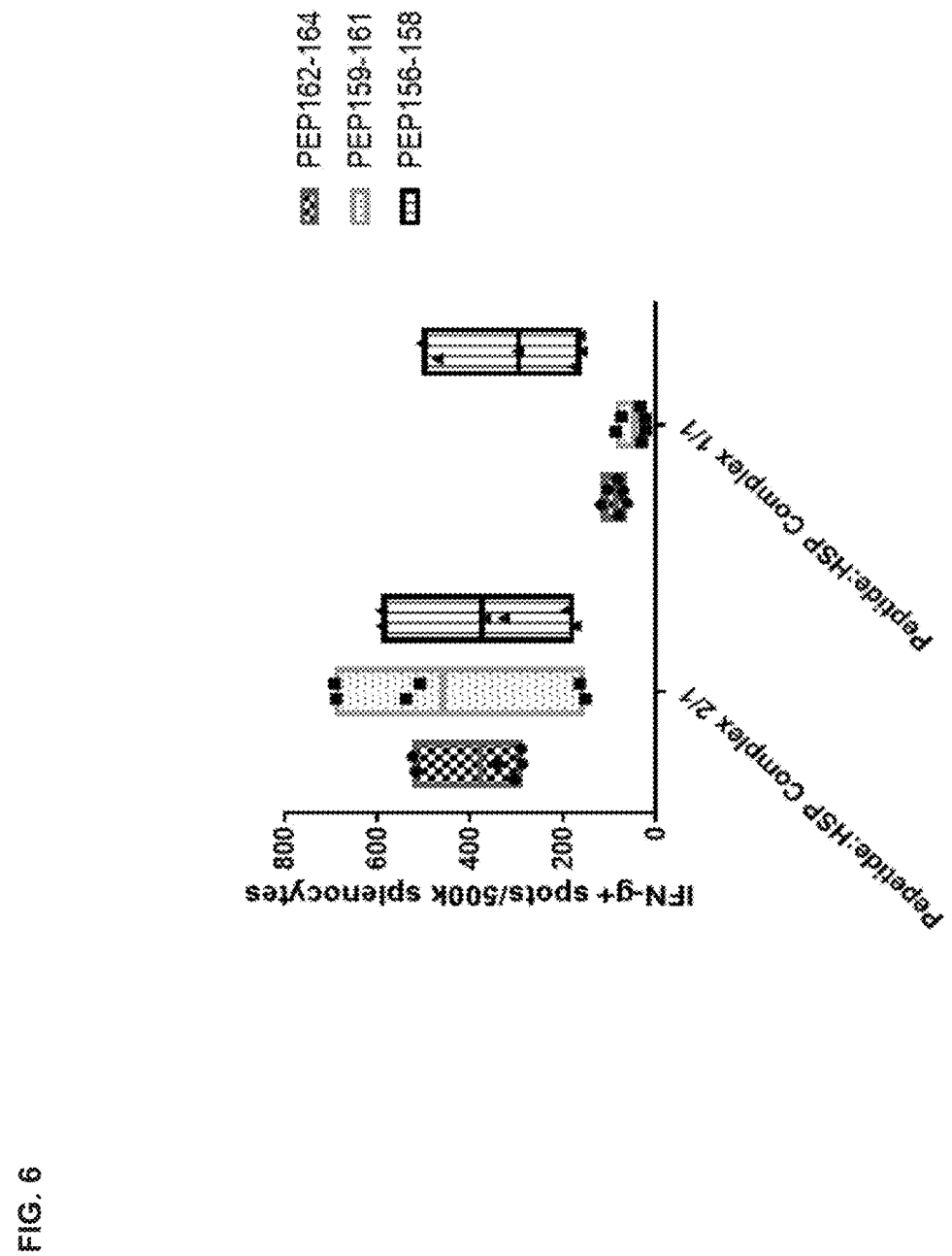
FIG. 6 is a graph showing the relative number of IFNγ-producing splenocytes from mice immunized with the indicated pools of MC38 peptides, either as free peptides, or mixed with Hsc70 protein at 2:1 or 1:1 ratios (n=3 mice per treatment group).

In related experiments, the immunogenicity of three pools of three different MC38 peptides was assessed using the immunogenicity animal model and protocol described above for the HPV E6 or E7 peptides. The details of the MC38 peptide pools are set forth in Table 9. As shown in FIG. 6, all of the peptide pools elicited some level of immune response.

TABLE 9

MC38 peptide vaccine pools*

| Vaccine pool | Peptide Name | Description | Amino Acid Sequence | SEQ ID NO: |
|---|---|---|---|---|
| Naked peptides | PEP156 | MC38 Peptide | GRVLELFRAAQLANDVVLQI MELCGATR | 175 |
| | PEP157 | MC38 Peptide | GIPVHLELASMTNMELMSSI VHQQVFPT | 176 |

TABLE 9-continued

MC38 peptide vaccine pools*

| Vaccine pool | Peptide Name | Description | Amino Acid Sequence | SEQ ID NO: |
|---|---|---|---|---|
| | PEP158 | MC38 Peptide | EAGQSLVISASIIVFNLLELEG DYR | 177 |
| PEP001-linked peptides | PEP159 | PEP156 linked to C-terminal PEP001 | GRVLELFRAAQLANDVVLQI MELCGATR<u>FFRKNLLRLTG</u> | 178 |
| | PEP160 | PEP157 linked to C-terminal PEP001 | GIPVHLELASMTNMELMSSI VHQQVFPT<u>FFRKNLLRLTG</u> | 179 |
| | PEP161 | PEP158 linked to C-terminal PEP001 | EAGQSLVISASIIVFNLLELEG DYR<u>FFRKNLLRLTG</u> | 180 |
| | PEP162 | PEP156 linked to C-terminal PEP006 | GRVLELFRAAQLANDVVLQI MELCGATR<u>FFRKNWLRLTW</u> | 181 |
| PEP006-linked peptides | PEP163 | PEP157 linked to C-terminal PEP006 | GIPVHLELASMTNMELMSSI VHQQVFPT<u>FFRKNWLRLTW</u> | 182 |
| | PEP164 | PEP158 linked to C-terminal PEP006 | EAGQSLVISASIIVFNLLELEG DYR<u>FFRKNWLRLTW</u> | 183 |

*The PEP001 and PEP006 sequences in the polypeptides are underlined.

6.2.2 Increase of Tumor Vaccine Efficacy by HSP-Binding Peptides

This example demonstrates therapeutic efficacy of the HPV vaccine described in Section 6.2.1, using a TC1 HPV16 E6/E7 syngeneic mouse tumor model.

TC1 cells express the oncogenes HRAS, HPV16 E6 and E7 as disclosed in Lin et al. (1996) Cancer Res. 56(1):21-26, which is hereby incorporated by reference in its entirety. Low passage TC1 cells were washed in serum-free PBS and re-suspend in PBS at a concentration of $2\times10^6$ cells/ml. C57BL/6 mice shaved on the flank three days prior to use were injected subcutaneously in the shaved area with $2\times10^5$ cells in 100 µl volume. Vaccines were prepared according to the methods described in Section 6.2.1. The naked peptides, PEP001-linked peptides, and PEP006-linked peptides were complexed with rhHsc70 protein at the ratios of 1:1, 4:1, and 2:1, respectively. The vaccines were administered to the mice subcutaneously at days 5, 10, and 15 post TC1 cell implantation.

Tumors were measured every 3-4 days with a caliper. Tumor volume was calculated using the formula of ½×D× $d^2$, where D is the major axis and d is the minor axis. Any palpable but non-measurable tumor was estimated as 0.5 $mm^3$, whereas absence of tumor was recorded as 0 $mm^3$. Mice were sacrificed when tumors reached 2000 $mm^3$ or upon ulceration, and survival curves were plotted.

As shown in FIGS. 7A-7E, tumor growth in the mice injected with the vaccine comprising PEP001- or PEP006-linked HPV peptides was slower than in the mice injected with the vaccine comprising naked HPV peptides or injected with PBS. Similar therapeutic effects of the vaccines comprising PEP001- and PEP006-linked HPV peptides were observed in the survival curve (FIG. 7F).

Figure 7E:
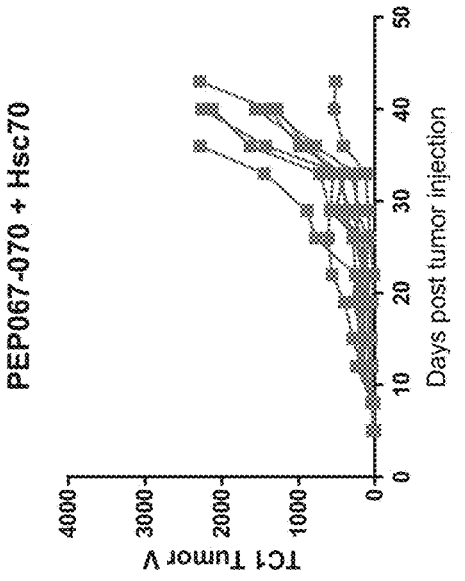
Figure 7B:
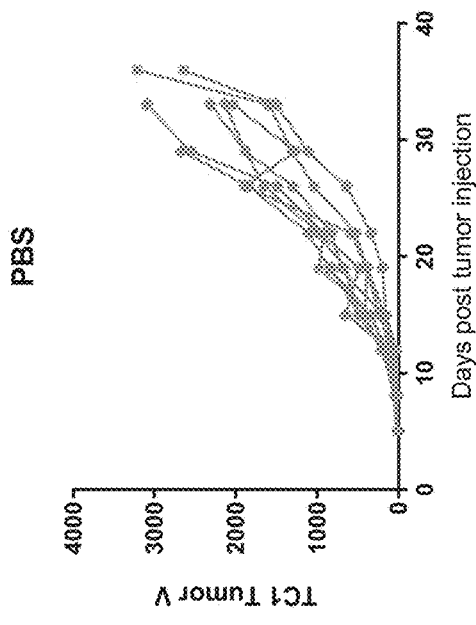
Figure 7D:
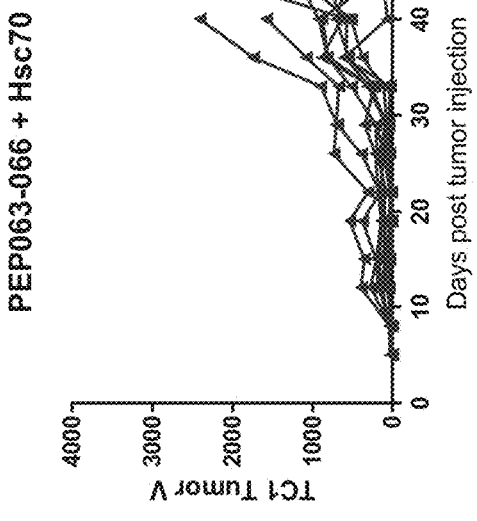
Figure 7F:
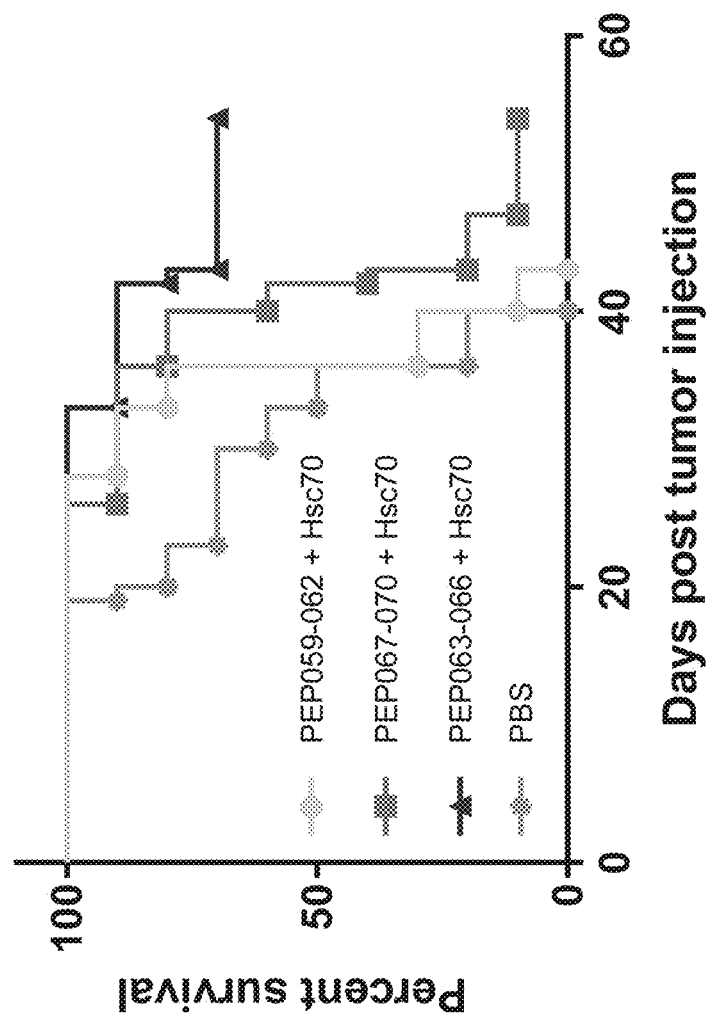

The vaccine comprising PEP006-linked HPV peptides complexed with rhHsc70 was more potent in suppressing tumor growth than the vaccine comprising PEP001-linked HPV peptides complexed with rhHsc70 (FIGS. 7A, 7D, and 7E). Notably, this difference translated into substantial protection against mortality in these experiments (FIG. 7F).

6.2.3 Efficacy of Tumor Vaccines Comprising PEP006 and a Novel Set of HPV Peptides This example demonstrates therapeutic efficacy of an HPV vaccine comprising a novel set of HPV peptides. The sequences of the polypeptides used in the vaccine are provided in Table 4. Specifically, PEP073 and PEP074 comprised the amino acid sequence of EVYDFAFRDL (SEQ ID NO: 92), a murine H-2Db and a human HLA-A*24:02 epitope. PEP081 comprised the amino acid sequences of YMLDLQPET (SEQ ID NO: 93) and MLD-LQPETT (SEQ ID NO: 94), human HLA-A*02:01 epitopes. PEP084 comprised the amino acid sequence of RAHYNIVTF (SEQ ID NO: 78), a murine H-2Db epitope. PEP086 comprised the amino acid sequence of LLMGTL-GIVC (SEQ ID NO: 95), a human HLA-A*02:01 epitope. Each peptide also comprised the amino acid sequence of PEP006.

The vaccine was prepared by the method described in Section 6.2.2, and the ratio of peptide to rhHsc70 protein was 2:1 for the HPV peptide pool. The efficacy of the vaccine was assessed using the same mouse model as described in Section 6.2.2, and the vaccine comprising the pool of PEP063-066 was used as a comparator.

As shown in FIGS. 8A and 8B, the vaccine containing Hsc70 and PEP071-086 reduced tumor growth and improved survival as compared to PBS control in the TC1 HPV16 E6/E7 syngeneic tumor model.

6.2.4 Efficacy of Two Formulations of Tumor Vaccine Comprising PEP006

This example demonstrates therapeutic efficacy of a vaccine using two different formulations, one in which all peptides were initially reconstituted in DMSO and one in which only peptides which were not soluble in neutral, acidic, or basic water, were initially reconstituted in DMSO. The sequences of the polypeptides used in the vaccine, which contain tumor associated antigens from HPV E6 and E7 oncoproteins, are provided in Table 4. Specifically, the vaccine used in this example comprised sixteen peptides, PEP071-PEP086. Each peptide comprises the amino acid sequence PEP006 at the C-terminus.

Two formulations of vaccine were generated for evaluation. In Formulation A, each of the 16 HPV peptides was initially reconstituted from powder in 100% DMSO. Specifically, the peptides were resuspended in 100% DMSO at 25 mg/ml and then equimolar amounts of each peptide were pooled in a solution of 75% DMSO diluted in sterile water at final pool concentration of 320 µM (each peptide @≅20 µM). In Formulation B, each peptide was tested for solubility in neutral water followed by pH-adjusted (i.e. acidic, containing HCl, or basic, containing NaOH) water if necessary. DMSO was used only if the peptide was not soluble in water. Specifically, the 16 peptides were solubilized at 500 μM in neutral water solution, pH adjusted water, or in 100% DMSO (when peptides could not be resuspended in aqueous solutions). The peptides were then mixed at equal volume to make a 500 μM working pool (each peptide @≅31 μM). For both vaccine formulations, the peptides were subsequently diluted in aqueous buffer to the concentration desired for complexation to Hsc70.

For complexation to HSC70, rh-Hsc70 was incubated for 0.5 hour at 37° C., then further incubated for 1 hour at 37° C. with the pool of 16 peptides at 2:1 molar ratio of total peptide:protein, following sterile procedures. Complexes were then incubated on ice for 15 min. The complexes were filtered and aliquoted.

C57BL/6 mice (n=13/group) were injected subcutaneously with 2×10$^5$ live TC-1 tumor cells in the flank followed by treatment with the two formulations of vaccine, both comprising the same 16 overlapping long synthetic peptides covering the full length of the E6 and E7 HPV oncoproteins or PBS control. On days 5, 10, and 15 after tumor challenge mice were administered (a) 30 μg Hsc70-based vaccine (either Formulation A or Formulation B)+10 μg QS-21 or (b) PBS subcutaneously at the diagonally opposite brachial lymph node area from the tumor site. Each dose of vaccine contained 30 μg Hsc70 and ~4 μg total peptide (~250 ng each peptide) along with QS-21 adjuvant. Injections were carried out with a 1 mL BD Syringe with a Sub-Q 26G×⅝ inch needle.

Tumor growth kinetics and survival were monitored. Tumor volumes were measured by caliper every 3-4 days of the study starting on day 5 after tumor challenge. Tumor length was based on the longest linear distance. Width was based on the longest linear distance perpendicular to the length. Mice were euthanized when tumor volumes reached 2000 mm$^3$. Tumor volumes (mm$^3$) were calculated as length×width$^2$×0.5. For mice with two tumors, each was measured independently and the volumes summed. Mice were distributed to each treatment group randomly on day 5 post tumor inoculation. Mice without early measurable tumors were excluded from the study. Ten mice per group were followed for survival using the Kaplan-Meier method and Log-rank test (p≤0.0001 survival in mice treated with either vaccine formulation vs. survival in mice treated with PBS). Tumor size was assessed every 2-3 days and each group's mean tumor volume was plotted as function of time.

Tumors grew rapidly in control mice treated with PBS (FIGS. 9A and 9B). In contrast, a significant delay in the rate of tumor growth was observed in mice treated with either vaccine formulation (FIGS. 9A and 9B) (tumor growth in mice treated with Formulation A compared to tumor growth in mice treated with PBS p≤0.01 and tumor growth mice treated with Formulation B compared to tumor growth in mice treated with PBS **p≤0.0001: Wilcoxon Rank Sum Test). Tumor growth kinetics of individual mice were plotted as a function of time. Prolonged survival was observed in mice treated with either Formulation A or Formulation B as compared to mice treated with PBS (FIG. 9C).

The TC-1 tumor is known to develop a resistance phenotype to antigen targeting therapies which can be driven by immune editing and loss of epitopes expressed by the tumor (Smahel et al., 2007) which likely explains the eventual progression of tumors beginning on ~d. 28 for both vaccine formulations. Together, these data demonstrate that an efficient vaccine-induced immune response against tumor associated antigens such as HPV E6 and E7 oncoproteins can translate into significant tumor control and prolonged survival.

6.3 Example 3: Improvement of Peptide Synthesis by Hsc70-Binding Peptides

This example demonstrates the ability of PEP001 and PEP006 to improve crude purity of peptides during synthesis.

6.3.1 Improvement of Crude Purity of Ova Antigen Peptide by Addition of PEP001 or PEP006

An Ova antigen peptide comprising the amino acid sequence of EVSGLEQLESIINFEKLTEWTSSNVME (PEP053, SEQ ID NO: 97), either naked or linked to PEP001 (PEP052, SEQ ID NO: 230, EVSGLEQLESIIN-FEKLTEWTSSNVMEFFRKNLLRLTG) or PEP006 (PEP054, SEQ ID NO: 231, EVSGLEQLESIIN-FEKLTEWTSSNVMEFFRKNWLRLTW), were synthesized by the method described in Section 6.1.1. This Ova antigen peptide comprised an MHC-binding epitope having the amino acid sequence of SIINFEKL (SEQ ID NO: 96). Peptide purity was determined by reverse phase chromatography using the Vanquish Bioanalytical and Ultimate 3000 Dionex workstation, following the procedure provided in the *Vanquish Ultimate 3000 User's Guide and Data Explorer User's Guide* included with the Chromeleon 7.0 software package.

After cycles of amino acid residue addition, the synthesized peptides were cleaved from the resin and dissolved in 1:1 acetonitrile:water (v/v) at 1 mg/mL concentration. The dissolved sample was analyzed by analytical HPLC using a Phenomenex Luna C18 10 μm 4.6×250 mm column. A volume of 20 μL of sample was injected, and was subject to gradient elution using a mixture of solution A (0.1% TFA in water) and solution B (0.1% TFA in acetonitrile) as mobile phase, following the gradient of Table 10. The column temperature was maintained at 37° C.±5° C. The peptides were detected by UV absorbance at the wavelengths of 214 nm and 280 nm.

TABLE 10

Gradient table for HPLC mobile phase

| Time (min) | Flow (mL/min) | % Solution A | % Solution B | Curve |
|---|---|---|---|---|
| 0 | 1 | 95 | 5 | 5 |
| 0.01 | 1 | 95 | 5 | 5 |
| 25 | 1 | 35 | 65 | 5 |
| 25.01 | 1 | 5 | 95 | 5 |
| 31 | 1 | 5 | 95 | 5 |
| 31 | 1 | 95 | 5 | 5 |
| 40 | 1 | 95 | 5 | 5 |

In an elution curve, each peak represented a peptide with a specific retention time, and the area under the peak reflected the amount of this peptide. The peak of the correct peptide was confirmed by mass spectrometry. The crude purity of the peptide was calculated as the area under the peak of the correct peptide divided by the total area under the entire curve.

As shown in FIG. 10A, the naked Ova peptide (middle panel) had a heterogeneous signal. By contrast, the Ova-PEP001 (upper panel) and Ova-PEP006 (lower panel) preparations showed nearly a single peak at the expected retention time. Quantification of the chromatograms also indicated that Ova-PEP001 and Ova-PEP006 had substantially increased crude purity (FIG. 10B). This result was contrary to the general rule that longer peptides were more difficult to synthesize and purify, and suggested that PEP001 and PEP006 improved the crude purity in chemical synthesis of peptide.

6.3.2 Improvement of Crude Purity of a Range of Peptides by Addition of PEP006

The 50 peptides shown below in Table 11 were synthesized by the method described in Section 6.1.1. This group of 50 peptides contains 25 unique peptide sequences (labelled A-Y) that were synthesized with or without ("naked peptide") the addition of a C-terminal PEP006 peptide sequence. Peptide purity was determined by reverse phase chromatography as described in section 6.3.1 above. As shown in FIG. 11, addition of the PEP006 peptide sequence increased the crude purity for a majority of the peptides as compare to the corresponding naked peptide. Because of the sample complexity, many peptide separations were multi-dimensional. Three peptides were not detected in the C18 column under standard reverse phase gradient up to 95%. For these three peptides, there was no detectable peak to integrate throughout the gradient and crude purity was listed as zero. Possible causes of the lack of detection of the three peptides could include adherence of the sample to the C18 column or the storage vial, and/or the sample dropping out of solution.

TABLE 11

| | Peptides | | | | | |
|---|---|---|---|---|---|---|
| | Naked Peptide Sequence | | | Peptide Sequence including PEP006 | | |
| | Sequence | Peptide Name | SEQ ID NO: | Sequence | Peptide Name | SEQ ID NO: |
| A | KFPLILYLGMAIVTVLYISLGSLGYLQ | PEP105 | 114 | KFPLILYLGMAIVTVLYISLGSLGYLQFFRKNWLRLTW | PEP130 | 139 |
| B | TMRGCGPCLRIAPSFSSMSNKYPQAVF | PEP106 | 115 | TMRGCGPCLRIAPSFSSMSNKYPQAVFFFRKNWLRLTW | PEP131 | 140 |
| C | RMKKENLMPREELARLFPNLPELIEIH | PEP107 | 116 | RMKKENLMPREELARLFPNLPELIEIHFFRKNWLRLTW | PEP132 | 141 |
| D | FSRTWIGIWSVLCFASTLFTVLTYLVD | PEP108 | 117 | FSRTWIGIWSVLCFASTLFTVLTYLVDFFRKNWLRLTW | PEP133 | 142 |
| E | TSLAIGTKSGYKLFSLSSVEQLDQVHG | PEP109 | 118 | TSLAIGTKSGYKLFSLSSVEQLDQVHGFFRKNWLRLTW | PEP134 | 143 |
| F | LFPTDCHSVPPHYTELLTFHSKEGTDH | PEP110 | 119 | LFPTDCHSVPPHYTELLTFHSKEGTDHFFRKNWLRLTW | PEP135 | 144 |
| G | PSRGSSSSSGYPVGVVFQPVGSGGVQP | PEP111 | 120 | PSRGSSSSSGYPVGVVFQPVGSGGVQPFFRKNWLRLTW | PEP136 | 145 |
| H | LSPGAAAPSGWALAPLGDTMKIYMELQ | PEP112 | 121 | LSPGAAAPSGWALAPLGDTMKIYMELQFFRKNWLRLTW | PEP137 | 146 |
| I | ELYRKLLRSQSVRFCFQGLLENSAHLI | PEP113 | 122 | ELYRKLLRSQSVRFCFQGLLENSAHLIFFRKNWLRLTW | PEP138 | 147 |
| J | AQVIILNHPGQISTGYAPVLDCHTAHI | PEP114 | 123 | AQVIILNHPGQISTGYAPVLDCHTAHIFFRKNWLRLTW | PEP139 | 148 |
| K | PVQLWVSATPPAGSPVRAMAIYKKSQH | PEP115 | 124 | PVQLWVSATPPAGSPVRAMAIYKKSQHFFRKNWLRLTW | PEP140 | 149 |
| L | NAFNPLNASASLPPAAMPITTADGRSD | PEP116 | 125 | NAFNPLNASASLPPAAMPITTADGRSDFFRKNWLRLTW | PEP141 | 150 |
| M | VGSVAGNKLLRAAWRRASLAATSLALG | PEP117 | 126 | VGSVAGNKLLRAAWRRASLAATSLALGFFRKNWLRLTW | PEP142 | 151 |
| N | AETSLLEAGASAASTAAALENLQVEAS | PEP118 | 127 | AETSLLEAGASAASTAAALENLQVEASFFRKNWLRLTW | PEP143 | 152 |

TABLE 11-continued

Peptides

| | Naked Peptide Sequence | | | Peptide Sequence including PEP006 | |
|---|---|---|---|---|---|
| | Sequence | Peptide Name | SEQ ID NO: | Sequence | Peptide Name | SEQ ID NO: |
| O | NSVLQTLLQMR AAKSSVAPSREE LLGT | PEP119 | 128 | NSVLQTLLQMRAAKSS VAPSREELLGTFFFRKN WLRLTW | PEP144 | 153 |
| P | DFTHPEAREWFQ GLLRRLRLRYNV TSF | PEP120 | 129 | DFTHPEAREWFQGLLR RLRLRYNVTSFFFRKN WLRLTW | PEP145 | 154 |
| Q | KKHDVRSIIGSPG LPFPALHPLDIM AD | PEP121 | 130 | KKHDVRSIIGSPGLPFPA LHPLDIMADFFRKNWL RLTW | PEP146 | 155 |
| R | AGRPRPVLRSVN SLEPSQVIFCNRS PR | PEP122 | 131 | AGRPRPVLRSVNSLEPS QVIFCNRSPRFFRKNWL RLTW | PEP147 | 156 |
| S | TFFASDNAVDIT TLTNSCLSNSDH SRD | PEP123 | 132 | TFFASDNAVDITTLTNS CLSNSDHSRDFFRKNW LRLTW | PEP148 | 157 |
| T | TLLRSSYVAQVP LLTLCTRGPPEE DAP | PEP124 | 133 | TLLRSSYVAQVPLLTLC TRGPPEEDAPFFRKNW LRLTW | PEP149 | 158 |
| U | MFSFNMFDHPIP LVFQNRFSTQYR | PEP125 | 134 | MFSFNMFDHPIPLVFQN RFSTQYRFFRKNWLRL TW | PEP150 | 159 |
| V | ATAAGSSTISQD TIHLTSGPVSALA SG | PEP126 | 135 | ATAAGSSTISQDTIHLTS GPVSALASGFFRKNWL RLTW | PEP151 | 160 |
| W | ACSSSYNSAVME SSSVNVSMVHSS SKE | PEP127 | 136 | ACSSSYNSAVMESSSV NVSMVHSSSKEFFRKN WLRLTW | PEP152 | 161 |
| X | VLQEWKACDKL YDVATMRTTQL TYSME | PEP128 | 137 | VLQEWKACDKLYDVA TMRTTQLTYSMEFFRK NWLRLTW | PEP153 | 162 |
| Y | RDPFRVRASAAL LNKLYAMGLVP TRGS | PEP129 | 138 | RDPFRVRASAALLNKL YAMGLVPTRGSFFRKN WLRLTW | PEP154 | 163 |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

What is claimed:

1. An isolated polypeptide comprising:
   (a) an antigenic peptide comprising one or more major histocompatibility complex (MHC)-binding epitopes; and
   (b) a heat shock protein (HSP)-binding peptide comprising the amino acid sequence of $X_1LX_2LTX_3$ (SEQ ID NO: 1), wherein $X_1$ is W or F; $X_2$ is R or K; and $X_3$ is W, F, or G.

2. An isolated polypeptide comprising:
   (a) an antigenic peptide comprising one or more major histocompatibility complex (MHC)-binding epitopes; and
   (b) an HSP-binding peptide comprising the amino acid sequence of $NWX_1X_2X_3X_4X_5$ (SEQ ID NO: 232), wherein $X_1$ is L or I; $X_2$ is L, R, or K; $X_3$ is L or I; $X_4$ is T, L, F, K, R, or W; and $X_5$ is W or K.

3. The isolated polypeptide of claim 2, wherein the HSP-binding peptide comprises an amino acid sequence selected from the group consisting of SEQ ID NOs: 204, 208-211, and 213-215, optionally wherein the amino acid sequence of the HSP-binding peptide consists of an amino acid sequence selected from the group consisting of SEQ ID NOs: 204, 208-211, and 213-215.

4. An isolated polypeptide comprising:
   (a) an antigenic peptide comprising one or more major histocompatibility complex (MHC)-binding epitopes; and
   (b) an HSP-binding peptide comprising the amino acid sequence of SEQ ID NO: 205, optionally wherein the amino acid sequence of the HSP-binding peptide consists of the amino acid sequence of SEQ ID NO: 205.

5. An isolated polypeptide comprising an HSP-binding peptide comprising an amino acid sequence selected from the group consisting of SEQ ID NOs: 1-12, 98-113, 204, 205, 207-215, and 232, and an antigenic peptide comprising an amino acid sequence selected from the group consisting of SEQ ID NOs: 38-53, optionally wherein:
   (a) the amino acid sequence of the antigenic peptide consists of an amino acid sequence selected from the group consisting of SEQ ID NOs: 38-53; and/or
   (b) the amino acid sequence of the HSP-binding peptide consists of an amino acid sequence selected from the group consisting of SEQ ID NOs: 1-12, 98-113, 204, 205, 207-215, and 232.

6. A composition comprising a complex of the polypeptide of claim 1 and a purified stress protein.

7. The composition of claim 6:
   (a) wherein the stress protein is selected from the group consisting of Hsc70, Hsp70, Hsp90, Hsp110, Grp170, Gp96, Calreticulin, and a mutant or fusion protein thereof, optionally wherein the stress protein is human Hsc70;
   (b) wherein the stress protein is a recombinant protein;
   (c) wherein the composition comprises at least 2, 3, 4, 5, 6, 7, 8, 9, 10, 11, 12, 13, 14, 15, 16, 17, 18, 19, or 20 different polypeptides, optionally wherein each of the different polypeptides comprises the same HSP-binding peptide and a different antigenic peptide, optionally wherein:
   each one of the polypeptides comprises an amino acid sequence selected from the group consisting of SEQ ID NOs: 54-69,
   the amino acid sequence of each one of the polypeptides consists of an amino acid sequence selected from the group consisting of SEQ ID NOs: 54-69;

(d) wherein the amount of the stress protein in the composition is about 10 µg to 600 µg, optionally about 250 µg to 290 µg;
(e) wherein the molar ratio of the polypeptide(s) to the stress protein is about 0.5:1 to 5:1, optionally about 1:1 to 2:1, such as 1:1, 1.25:1, or 1.5:1;
(f) wherein the total amount of the polypeptide(s) and stress protein in the composition is about 10 µg to 600 µg, optionally about 300 µg;
(g) wherein the composition further comprises an adjuvant, optionally wherein the adjuvant comprises:
a saponin or an immunostimulatory nucleic acid, optionally wherein the adjuvant comprises QS-21, optionally about 10 µg, 25 µg, or 50 µg of the QS-21, and/or
a TLR agonist, optionally a TLR4 agonist, TLR5 agonist, TLR7 agonist, TLR8 agonist, and/or TLR9 agonist;
(h) which is a pharmaceutical composition comprising a pharmaceutically acceptable carrier or excipient; and/or
(i) wherein the composition is in a unit dosage form.

8. A composition comprising a plurality of the polypeptides of claim 1.

9. The composition of claim 8, wherein the antigenic peptide of each one of the polypeptides comprises an amino acid sequence selected from the group consisting of SEQ ID NOs: 38-53, optionally wherein the composition comprises at least 2, 3, 4, 5, 6, 7, 8, 9, 10, 11, 12, 13, 14, 15, or 16 different antigenic peptides.

10. A method of inducing a cellular immune response to an antigenic peptide in a subject, the method comprising administering to the subject an effective amount of a composition of claim 6, optionally wherein the composition is in a unit dosage form.

11. The method of claim 10, wherein:
(a) the subject has cancer, optionally wherein the MHC-binding epitope is present in the subject's cancer cells;
(b) the subject has an infection of a pathogenic microbe, optionally wherein the MHC-binding epitope is present in the pathogenic microbe;
(c) wherein the composition is administered to the subject weekly for four weeks, optionally wherein:
at least two further doses of the composition or unit dosage form are administered biweekly to the subject after the four weekly doses,
at least one booster dose of the composition or unit dosage form is administered three months after the final weekly or biweekly dose, and/or
the composition or unit dosage form is further administered every three months for at least 1 year;
(d) further comprising administering to the subject lenalidomide, dexamethasone, interleukin-2, recombinant interferon alfa-2b, or PEG-interferon alfa-2b;
(e) further comprising administering to the subject an indoleamine dioxygenase-1 (IDO-1) inhibitor, optionally wherein the IDO-1 inhibitor is 4-amino-N-(3-chloro-4-fluorophenyl)-N'-hydroxy-1,2,5-oxadiazole-3-carboximidamide; and/or
(f) further comprising administering to the subject an immune checkpoint antibody, optionally wherein the immune checkpoint antibody is selected from the group consisting of an agonistic anti-GITR antibody, an agonistic anti-OX40 antibody, an antagonistic anti-PD-1 antibody, an antagonistic anti-CTLA-4 antibody, an antagonistic anti-TIM-3 antibody, an antagonistic anti-LAG-3 antibody, an antagonistic anti-TIGIT antibody, an agonistic anti-CD96 antibody, an antagonistic anti-VISTA antibody, an antagonistic anti-CD73 antibody, an agonistic anti-CD137 antibody, an antagonist anti-CEACAM1 antibody, an agonist anti-ICOS antibody, and an antigen-binding fragment thereof.

12. A kit comprising a first container containing one or more polypeptide of claim 1, and a second container containing a purified stress protein capable of binding to the polypeptide.

13. The kit of claim 12, wherein:
(a) the first container contains 2-20 different polypeptides, optionally wherein each of the different polypeptides comprises the same HSP-binding peptide and a different antigenic peptide;
(b) the total amount of the polypeptide(s) in the first container is about 0.1 to 20 nmol, optionally about 3, 4, 5, or 6 nmol;
(c) the stress protein is selected from the group consisting of Hsc70, Hsp70, Hsp90, Hsp110, Grp170, Gp96, Calreticulin, and a mutant thereof, optionally wherein the stress protein is human Hsc70;
(d) the stress protein is a recombinant protein;
(e) the amount of the stress protein in the second container is about 10 µg to 600 µg, optionally about 250 µg to 290 µg;
(f) the molar ratio of the polypeptide to the stress protein is about 0.5:1 to 5:1, optionally about 1:1 to 2:1;
(g) the total amount of the polypeptide(s) in the first container and the stress protein in the second container is about 10 µg to 600 µg, optionally 300 µg; and/or
(h) the kit further comprises a third container containing an adjuvant, and optionally wherein the adjuvant comprises:
a saponin or an immunostimulatory nucleic acid, optionally QS-21, optionally 10 µg, 25 µg, or 50 µg of QS-21, and/or
a TLR agonist, optionally a TLR4 agonist, TLR5 agonist, TLR7 agonist, TLR8 agonist, and/or TLR9 agonist.

14. A method of making a vaccine, the method comprising mixing one or more polypeptides of claim 1 with a purified stress protein under suitable conditions such that the purified stress protein binds to at least one of the polypeptides.

15. The method of claim 14, wherein:
(a) the stress protein is selected from the group consisting of Hsc70, Hsp70, Hsp90, Hsp110, Grp170, Gp96, Calreticulin, and a mutant thereof, optionally wherein the stress protein is human Hsc70;
(b) the stress protein is a recombinant protein;
(c) the molar ratio of the polypeptide to the stress protein is about 0.5:1 to 5:1, optionally about 1:1 to 2:1; and/or
(d) the suitable conditions comprise a temperature of about 37° C.

16. The isolated polypeptide of claim 1, wherein the HSP-binding peptide comprises the amino acid sequence of $NX_1LX_2LTX_3$ (SEQ ID NO: 2), wherein $X_1$ is W or F; $X_2$ is R or K; and $X_3$ is W, F, or G.

17. The isolated polypeptide of claim 1, wherein the HSP-binding peptide comprises the amino acid sequence of $WLX_1LTX_2$ (SEQ ID NO: 3), wherein $X_1$ is R or K; and $X_2$ is W or G.

18. The isolated polypeptide of claim 1, wherein the HSP-binding peptide comprises the amino acid sequence of NWLX1LTX2 (SEQ ID NO: 4), wherein X1 is R or K; and X2 is W or G.

19. The isolated polypeptide of claim 1, wherein the HSP-binding peptide comprises an amino acid sequence selected from the group consisting of SEQ ID NOs: 5-12, 98-113, 207, and 212.

20. The isolated polypeptide of claim 1, wherein the amino acid sequence of the HSP-binding peptide consists of an amino acid sequence selected from the group consisting of SEQ ID NOs: 5-12, 98-113, 207, and 212.

21. The isolated polypeptide of claim 1, wherein the polypeptide is 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

22. The isolated polypeptide of claim 1, wherein the MHC-binding epitope is from a cancer cell and wherein the MHC-binding epitope comprises an amino acid mutation or a gene fusion mutation of the cancer cell, optionally wherein
the amino acid mutation is a substitution, deletion, or insertion mutation, and/or
the amino acid mutation or gene fusion mutation is at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of the amino acid sequence of the antigenic peptide.

23. The isolated polypeptide of claim 1, wherein the MHC-binding epitope is from a pathogenic microbe, optionally wherein the pathogenic microbe is a virus, optionally a human papillomavirus (HPV) and the antigenic peptide comprises an amino acid sequence selected from the group consisting of SEQ ID NOs: 38-53.

24. The isolated polypeptide of claim 1, wherein the MHC-binding epitope comprises a modified amino acid residue, optionally wherein:
(a) the modified amino acid residue is a Tyr, Ser, Thr, Arg, Lys, or His that has been phosphorylated on a side chain hydroxyl or amine;
(b) the modified amino acid residue is a mimetic of a Tyr, Ser, Thr, Arg, Lys, or His amino acid that has been phosphorylated on a side chain hydroxyl or amine, optionally wherein the mimetic is a non-hydrolyzable analogue of a phosphorylated residue;
(c) the modified amino acid residue is an Asn that has been glycosylated on a side chain amide, a Ser or Thr that has been glycosylated on a side chain hydroxyl, a Lys or Arg that has been methylated on a side chain amino, a Lys that has been acetylated on a side chain amino, an N-terminal residue that has been acetylated on the α-amino, or a C-terminal residue that has been amidated on the α-carboxyl; and/or
(d) the modified amino acid residue is at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of the amino acid sequence of the antigenic peptide.

25. The isolated polypeptide of claim 1, wherein the HSP-binding peptide is linked to the antigenic peptide via a peptide linker and wherein the peptide linker comprises the amino acid sequence of SEQ ID NO: 13 or FR, and optionally comprises an amino acid sequence selected from the group consisting of SEQ ID NOs: 18-25, 71, 72, 74, 75, 166, 167, 173, and 174.

26. The isolated polypeptide of claim 1, wherein the HSP-binding peptide is linked to the antigenic peptide via a peptide linker and wherein the HSP-binding peptide is at the C-terminus of the polypeptide.

27. The isolated polypeptide of claim 26, comprising the amino acid sequence of FFRKX$_1$LX$_2$LTX$_3$ (SEQ ID NO: 14), wherein X$_1$ is W or F; X$_2$ is R or K; and X$_3$ is W, F, or G.

28. The isolated polypeptide of claim 26, comprising the amino acid sequence of FFRKNX$_1$LX$_2$LTX$_3$ (SEQ ID NO: 15), wherein X$_1$ is W or F; X$_2$ is R or K; and X$_3$ is W, F, or G.

29. The isolated polypeptide of claim 26, comprising the amino acid sequence of FFRKWLX$_1$LTX$_2$ (SEQ ID NO: 16), wherein X$_1$ is R or K; and X$_2$ is W or G.

30. The isolated polypeptide of claim 26, comprising the amino acid sequence of FFRKNWLX$_1$LTX2 (SEQ ID NO: 17), wherein X$_1$ is R or K; and X$_2$ is W or G.

31. The isolated polypeptide of claim 26, comprising the amino acid sequence of FFRKNWX$_1$X$_2$X$_3$X$_4$X$_5$ (SEQ ID NO: 233), wherein X$_1$ is L or I; X$_2$ is L, R, or K; X$_3$ is L or I; X$_4$ is T, L, F, K, R, or W; and X5 is W or K, at the C-terminus of the polypeptide.

32. The isolated polypeptide of claim 1, wherein the HSP-binding peptide is linked to the antigenic peptide via a peptide linker and wherein the HSP-binding peptide is at the N-terminus of the polypeptide.

33. The isolated polypeptide of claim 32, comprising the amino acid sequence of X$_1$LX$_2$LTX$_3$FFRK (SEQ ID NO: 26), wherein X$_1$ is W or F; X$_2$ is R or K; and X$_3$ is W, F, or G.

34. The isolated polypeptide of claim 32, comprising the amino acid sequence of NX$_1$LX$_2$LTX$_3$FFRK (SEQ ID NO: 27), wherein X$_1$ is W or F; X$_2$ is R or K; and
X$_3$ is W, F, or G.

35. The isolated polypeptide of claim 32, comprising the amino acid sequence of WLX$_1$LTX$_2$FFRK (SEQ ID NO: 28), wherein X$_1$ is R or K; and X$_2$ is W or G.

36. The isolated polypeptide of claim 32, comprising the amino acid sequence of NWLX$_1$LTX$_2$FFRK (SEQ ID NO: 29), wherein X$_1$ is R or K; and X$_2$ is W or G.

37. The isolated polypeptide of claim 32, comprising the amino acid sequence of NWX$_1$X$_2$X$_3$X$_4$X$_5$FFRK (SEQ ID NO: 234), wherein X$_1$ is L or I; X$_2$ is L, R, or K; X$_3$ is L or I; X$_4$ is T, L, F, K, R, or W; and X$_5$ is W or K, at the N-terminus of the polypeptide.

38. The isolated polypeptide of claim 1, wherein the HSP-binding peptide is linked to the antigenic peptide via a peptide linker and wherein the polypeptide comprises an amino acid sequence selected from the group consisting of SEQ ID NOs: 30-37, and 216-229.

39. The isolated polypeptide of claim 1, wherein the polypeptide comprises an amino acid sequence selected from the group consisting of SEQ ID NOs: 54-69.

40. The isolated polypeptide of claim 1, wherein the polypeptide consists of an amino acid sequence selected from the group consisting of SEQ ID NOs: 54-69.

41. An isolated polypeptide comprising:
(a) an antigenic peptide comprising one or more major histocompatibility complex (MHC)-binding epitopes; and
(b) a heat shock protein (HSP)-binding peptide comprising the amino acid sequence of SEQ ID NO: 6.

42. The isolated polypeptide of claim 41, wherein the HSP-binding peptide consists of the amino acid sequence of SEQ ID NO: 6.

43. A pharmaceutical composition comprising the isolated polypeptide of claim 42.

* * * * *